(12) United States Patent
Andrews et al.

(10) Patent No.: US 8,735,660 B2
(45) Date of Patent: May 27, 2014

(54) METHODS FOR THE PRODUCTION OF PLANTS RESISTANT TO HPPD HERBICIDES

(75) Inventors: Christopher John Andrews, Bracknell (GB); Simon Anthony James Warner, Bracknell (GB); Timothy Robert Hawkes, Bracknell (GB)

(73) Assignee: Syngenta Limited (GB)

( * ) Notice: Subject to any disclaimer, the term of this patent is extended or adjusted under 35 U.S.C. 154(b) by 1152 days.

(21) Appl. No.: 11/977,793

(22) Filed: Oct. 26, 2007

(65) Prior Publication Data

US 2008/0146447 A1 Jun. 19, 2008

Related U.S. Application Data

(62) Division of application No. 10/416,940, filed as application No. PCT/GB01/05028 on Nov. 14, 2001, now Pat. No. 7,312,379.

(30) Foreign Application Priority Data

Dec. 7, 2000 (GB) .................................. 0029899.2
Jul. 17, 2001 (GB) .................................. 0117393.9

(51) Int. Cl.
*C12N 15/82* (2006.01)
*C12N 15/29* (2006.01)

(52) U.S. Cl.
USPC ......................... 800/300; 536/23.2; 800/278

(58) Field of Classification Search
None
See application file for complete search history.

(56) References Cited

U.S. PATENT DOCUMENTS 6,069,115 A * 5/2000 Pallett et al. .................. 504/270
6,245,968 B1 * 6/2001 Boudec et al. ............... 800/278
7,312,379 B2 * 12/2007 Andrews et al. ............. 800/300

FOREIGN PATENT DOCUMENTS

| WO | WO 97/49816 | 12/1997 |
|---|---|---|
| WO | WO 98/04685 | 2/1998 |
| WO | WO 98/20144 | 5/1998 |
| WO | WO 99/04021 | 1/1999 |
| WO | WO 00/32757 | 6/2000 |

OTHER PUBLICATIONS

Broun et al., Catalytic plasticity of fatty acid modification enzymes underlying chemical diversity of plant lipids. Science, 1998, vol. 282: 1315-1317.
Kisselev L., Polypeptide release factors in prokaryotes and eukaryotes: same function, different structure. Structure, 2002, vol. 10: 8-9.
Wishart et al, A single mutation converts a novel phosphotyrosine binding domain into a dual-specificity phosphatase. J. biol. Chem., 1995, vol. 270(45): 26782-26785.
Witkowski et al., Conversion of a beta-ketoacyl synthase to a malonyl decarboxylase by replacement of the active-site cysteine with glutamine. Biochemistry, 1999, vol. 38: 11643-11650.
Garcia et al., "Characterization and Subcellular Compartmentation of Recombinant 4-Hydroxyphenylpyruvate Dioxygenase from *Arabidopsis* in Transgenic Tobacco," Plant Physiology, 119:1507-1516(1999).
Devos et al., Practical limits of function prediction. *Proteins: Structure, Function, and Genetics.* 2000, vol. 41: 98-107.
Seffernick et al., Melamine deaminase and Atrazine chlorohydrolase: 98 percent identical but functionally different. *J. Bacteriol.*, 2001, vol. 183 (8): 2405-2410.

* cited by examiner

*Primary Examiner* — David H Kruse
(74) *Attorney, Agent, or Firm* — S. Matthew Edwards

(57) ABSTRACT

Methods for making transgenic plants that are resistant to HPPD herbicides are presented. Polynucleotides other than those from *Pseudomonas fluorescens* that encode resistant HPPD enzymes are enclosed for use in the process of making transgenic plants that are tolerant to HPPD-inhibiting herbicides.

13 Claims, 5 Drawing Sheets

Figure 1. Exchange of $^{14}C$ mesotrione from wheat and from *Arabidopsis* HPPD
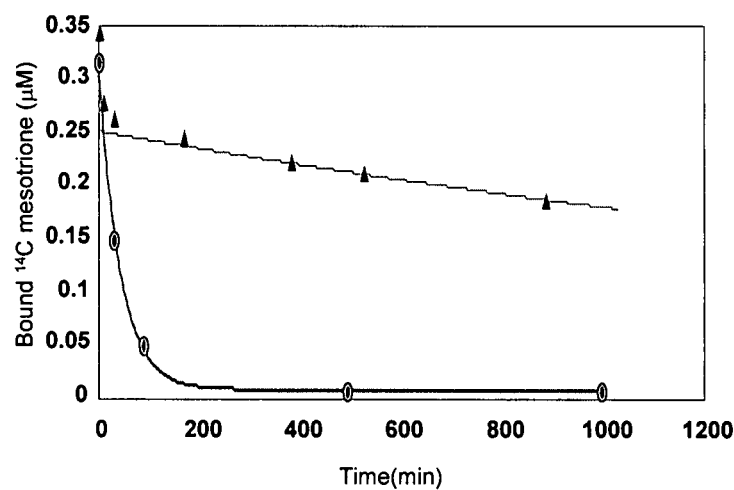
circles represent data from wheat HPPD, triangles data obtained from *Arabidopsis* HPPD Figure 2. Exchange of mesotrione and of structure II bound to *Arabidopsis* HPPD with excess $^{14}C$ mesotrione.
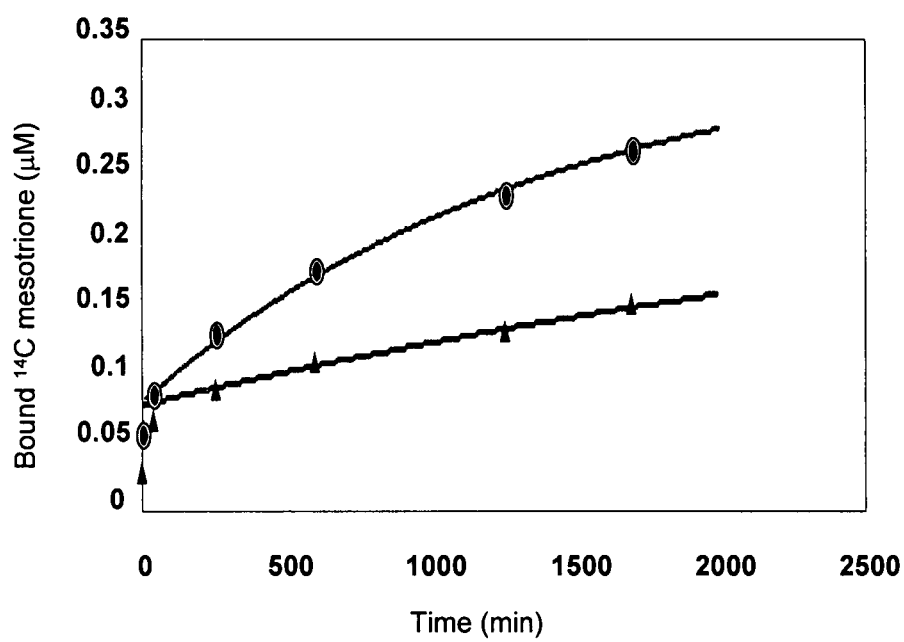

Figure 3. Progressive inhibition of wheat HPPD by structure II
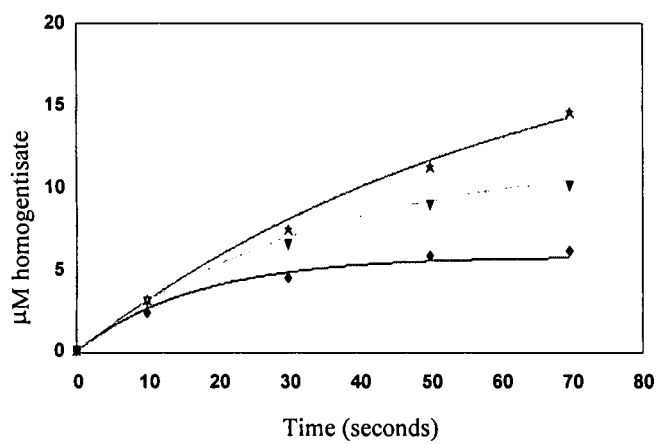

Figure 4. Progressive inhibition of wheat HPPD by structure VI
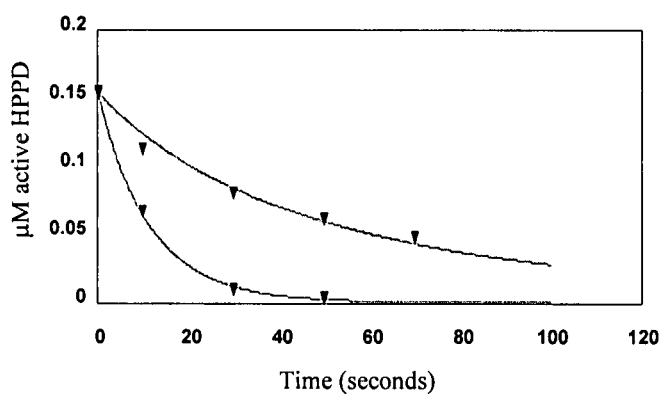

Figure 5. Binding of $^{14}$C mesotrione to *Arabidopsis* HPPD
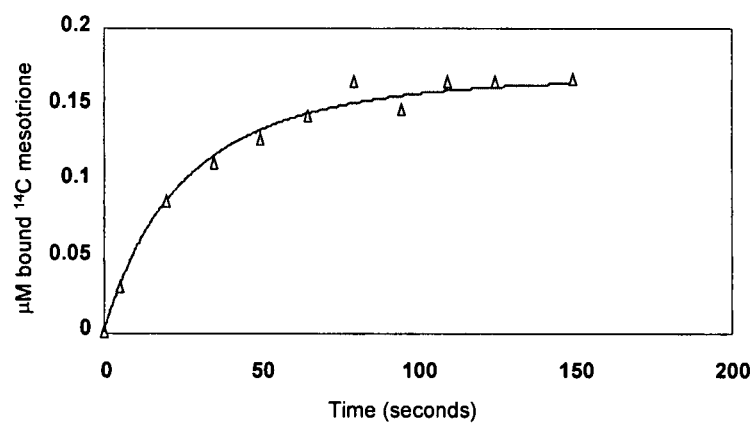

SEQUENCE LISTING

<160> NUMBER OF SEQ ID NOS: 41

<210> SEQ ID NO 1
<211> LENGTH: 1074
<212> TYPE: DNA
<213> ORGANISM: Pseudomonas fluorescens

<400> SEQUENCE: 1

```
atggccgacc aatacgaaaa cccaatgggc ctgatgggct ttgaatttat tgaattcgca      60
tcgccgactc cgggcaccct ggagccgatc ttcgagatca tgggcttcac caaagtcgcg     120
acccaccgct ccaagaatgt gcacctgtac cgccagggcg agatcaacct gatcctcaac     180
aaccagcccg acagcctggc ctcgtacttc gccgccgaac acggcccttc ggtgtgcggc     240
atggcgttcc gggtcaaaga ctcgcagcag gcttacaacc gcgcgttgga actgggcgcc     300
cagccgattc atatcgaaac cggcccgatg gaactcaacc tgccggccat caagggcatc     360
ggcggtgcgc cgctgtacct gatcgaccgc ttcggtgaag gcagctcgat atatgacatc     420
gacttcgtgt acctcgaagg tgtcgaccgc aacccggtag gcgcgggcct caaggtcatc     480
gaccacctga cccacaacgt gtatcgcggc cgcatggcct actgggccaa cttctacgag     540
aaactgttca acttccgtga agcacgctac ttcgatatca agggcgaata caccggcctt     600
acgtccaagg ccatgagtgc cccggacggc atgatccgca tcccgctgaa cgaggaatcg     660
tccaagggcg ccggccagat cgaagagttc ctgatgcagt tcaacggcga gggcatccag     720
cacgtggcgt tcctcaccga agacctggtc aagacctggg atgcgttgaa gaagatcggc     780
atgcgcttca tgaccgcgcc gccggacacc tactacgaaa tgctcgaagg ccgcctgcca     840
```

```
aaccacggcg agccggtgga ccaactgcag gcgcgcggta ttttgctgga cggctcctcg   900
atcgagggcg acaagcgcct gctgctgcag atcttctcgg aaaccctgat gggcccggtg   960
ttcttcgaat tcatccagcg caaaggcgac gatgggtttg gcgagggcaa cttcaaggcg  1020
ctgttcgagt cgatcgagcg cgaccaggta cgtcgcggtg tactgaccac cgac         1074
```

<210> SEQ ID NO 2
<211> LENGTH: 358
<212> TYPE: PRT
<213> ORGANISM: Pseudomonas fluorescens

<400> SEQUENCE: 2

```
Met Ala Asp Gln Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Gln Pro Asp
    50                  55                  60

Ser Leu Ala Ser Tyr Phe Ala Ala Glu His Pro Ser Val Cys Gly
65                  70                  75                  80

Met Ala Phe Arg Val Lys Asp Ser Gln Gln Ala Tyr Asn Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Asp Arg Asn Pro Val Gly Ala Gly Leu Lys Val Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Glu Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Asp Gln
        275                 280                 285

Leu Gln Ala Arg Gly Ile Leu Leu Asp Gly Ser Ser Ile Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
```

Gly Val Leu Thr Thr Asp
            355

<210> SEQ ID NO 3
<211> LENGTH: 1323
<212> TYPE: DNA
<213> ORGANISM: Avena sativa

<400> SEQUENCE: 3

```
atgccgccca ccccgccac cgccaccggc gccgccgcgg ccgccgtgac tccagagcac      60
gcggcccgga gctttccccg agtggtccgc gtcaacccgc gcagcgaccg cttcccgtg     120
ctctccttcc accacgtcga gctctggtgc gccgacgccg cctcagcggc cggacgcttc    180
tccttcgcgc tcggcgcgcc gctcgccgcc cggtccgacc tctccacggg gaactccgcg    240
cacgcctccc tcctgctccg ctcgggcgcc ctcgccttcc tcttcacggc gccctacgcg    300
ccgccgccgc aggaggccgc cacggccgca gccaccgcct ccatccctc cttctccgcc    360
gacgccgcgc ggacgttcgc cgccgcccac ggcctcgcgg tgcgctccgt cggggtccgc    420
gtcgctgacg ccgccgaggc cttccgcgtc agcgtagccg gcggcgctcg cccggccttc    480
gccccagccg acctcggcca tggcttcggc ctcgccgagg tcgagctcta cggcgacgtc    540
gtgctacgct tcgtcagcta cccggacgag acagacctgc cattcctgcc agggttcgag    600
cgcgtgagca gccccggcgc cgtggactac ggcctcacgc ggttcgacca cgtcgtgggc    660
aacgtcccgg agatggcccc ggtcatagac tacatgaaag gcttcttggg gttccacgag    720
ttcgccgagt tcaccgccga ggacgtgggc acgaccgaga gcgggctcaa ctcggtggtg    780
ctcgccaaca actccgaggc cgtgctgctg ccgtcaacg agcccgtgca cggcacaaag    840
cgacggagcc agatacagac gtacctggag tatcacggcg ggcccggcgt gcagcacatc    900
gcgctcgcca gcaacgacgt gctcaggacg ctcaggagaa tgcgggcgcg cacgcccatg    960
ggcggcttcg agttcatggc gccaccgcag gcgaaatact atgaaggcgt gcggcgcatc   1020
gcaggtgacg tgctctcgga agagcagatc aaggaatgcc aggagctggg ggtgctagtc   1080
gacagggatg atcaaggggt gttgctccaa atcttcacca agccagtagg ggacaggcca   1140
acgttttttcc tggagatgat ccaaagaatc gggtgcatgg agaaggacga ggtcgggcaa   1200
gagtaccaga agggtggctg cggcgggttt ggcaagggca tttctccga gctgttcaag    1260
tccattgagg actatgagaa atcccttgag gtcaagcaat ctgttgtagc tcagaaatcc    1320
tag                                                                 1323
```

<210> SEQ ID NO 4
<211> LENGTH: 440
<212> TYPE: PRT
<213> ORGANISM: Avena sativa

<400> SEQUENCE: 4

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala

```
            65                  70                  75                  80
His Ala Ser Leu Leu Arg Ser Gly Ala Leu Ala Phe Leu Phe Thr
                    85                  90                  95

Ala Pro Tyr Ala Pro Pro Gln Glu Ala Thr Ala Ala Thr
                100                 105                 110

Ala Ser Ile Pro Ser Phe Ser Ala Asp Ala Ala Arg Thr Phe Ala Ala
                115                 120                 125

Ala His Gly Leu Ala Val Arg Ser Val Gly Val Arg Val Ala Asp Ala
            130                 135                 140

Ala Glu Ala Phe Arg Val Ser Val Ala Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
                180                 185                 190

Leu Pro Phe Leu Pro Gly Phe Glu Arg Val Ser Ser Pro Gly Ala Val
            195                 200                 205

Asp Tyr Gly Leu Thr Arg Phe Asp His Val Val Gly Asn Val Pro Glu
        210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
        275                 280                 285

Leu Glu Tyr His Gly Gly Pro Gly Val Gln His Ile Ala Leu Ala Ser
    290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Glu Ile Lys Glu
            340                 345                 350

Cys Gln Glu Leu Gly Val Leu Val Asp Arg Asp Gln Gly Val Leu
        355                 360                 365

Leu Gln Ile Phe Thr Lys Pro Val Gly Asp Arg Pro Thr Phe Phe Leu
    370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Val Lys
            420                 425                 430

Gln Ser Val Val Ala Gln Lys Ser
        435                 440

<210> SEQ ID NO 5
<211> LENGTH: 433
<212> TYPE: PRT
<213> ORGANISM: Triticum sp.

<400> SEQUENCE: 5

Met Pro Pro Thr Pro Thr Thr Pro Ala Ala Thr Gly Ala Ala Ala Val
```

-continued

```
1               5               10              15
Thr Pro Glu His Ala Arg Pro Arg Met Val Arg Phe Asn Pro Arg
                20              25              30

Ser Asp Arg Phe His Thr Leu Ala Phe His His Val Glu Phe Trp Cys
        35              40              45

Ala Asp Ala Ala Ser Ala Ala Gly Arg Phe Ala Phe Ala Leu Gly Ala
50              55              60

Pro Leu Ala Ala Arg Ser Asp Leu Ser Thr Gly Asn Ser Val His Ala
65              70              75              80

Ser Gln Leu Leu Arg Ser Gly Asn Leu Ala Phe Leu Phe Thr Ala Pro
                85              90              95

Tyr Ala Asn Gly Cys Asp Ala Ala Thr Ala Ser Leu Pro Ser Phe Ser
                100             105             110

Ala Asp Ala Ala Arg Gln Phe Ser Ala Asp His Gly Leu Ala Val Arg
                115             120             125

Ser Ile Ala Leu Arg Val Ala Asp Ala Ala Glu Ala Phe Arg Ala Ser
                130             135             140

Val Asp Gly Gly Ala Arg Pro Ala Phe Ser Pro Val Asp Leu Gly Arg
145             150             155             160

Gly Phe Gly Phe Ala Glu Val Glu Leu Tyr Gly Asp Val Val Leu Arg
                165             170             175

Phe Val Ser His Pro Asp Gly Arg Asp Val Pro Phe Leu Pro Gly Phe
                180             185             190

Glu Gly Val Ser Asn Pro Asp Ala Val Asp Tyr Gly Leu Thr Arg Phe
                195             200             205

Asp His Val Val Gly Asn Val Pro Glu Leu Ala Pro Ala Ala Ala Tyr
                210             215             220

Val Ala Gly Phe Thr Gly Phe His Glu Phe Ala Glu Phe Thr Thr Glu
225             230             235             240

Asp Val Gly Thr Ala Glu Ser Gly Leu Asn Ser Met Val Leu Ala Asn
                245             250             255

Asn Ser Glu Gly Val Leu Leu Pro Leu Asn Glu Pro Val His Gly Thr
                260             265             270

Lys Arg Arg Ser Gln Ile Gln Thr Phe Leu Glu His His Gly Gly Ser
                275             280             285

Gly Val Gln His Ile Ala Val Ala Ser Ser Asp Val Leu Arg Thr Leu
                290             295             300

Arg Glu Met Arg Ala Arg Ser Ala Met Gly Gly Phe Asp Phe Leu Pro
305             310             315             320

Pro Pro Leu Pro Lys Tyr Tyr Glu Gly Val Arg Arg Ile Ala Gly Asp
                325             330             335

Val Leu Ser Glu Ala Gln Ile Lys Glu Cys Gln Glu Leu Gly Val Leu
                340             345             350

Val Asp Arg Asp Asp Gln Gly Val Leu Leu Gln Ile Phe Thr Lys Pro
                355             360             365

Val Gly Asp Arg Pro Thr Leu Phe Leu Glu Met Ile Gln Arg Ile Gly
                370             375             380

Cys Met Glu Lys Asp Glu Arg Gly Glu Glu Tyr Gln Lys Gly Gly Cys
385             390             395             400

Gly Gly Phe Gly Lys Gly Asn Phe Ser Glu Leu Phe Lys Ser Ile Glu
                405             410             415

Asp Tyr Glu Lys Ser Leu Glu Ala Lys Gln Ser Ala Ala Val Gln Gly
                420             425             430
```

<210> SEQ ID NO 6
<211> LENGTH: 1302
<212> TYPE: DNA
<213> ORGANISM: Triticum sp.

<400> SEQUENCE: 6

| | | | | | |
|---|---|---|---|---|---|
| atgccgccca | ccccaccac | ccccgcagcc | accggcgccg | ccgcggtgac | gccggagcac | 60 |
| gcgcggccgc | gccgaatggt | ccgcttcaac | ccgcgcagcg | accgcttcca | cacgctcgcc | 120 |
| ttccaccacg | tcgagttctg | gtgcgcggac | gccgcctccg | ccgccggccg | cttcgccttc | 180 |
| gcgctcggcg | cgccgctcgc | cgccaggtcc | gacctctcca | cggggaactc | cgtgcacgcc | 240 |
| tcccagctgc | tccgctcggg | caacctcgcc | ttcctcttca | cggcccccta | cgccaacggc | 300 |
| tgcgacgccg | ccaccgcctc | cctgccctcc | ttctccgccg | acgccgcgcg | ccagttctcc | 360 |
| gcggaccacg | gcctcgcggt | gcgctccata | gcgctgcgcg | tcgcggacgc | tgccgaggcc | 420 |
| ttccgcgcca | gcgtcgacgg | gggcgcgcgc | ccggccttca | gccctgtgga | cctcggccgc | 480 |
| ggcttcggct | tcgcggaggt | cgagctctac | ggcgacgtcg | tgctccgctt | cgtcagccac | 540 |
| ccggacggca | gggacgtgcc | cttcttgccg | gggttcgagg | gcgtgagcaa | cccagacgcc | 600 |
| gtggactacg | gcctgacgcg | gttcgaccac | gtcgtcggca | acgtcccgga | gcttgccccc | 660 |
| gccgcggcct | acgtcgccgg | gttcacgggg | ttccacgagt | tcgccgagtt | cacgacggag | 720 |
| gacgtgggca | cggccgagag | cgggctcaac | tcgatggtgc | tcgccaacaa | ctcggagggc | 780 |
| gtgctgctgc | cgctcaacga | gccggtgcac | ggcaccaagc | gccggagcca | gatacagacg | 840 |
| ttcctggaac | accacggcgg | ctcgggcgtg | cagcacatcg | cggtggccag | cagcgacgtg | 900 |
| ctcaggacgc | tcagggagat | gcgtgcgcgc | tccgccatgg | gcggcttcga | cttcctgcca | 960 |
| ccccgctgc | cgaagtacta | cgaaggcgtg | cggcgcatcg | ccggggatgt | gctctcggag | 1020 |
| gcgcagatca | aggaatgcca | ggagctgggg | gtgctcgtcg | acaggacga | ccaagggtg | 1080 |
| ttgctacaaa | tcttcaccaa | gccagtaggg | gacaggccga | cgttgttcct | ggagatgatc | 1140 |
| cagaggatcg | ggtgcatgga | gaaggacgag | agagggaag | agtaccagaa | gggtggctgc | 1200 |
| ggcgggttcg | gcaaaggcaa | cttctccgag | ctgttcaagt | ccattgaaga | ttacgagaag | 1260 |
| tcccttgaag | ccaagcaatc | tgctgcagtt | cagggatcat | ag | | 1302 |

<210> SEQ ID NO 7
<211> LENGTH: 444
<212> TYPE: DNA
<213> ORGANISM: Brachiaria platyphylla

<400> SEQUENCE: 7

| | | | | | |
|---|---|---|---|---|---|
| gagccggtgc | wcggcaccaa | gcgccgsagc | cagatacaga | cgttcctgga | gcaccacggc | 60 |
| ggcccsggcg | tgcagcacat | cgcgctggcc | agcgacgayg | tgctcaggac | gctgcgggag | 120 |
| atgcaggcgc | gctccgccat | gggcgggttc | gagttcatgs | yggctccgcm | gcccgastac | 180 |
| taygacggyg | tsrggcggcg | cgccggggac | gtgctctcgg | aggagcagat | targgagtgc | 240 |
| caggaattgg | gggtgctggt | ggacagggat | gaccaggggg | tgttgctcca | aatcttcacc | 300 |
| aagccagtgg | gggacaggcc | aacatttttc | ttagagataa | tccaaaggat | tgggtgcatg | 360 |
| gagaaggatg | agaaggggca | ggaataccag | aagggtggct | gcggcggctt | tggaaaggga | 420 |
| aacttctccc | agctgwtcaa | gwcc | | | | 444 |

<210> SEQ ID NO 8

```
<211> LENGTH: 148
<212> TYPE: PRT
<213> ORGANISM: Brachiaria platyphylla
<220> FEATURE:
<221> NAME/KEY: MISC_FEATURE
<222> LOCATION: (4)..(4)
<223> OTHER INFORMATION: X is any amino acid
<220> FEATURE:
<221> NAME/KEY: MISC_FEATURE
<222> LOCATION: (54)..(54)
<223> OTHER INFORMATION: Xaa is any amino acid
<220> FEATURE:
<221> NAME/KEY: MISC_FEATURE
<222> LOCATION: (57)..(57)
<223> OTHER INFORMATION: Xaa is any amino acid
<220> FEATURE:
<221> NAME/KEY: MISC_FEATURE
<222> LOCATION: (59)..(59)
<223> OTHER INFORMATION: Xaa is any amino acid
<220> FEATURE:
<221> NAME/KEY: MISC_FEATURE
<222> LOCATION: (65)..(65)
<223> OTHER INFORMATION: Xaa is any amino acid
<220> FEATURE:
<221> NAME/KEY: MISC_FEATURE
<222> LOCATION: (78)..(78)
<223> OTHER INFORMATION: Xaa is any amino acid
<220> FEATURE:
<221> NAME/KEY: MISC_FEATURE
<222> LOCATION: (146)..(146)
<223> OTHER INFORMATION: Xaa is any amino acid
<220> FEATURE:
<221> NAME/KEY: MISC_FEATURE
<222> LOCATION: (148)..(148)
<223> OTHER INFORMATION: Xaa is any amino acid

<400> SEQUENCE: 8

Glu Pro Val Xaa Gly Thr Lys Arg Arg Ser Gln Ile Gln Thr Phe Leu
1               5                   10                  15

Glu His His Gly Gly Pro Gly Val Gln His Ile Ala Leu Ala Ser Asp
            20                  25                  30

Asp Val Leu Arg Thr Leu Arg Glu Met Gln Ala Arg Ser Ala Met Gly
        35                  40                  45

Gly Phe Glu Phe Met Xaa Ala Pro Xaa Pro Xaa Tyr Tyr Asp Gly Val
    50                  55                  60

Xaa Arg Arg Ala Gly Asp Val Leu Ser Glu Glu Gln Ile Xaa Glu Cys
65                  70                  75                  80

Gln Glu Leu Gly Val Leu Val Asp Arg Asp Gln Gly Val Leu Leu
                85                  90                  95

Gln Ile Phe Thr Lys Pro Val Gly Asp Arg Pro Thr Phe Phe Leu Glu
            100                 105                 110

Ile Ile Gln Arg Ile Gly Cys Met Glu Lys Asp Glu Lys Gly Gln Glu
        115                 120                 125

Tyr Gln Lys Gly Gly Cys Gly Gly Phe Gly Lys Gly Asn Phe Ser Gln
    130                 135                 140

Leu Xaa Lys Xaa
145

<210> SEQ ID NO 9
<211> LENGTH: 444
<212> TYPE: DNA
<213> ORGANISM: Cenchrus echinatus

<400> SEQUENCE: 9
gagccggtgc acggcaccaa gcgccgcagc cagattcaga cgttcctgga ccacaacggc      60
ggccctggcg tgcagcacat cgcgctggcc agcgacgacg tgctcaggac gctgcgggag     120
```

-continued

```
atgcaagcac gctcygccay gggcggrttc gagttcatgg cgcctccrcc gcccgagtac    180
tacgaaggtg tgaggcggcg cgcgggsgac gtgctctcgg aggctcagat taaagagtgc    240
caggaactgg gtgtgctggt ggacagggat gaccagggg tgttgctcca aatcttcacc     300
aagccagtgg gggacaggca acattgttc ttggagataa tccaaaggat tgggtgcatg     360
gagaaggayg agcaggggcg ggaataccag aagggcggtt gcggcggcty tggaaaggga    420
aacttctcsc agctgwtcaa gwcc                                            444
```

<210> SEQ ID NO 10
<211> LENGTH: 148
<212> TYPE: PRT
<213> ORGANISM: Cenchrus echinatus
<220> FEATURE:
<221> NAME/KEY: MISC_FEATURE
<222> LOCATION: (47)..(47)
<223> OTHER INFORMATION: Xaa is any amino acid
<220> FEATURE:
<221> NAME/KEY: MISC_FEATURE
<222> LOCATION: (137)..(137)
<223> OTHER INFORMATION: Xaa is any amino acid
<220> FEATURE:
<221> NAME/KEY: MISC_FEATURE
<222> LOCATION: (146)..(146)
<223> OTHER INFORMATION: Xaa is any amino acid
<220> FEATURE:
<221> NAME/KEY: MISC_FEATURE
<222> LOCATION: (148)..(148)
<223> OTHER INFORMATION: Xaa is any amino acid

<400> SEQUENCE: 10

```
Glu Pro Val His Gly Thr Lys Arg Arg Ser Gln Ile Gln Thr Phe Leu
1               5                   10                  15

Asp His Asn Gly Gly Pro Gly Val Gln His Ile Ala Leu Ala Ser Asp
            20                  25                  30

Asp Val Leu Arg Thr Leu Arg Glu Met Gln Ala Arg Ser Ala Xaa Gly
        35                  40                  45

Gly Phe Glu Phe Met Ala Pro Pro Pro Glu Tyr Tyr Glu Gly Val
    50                  55                  60

Arg Arg Arg Ala Gly Asp Val Leu Ser Glu Ala Gln Ile Lys Glu Cys
65                  70                  75                  80

Gln Glu Leu Gly Val Leu Val Asp Arg Asp Gln Gly Val Leu Leu
                85                  90                  95

Gln Ile Phe Thr Lys Pro Val Gly Asp Arg Gln Thr Leu Phe Leu Glu
            100                 105                 110

Ile Ile Gln Arg Ile Gly Cys Met Glu Lys Asp Glu Gly Arg Glu
        115                 120                 125

Tyr Gln Lys Gly Gly Cys Gly Gly Xaa Gly Lys Gly Asn Phe Ser Gln
    130                 135                 140

Leu Xaa Lys Xaa
145
```

<210> SEQ ID NO 11
<211> LENGTH: 444
<212> TYPE: DNA
<213> ORGANISM: Lolium rigidum

<400> SEQUENCE: 11

```
gagccggtgc acggcaccwa gcgccgcagc cagattcaga cctacctcga ctaccacggc    60
gggcccggcg tgcagcacat cgcgctmgcc agtagcgatg tgctcaggac gctcagggag   120
atgcgsgcgc gcacgcccat gggcggcttc gagttcatgg cgccgccgca ggccaaatac   180
```

```
tacgatggyg tgcggcgyat cgcggggggat gtgctctcgg argagcagat caaggaatgc      240
caggagctcg gggtgctcgt cgacagggat gaccaagggg tgctgctaca aatcttcacc      300
aagccagtkg grgacaggcc aacgtttttc ctggagatga tmcaaagaat cgggtgcatg      360
gagaaggayg aggtcgggca agagtaccag aagggtggct gcggyggggtt tggcaagggc      420 aacttctccg agctgtwcaw gtcc                                             444
```

<210> SEQ ID NO 12
<211> LENGTH: 148
<212> TYPE: PRT
<213> ORGANISM: Lolium rigidum
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (146)..(147)
<223> OTHER INFORMATION: Xaa is any amino acid

<400> SEQUENCE: 12

```
Glu Pro Val His Gly Thr Xaa Arg Arg Ser Gln Ile Gln Thr Tyr Leu
1               5                   10                  15

Asp Tyr His Gly Gly Pro Gly Val Gln His Ile Ala Leu Ala Ser Ser
                20                  25                  30

Asp Val Leu Arg Thr Leu Arg Glu Met Arg Ala Arg Thr Pro Met Gly
            35                  40                  45

Gly Phe Glu Phe Met Ala Pro Pro Gln Ala Lys Tyr Tyr Asp Gly Val
        50                  55                  60

Arg Arg Ile Ala Gly Asp Val Leu Ser Glu Glu Gln Ile Lys Glu Cys
65                  70                  75                  80

Gln Glu Leu Gly Val Leu Val Asp Arg Asp Asp Gln Gly Val Leu Leu
                85                  90                  95

Gln Ile Phe Thr Lys Pro Val Gly Asp Arg Pro Thr Phe Phe Leu Glu
            100                 105                 110

Met Ile Gln Arg Ile Gly Cys Met Glu Lys Asp Glu Val Gly Gln Glu
        115                 120                 125

Tyr Gln Lys Gly Gly Cys Gly Gly Phe Gly Lys Gly Asn Phe Ser Glu
    130                 135                 140

Leu Xaa Xaa Ser
145
```

<210> SEQ ID NO 13
<211> LENGTH: 444
<212> TYPE: DNA
<213> ORGANISM: Festuca arundinacea

<400> SEQUENCE: 13

```
gagccggwgc acggcaccaa gcgccgcagc cagatacaga cctacctcga ctaccacggc       60
gggcccggcg tgcagcacat cgcgctcgcc agcascgacg tgctcaggac gctcagggag      120
atgcgggcgc gcacgcccat gggcggcttc gagttcatgg cgccrccgca ggcsaaatac      180
tacgawggcg tgcggcgcat cgcrggsgat gtgctctcsg aagagcagat caaggaatgc      240
caggagctsg gggtgctcgt cgacagggat gaccaagggg tgytgctmca aatcttcacc      300
aagccagtgg gagacaggcc aacgtttttc ctsgagatga tacaaagaat cgggtgcatg      360
gagaaggayg aggtcgggca agagtaccag aagggtggct gcggtggctt tggcaagggm      420
aacttctccc agctgttcwa gtcc                                             444
```

<210> SEQ ID NO 14
<211> LENGTH: 148
<212> TYPE: PRT
<213> ORGANISM: Festuca arundinacea
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (32)..(32)
<223> OTHER INFORMATION: Xaa is any amino acid
<220> FEATURE:
<221> NAME/KEY: MISC_FEATURE
<222> LOCATION: (62)..(62)
<223> OTHER INFORMATION: Xaa is any amino acid
<220> FEATURE:
<221> NAME/KEY: MISC_FEATURE
<222> LOCATION: (147)..(147)
<223> OTHER INFORMATION: Xaa is any amino acid

<400> SEQUENCE: 14

Glu Pro Xaa His Gly Thr Lys Arg Arg Ser Gln Ile Gln Thr Tyr Leu
1               5                   10                  15

Asp Tyr His Gly Gly Pro Gly Val Gln His Ile Ala Leu Ala Ser Xaa
            20                  25                  30

Asp Val Leu Arg Thr Leu Arg Glu Met Arg Ala Arg Thr Pro Met Gly
        35                  40                  45

Gly Phe Glu Phe Met Ala Pro Pro Gln Ala Lys Tyr Tyr Xaa Gly Val
    50                  55                  60

Arg Arg Ile Ala Gly Asp Val Leu Ser Glu Glu Gln Ile Lys Glu Cys
65                  70                  75                  80

Gln Glu Leu Gly Val Leu Val Asp Arg Asp Asp Gln Gly Val Leu Leu
                85                  90                  95

Gln Ile Phe Thr Lys Pro Val Gly Asp Arg Pro Thr Phe Phe Leu Glu
            100                 105                 110

Met Ile Gln Arg Ile Gly Cys Met Glu Lys Asp Glu Val Gly Gln Glu
        115                 120                 125

Tyr Gln Lys Gly Gly Cys Gly Gly Phe Gly Lys Gly Asn Phe Ser Gln
    130                 135                 140

Leu Phe Xaa Ser
145

<210> SEQ ID NO 15
<211> LENGTH: 444
<212> TYPE: DNA
<213> ORGANISM: Setaria faberi

<400> SEQUENCE: 15
gagccggtgc tcggcaccat gcgccgcagc cagatacaga cgttcctgga ccacaacggc      60
ggccccggcg tgcagcacat cgcgctggcc agcgacgacg tgctcaggac gctgcgggag     120
atgcaagcac gctcagccat gggcggattc gagttcatgg cggctccacc gcccgactat     180
tacgaaggtg tgaggcggcg cgccggggac gtgctctcgg aggcycagat taaggagtgc     240
caggaactgg gggtgctggt ggacagggat gaccagggg tgttgctcca atcttcacc       300 aagccagtgg gggacaggca acattgttc ttggagataa tacaaaggat tgggtgcatg      360
gagaaggacg agcaggggca ggaataccag aagggtggtt gtggcggttt tggaargggga    420 aacttctccc agcwgwtcaa gtcc                                             444

<210> SEQ ID NO 16

-continued

```
<211> LENGTH: 148
<212> TYPE: PRT
<213> ORGANISM: Setaria faberi
<220> FEATURE:
<221> NAME/KEY: MISC_FEATURE
<222> LOCATION: (139)..(139)
<223> OTHER INFORMATION: Xaa is any amino acid
<220> FEATURE:
<221> NAME/KEY: MISC_FEATURE
<222> LOCATION: (145)..(146)
<223> OTHER INFORMATION: Xaa is any amino acid

<400> SEQUENCE: 16
```

Glu Pro Val Leu Gly Thr Met Arg Arg Ser Gln Ile Gln Thr Phe Leu
1               5                   10                  15

Asp His Asn Gly Gly Pro Gly Val Gln His Ile Ala Leu Ala Ser Asp
            20                  25                  30

Asp Val Leu Arg Thr Leu Arg Glu Met Gln Ala Arg Ser Ala Met Gly
        35                  40                  45

Gly Phe Glu Phe Met Ala Ala Pro Pro Asp Tyr Tyr Glu Gly Val
    50                  55                  60

Arg Arg Arg Ala Gly Asp Val Leu Ser Glu Ala Gln Ile Lys Glu Cys
65                  70                  75                  80

Gln Glu Leu Gly Val Leu Val Asp Arg Asp Gln Gly Val Leu Leu
                85                  90                  95

Gln Ile Phe Thr Lys Pro Val Gly Asp Arg Gln Thr Leu Phe Leu Glu
            100                 105                 110

Ile Ile Gln Arg Ile Gly Cys Met Glu Lys Asp Glu Gln Gly Gln Glu
        115                 120                 125

Tyr Gln Lys Gly Gly Cys Gly Gly Phe Gly Xaa Gly Asn Phe Ser Gln
    130                 135                 140

Xaa Xaa Lys Ser
145

```
<210> SEQ ID NO 17
<211> LENGTH: 444
<212> TYPE: DNA
<213> ORGANISM: Eleusine indica
<400> SEQUENCE: 17
gagccggtgc tcggcaccat gcgccgcagc cagatacaga cgtacctgga ccaccacggt    60
ggccccggcg tgcagcacat ggcgctggcc agcgacgacg tgctcaggac gctcagggag   120
atgcgggccc gctccgccat gggcgggttc gagttcctcg cgccgccgcc gccaaactac   180
tacgacggtg tcaggcggcg cgccggggac gtgctctcgg agcagcagat aaaggagtgc   240
caggagctgg gcgtgctggt ggacagggat gaccagggcg tgttgcttca atcttcacc    300 aagccagtgg agacaggcc aacactgttc ttggagataa tccaaaggat cgggtgcatg   360
gagaaggatg agcgtgggca agagtaccag aaaggcggct gtggcggttt tggcaagggc   420
aacttctccc agctgttcta gtcc                                         444

<210> SEQ ID NO 18
<211> LENGTH: 146
<212> TYPE: PRT
<213> ORGANISM: Eleusine indica

<400> SEQUENCE: 18
```

Glu Pro Val Leu Gly Thr Met Arg Arg Ser Gln Ile Gln Thr Tyr Leu
1               5                   10                  15

Asp His His Gly Gly Pro Gly Val Gln His Met Ala Leu Ala Ser Asp

Asp Val Leu Arg Thr Leu Arg Glu Met Arg Ala Arg Ser Ala Met Gly
            35                  40                  45

Gly Phe Glu Phe Leu Ala Pro Pro Pro Asn Tyr Tyr Asp Gly Val
        50                  55                  60

Arg Arg Arg Ala Gly Asp Val Leu Ser Glu Gln Gln Ile Lys Glu Cys
 65                  70                  75                  80

Gln Glu Leu Gly Val Leu Val Asp Arg Asp Gln Gly Val Leu Leu
                85                  90                  95

Gln Ile Phe Thr Lys Pro Val Gly Asp Arg Pro Thr Leu Phe Leu Glu
            100                 105                 110

Ile Ile Gln Arg Ile Gly Cys Met Glu Lys Asp Glu Arg Gly Gln Glu
            115                 120                 125

Tyr Gln Lys Gly Gly Cys Gly Gly Phe Gly Lys Gly Asn Phe Ser Gln
            130                 135                 140

Leu Phe
145

<210> SEQ ID NO 19
<211> LENGTH: 444
<212> TYPE: DNA
<213> ORGANISM: Sorghum sp.

<400> SEQUENCE: 19
gagccggtgc acggcaccwa gcgccgcagc cagatacaga cgttcttgga ccaccacggc      60
ggccccggcg tgcagcacat ggcgctggcc agcgacgacg tgctcagaac gctgagggag     120
atgcaggcgc gctcggccat gggcggcttc gagttcatgg cgcctccggc gcccgaatac     180
tatgacggcg tgaggcggcg cgccggggac gtgctcacgg aggcgcagat taaggagtgt     240
caggaactag gggtgctggt ggacagagat gaccagggcg tgctgctcca gatcttcacc     300
aagccagtgg gggacaggcc aacgttgttc ttggagatca ttcaaaggat cgggtgcatg     360
gagaaggatg agaaggggca agaataccag aagggtggct gtggcgggtt tggcaaggga     420
aacttctccc agctgwtcwa gtcc                                            444

<210> SEQ ID NO 20
<211> LENGTH: 148
<212> TYPE: PRT
<213> ORGANISM: Sorghum sp.
<220> FEATURE:
<221> NAME/KEY: MISC_FEATURE
<222> LOCATION: (7)..(7)
<223> OTHER INFORMATION: Xaa is any amino acid
<220> FEATURE:
<221> NAME/KEY: MISC_FEATURE
<222> LOCATION: (146)..(147)
<223> OTHER INFORMATION: Xaa is any amino acid

<400> SEQUENCE: 20

Glu Pro Val His Gly Thr Xaa Arg Arg Ser Gln Ile Gln Thr Phe Leu
 1               5                  10                  15

Asp His His Gly Gly Pro Gly Val Gln His Met Ala Leu Ala Ser Asp
            20                  25                  30

Asp Val Leu Arg Thr Leu Arg Glu Met Gln Ala Arg Ser Ala Met Gly
            35                  40                  45

Gly Phe Glu Phe Met Ala Pro Pro Ala Pro Glu Tyr Tyr Asp Gly Val
        50                  55                  60

Arg Arg Arg Ala Gly Asp Val Leu Thr Glu Ala Gln Ile Lys Glu Cys
 65                  70                  75                  80

-continued

```
Gln Glu Leu Gly Val Leu Val Asp Arg Asp Asp Gln Gly Val Leu Leu
                85                  90                  95

Gln Ile Phe Thr Lys Pro Val Gly Asp Arg Pro Thr Leu Phe Leu Glu
            100                 105                 110

Ile Ile Gln Arg Ile Gly Cys Met Glu Lys Asp Glu Lys Gly Gln Glu
        115                 120                 125

Tyr Gln Lys Gly Gly Cys Gly Gly Phe Gly Lys Gly Asn Phe Ser Gln
    130                 135                 140

Leu Xaa Xaa Ser
145

<210> SEQ ID NO 21
<211> LENGTH: 25
<212> TYPE: DNA
<213> ORGANISM: Artificial Sequence
<220> FEATURE:
<223> OTHER INFORMATION: Primer HPPD RT2

<400> SEQUENCE: 21
cgcaccagar ctcsacgtgg tggaa                                          25

<210> SEQ ID NO 22
<211> LENGTH: 25
<212> TYPE: DNA
<213> ORGANISM: Artificial Sequence
<220> FEATURE:
<223> OTHER INFORMATION: Primer HPPD RT4

<400> SEQUENCE: 22
cgacgtcgcc gtagagctcg acctc                                          25

<210> SEQ ID NO 23
<211> LENGTH: 47
<212> TYPE: DNA
<213> ORGANISM: Artificial Sequence
<220> FEATURE:
<223> OTHER INFORMATION: Primer DT30

<400> SEQUENCE: 23
gagagaggat cctcgagttt tttttttttt tttttttttt tttttt                   47

<210> SEQ ID NO 24
<211> LENGTH: 24
<212> TYPE: DNA
<213> ORGANISM: Artificial Sequence
<220> FEATURE:
<223> OTHER INFORMATION: Primer HPPD3

<400> SEQUENCE: 24
aayttctccg agctgttcaa gtcc                                           24

<210> SEQ ID NO 25
<211> LENGTH: 27
<212> TYPE: DNA
<213> ORGANISM: Artificial Sequence
<220> FEATURE:
<223> OTHER INFORMATION: Primer DTR

<400> SEQUENCE: 25
aggttttaac gagagaggat cctcgag                                        27

<210> SEQ ID NO 26
<211> LENGTH: 37
<212> TYPE: DNA
```

```
<213> ORGANISM: Artificial Sequence
<220> FEATURE:
<223> OTHER INFORMATION: Primer AvesaI

<400> SEQUENCE: 26
acttgacata tgccgcccac ccccgccacc gccaccg                          37

<210> SEQ ID NO 27
<211> LENGTH: 39
<212> TYPE: DNA
<213> ORGANISM: Artificial Sequence
<220> FEATURE:
<223> OTHER INFORMATION: Primer Avesa

<400> SEQUENCE: 27
ttacgtggat ccctaggatt tctgagctac aacagattg                        39

<210> SEQ ID NO 28
<211> LENGTH: 23
<212> TYPE: DNA
<213> ORGANISM: Artificial Sequence
<220> FEATURE:
<223> OTHER INFORMATION: Primer TAHPPDNde

<400> SEQUENCE: 28
aacacaccat atgccgccca ccc                                         23

<210> SEQ ID NO 29
<211> LENGTH: 25
<212> TYPE: DNA
<213> ORGANISM: Artificial Sequence
<220> FEATURE:
<223> OTHER INFORMATION: Primer TSHPPDSph

<400> SEQUENCE: 29
aacacacagc atgccgccca ccccc                                       25

<210> SEQ ID NO 30
<211> LENGTH: 32
<212> TYPE: DNA
<213> ORGANISM: Artificial Sequence
<220> FEATURE:
<223> OTHER INFORMATION: Primer TAHPPDBam

<400> SEQUENCE: 30
ggatcctatg atccctgaac tgcagcagat tg                               32

<210> SEQ ID NO 31
<211> LENGTH: 21
<212> TYPE: DNA
<213> ORGANISM: Artificial Sequence
<220> FEATURE:
<223> OTHER INFORMATION: Primer HPPD4R

<400> SEQUENCE: 31
ggacttgaac agctssgaga a                                           21

<210> SEQ ID NO 32
<211> LENGTH: 21
<212> TYPE: DNA
<213> ORGANISM: Artificial Sequence
<220> FEATURE:
<223> OTHER INFORMATION: Primer HPPD5

<400> SEQUENCE: 32
gagccggtgc acggcaccaa g                                           21
```

<210> SEQ ID NO 33
<211> LENGTH: 6
<212> TYPE: PRT
<213> ORGANISM: Motif

<400> SEQUENCE: 33

Gln Ile Lys Glu Cys Gln
1               5

<210> SEQ ID NO 34
<211> LENGTH: 12
<212> TYPE: PRT
<213> ORGANISM: Motif
<220> FEATURE:
<221> NAME/KEY: MISC_FEATURE
<222> LOCATION: (2)..(2)
<223> OTHER INFORMATION: Xaa is D or E
<220> FEATURE:
<221> NAME/KEY: MISC_FEATURE
<222> LOCATION: (4)..(4)
<223> OTHER INFORMATION: Xaa is M or L
<220> FEATURE:
<221> NAME/KEY: MISC_FEATURE
<222> LOCATION: (5)..(5)
<223> OTHER INFORMATION: Xaa is A or P. When the amino acid at position
      5 is A, the amino acid at position 8 is P, A, Q, or L. When the
      amino acid at position 5 is P, the amino acid at position 8 is P,
      A, Q, or T.
<220> FEATURE:
<221> NAME/KEY: MISC_FEATURE
<222> LOCATION: (6)..(6)
<223> OTHER INFORMATION: Xaa is P or A
<220> FEATURE:
<221> NAME/KEY: MISC_FEATURE
<222> LOCATION: (8)..(8)
<223> OTHER INFORMATION: Xaa is P, A, Q, L, or T. If the amino acid at
      position 5 is A, the amino acid at position 8 is P, A, Q, or L. If
      the amino acid at position 5 is P, the amino acid at position 8 is
      P, A, Q, or T.
<220> FEATURE:
<221> NAME/KEY: MISC_FEATURE
<222> LOCATION: (9)..(10)
<223> OTHER INFORMATION: X is any amino acid

<400> SEQUENCE: 34

Phe Xaa Phe Xaa Xaa Xaa Pro Xaa Xaa Xaa Tyr Tyr
1               5                   10

<210> SEQ ID NO 35
<211> LENGTH: 5
<212> TYPE: PRT
<213> ORGANISM: Motif

<400> SEQUENCE: 35

Pro Pro Thr Pro Thr
1               5

<210> SEQ ID NO 36
<211> LENGTH: 7
<212> TYPE: PRT
<213> ORGANISM: Motif
<220> FEATURE:
<221> NAME/KEY: MISC_FEATURE
<222> LOCATION: (1)..(1)
<223> OTHER INFORMATION: X is L or V
<220> FEATURE:
<221> NAME/KEY: MISC_FEATURE
<222> LOCATION: (4)..(4)
<223> OTHER INFORMATION: X is any amino acid

<400> SEQUENCE: 36

Xaa Ala Ser Xaa Asp Val Leu 1               5

<210> SEQ ID NO 37
<211> LENGTH: 8
<212> TYPE: PRT
<213> ORGANISM: Motif
<220> FEATURE:
<221> NAME/KEY: MISC_FEATURE
<222> LOCATION: (1)..(1)
<223> OTHER INFORMATION: X is R or Q
<220> FEATURE:
<221> NAME/KEY: MISC_FEATURE
<222> LOCATION: (4)..(4)
<223> OTHER INFORMATION: X is S or T
<220> FEATURE:
<221> NAME/KEY: MISC_FEATURE
<222> LOCATION: (5)..(5)
<223> OTHER INFORMATION: X is P or A

<400> SEQUENCE: 37

Xaa Ala Arg Xaa Xaa Met Gly Gly
1               5

<210> SEQ ID NO 38
<211> LENGTH: 8
<212> TYPE: PRT
<213> ORGANISM: Motif
<220> FEATURE:
<221> NAME/KEY: MISC_FEATURE
<222> LOCATION: (1)..(1)
<223> OTHER INFORMATION: X is selected from the group K;D;E;N
<220> FEATURE:
<221> NAME/KEY: MISC_FEATURE
<222> LOCATION: (4)..(4)
<223> OTHER INFORMATION: X is D or E

<400> SEQUENCE: 38

Xaa Tyr Tyr Xaa Gly Val Arg Arg
1               5

<210> SEQ ID NO 39
<211> LENGTH: 6
<212> TYPE: PRT
<213> ORGANISM: Motif

<400> SEQUENCE: 39

Gln Glu Leu Gly Val Leu
1               5

<210> SEQ ID NO 40
<211> LENGTH: 7
<212> TYPE: PRT
<213> ORGANISM: Motif
<220> FEATURE:
<221> NAME/KEY: MISC_FEATURE
<222> LOCATION: (1)..(1)
<223> OTHER INFORMATION: X is H or Y
<220> FEATURE:
<221> NAME/KEY: MISC_FEATURE
<222> LOCATION: (2)..(2)
<223> OTHER INFORMATION: X is H or N
<220> FEATURE:
<221> NAME/KEY: MISC_FEATURE
<222> LOCATION: (5)..(5)
<223> OTHER INFORMATION: X is P or S

<400> SEQUENCE: 40

Xaa Xaa Gly Gly Xaa Gly Val
1               5

<210> SEQ ID NO 41

```
<211> LENGTH: 8
<212> TYPE: PRT
<213> ORGANISM: Motif
<220> FEATURE:
<221> NAME/KEY: MISC_FEATURE
<222> LOCATION: (5)..(5)
<223> OTHER INFORMATION: X is selected from the group consisting of
      R;V;K;Q
<220> FEATURE:
<221> NAME/KEY: MISC_FEATURE
<222> LOCATION: (7)..(7)
<223> OTHER INFORMATION: X is selected from the group consisting of
      Q;R;E

<400> SEQUENCE: 41

Glu Lys Asp Glu Xaa Gly Xaa Glu
1               5
```

METHODS FOR THE PRODUCTION OF PLANTS RESISTANT TO HPPD HERBICIDES

This is a divisional of U.S. patent application Ser. No. 10/416,940, filed Oct. 3, 2003, now U.S. Pat. No. 7,312,379 issued on Dec. 25, 2007, which is a U.S. National Phase of Intl. Patent Appl. No. PCT/GB01/05028, filed Nov. 14, 2001, which claims priority to Great Britain Patent Appl. No. 0117393.9, filed Jul. 17, 2001 and Great Britain Patent Appl. No. 0029899.2, filed Dec. 7, 2000, all of which are incorporated herein in their entirety.

FIELD OF THE INVENTION

The present invention relates to recombinant DNA technology, and in particular to the production of (i) transgenic plants which exhibit substantial resistance or substantial tolerance to herbicides when compared with non transgenic like plants; and (ii) transgenic plants which contain relatively elevated levels of lipid soluble anti-oxidants, likewise when compared with non-transgenic such plants. The invention also relates, inter alia, to the nucleotide sequences (and expression products thereof) when used in the production of, or when produced by, the said transgenic plants.

BACKGROUND OF THE INVENTION

Plants which are substantially "tolerant" to a herbicide when they are subjected to it provide a dose/response curve which is shifted to the right when compared with that provided by similarly subjected non tolerant like plants. Such dose/response curves have "dose" plotted on the x-axis and "percentage kill", "herbicidal effect" etc. plotted on the y-axis. Tolerant plants will typically require at least twice as much herbicide as non tolerant like plants in order to produce a given herbicidal effect. Plants which are substantially "resistant" to the herbicide exhibit few, if any, necrotic, lytic, chlorotic or other lesions when subjected to the herbicide at concentrations and rates which are typically employed by the agricultural community to kill weeds in the field.

Within the context of the present invention the terms hydroxy phenyl pyruvate (or pyruvic acid) dioxygenase (HPPD), 4-hydroxy phenyl pyruvate (or pyruvic acid) dioxygenase (4-HPPD) and p-hydroxy phenyl pyruvate (or pyruvic acid) dioxygenase (p-OHPP) are synonymous.

Methods for providing plants which are tolerant to HPPD herbicides which comprise transformation of plant material with polynucleotides comprising regions which encode HPPD enzymes are known. However what has not hitherto been generally recognized is that different HPPD enzymes provide different levels of tolerance to different HPPD-inhibitor herbicides. While a given HPPD enzyme may provide a useful level of tolerance to some HPPD-inhibitor herbicides it may be quite inadequate to provide commercial levels of tolerance to a different, more desirable HPPD-inhibitor herbicide which, for example, may control a different spectrum of weeds, be cheaper to make or offer environmental benefits. As well as particular HPPD enzymes and the polynucleotides which encode them the current invention also provides a means of selecting HPPD enzymes suitable for providing commercially useful levels of resistance to particular HPPD-inhibitor herbicide chemistries.

In order to provide for plants with tolerance to commercially useful application rates of a desired HPPD herbicide it would be an advantage to use polynucleotides which encode HPPD enzymes having reduced susceptibility to inhibition by the desired HPPD herbicide or class of HPPD herbicides. This characteristic of reduced susceptibility to inhibition by HPPD herbicides in vitro is also expressed herein as 'increased resistance' or 'inherent tolerance'.

Some mutant forms of a *Pseudomonas* sp. HPPD are claimed to exhibit such increased resistance on the basis of exhibiting an apparently decreased rate of binding of inhibitor to the enzyme (i.e., on the basis of measurements essentially corresponding to $k_{on}$ in the equilibrium E+I ⇌ EI, vide infra). However such mutant enzyme forms have reduced catalytic activity and/or reduced stability which, potentially, renders them unsuitable for use especially in the warm climate crops, particularly corn and soybean for which HPPD-inhibitor herbicides generally provide the most useful spectrum of weed control. It has not hitherto been known that various unmutated wild-type HPPD enzymes from different sources can equally exhibit useful and different inherent levels of tolerance and that, furthermore, unmutated wild-type enzymes are preferable for use in transgenic plants because, in general, they exhibit considerably better stability and activity (kcat/Km) than the mutant derivatives.

Furthermore it has not hitherto been appreciated that the level of inherent tolerance of these wild-type HPPD enzymes or indeed of mutated HPPD enzymes can vary markedly according to the particular class and structure of HPPD inhibitor. Neither has it been known that these differences in tolerance have their basis not in differences in the parameter $k_{on}$, addressed by previously used assay methods, but rather, in the parameters Kd, and $k_{off}$. It has also not been appreciated that these differences in inherent tolerance can be marked and useful even between HPPD enzymes having relatively similar amino acid sequences as, for example, between sequence similar HPPD enzymes derived from different species of plants. In order to maintain the widest range of options for herbicide modes of action useful for the control of volunteer crops and to minimize any potential impact of gene flow to weeds it is desirable that the herbicide tolerance conferred upon transgenic plants be expressed preferentially toward only certain desired subclasses of HPPD inhibitor herbicides. This is another benefit of being able to choose a particular HPPD enzyme most suited to delivering resistance to a particular set of HPPD herbicide types.

SUMMARY OF THE INVENTION

The present invention relates to nucleotide sequences, derivative nucleotide sequences, and the like, encoding amino acid sequences having enzymatic activity such that the amino acid sequences are resistant to HPPD inhibitor herbicidal chemicals. The present invention also relates to methods for making transgenic plants that are resistant to HPPD herbicides due to the expression of resistant HPPD enzymes. The present invention also relates to methods for screening for new resistant HPPD enzymes, as well as to methods for controlling weeds in crop fields by spraying HPPD chemicals over the top of transgenic crop plants expressing resistant HPPD enzymes.

BRIEF DESCRIPTION OF THE DRAWINGS

FIG. 1 shows the rate of exchange of C14 mesotrione from wheat and from *Arabidopsis* HPPD.

FIG. 2 shows the rate of exchange of C14 mesotrione and of structure II bound to *Arabidopsis* HPPD with excess 14C mesotrione.

FIG. 3 shows the progressive inhibition of wheat HPPD by structure II.

FIG. 4 shows the progressive inhibition of wheat HPPD by structure VI.

FIG. 5 shows the binding of C14 mesotrione to *Arabidopsis* HPPD.

DETAILED DESCRIPTION OF THE INVENTION

When the word "specific" is used in conjunction with the resistance of a particular protein to a particular herbicide—or class of herbicide, the term obviously does not exclude some degree of sensitivity—especially in the case that high levels (non-commercial application rates) of herbicidally are applied.

By "triketone herbicide" is meant a derivative of a cyclohexane 1,3 dione or a bicyclo[3,2,1]octane-2-4dione.

By "syncarpic acid" is meant a derivative of a 4,4,6,6-tetramethylcyclo-hexane 1,3,5-trione.

According to the present invention there is provided a triketone inhibitor specific resistant —HPPD enzyme comprising an amino acid sequence QIKECQ (SEQ ID NO: 33) and a sequence F, (D/E), F, (M/L), W1, (P/A), P, W2, X, X, Y, Y (SEQ ID NO: 34) wherein W1 is either A or P and where (i) if W1 is A then W2 is P, A, Q or L, or (ii) if W1 is P then W2 is P, A, Q or T, wherein X is any amino acid.

The present invention also provides a triketone inhibitor specific resistant HPPD enzyme comprising an amino acid sequence PPTPT (SEQ ID NO: 35) and a sequence F, (D/E), F, (M/L), W1, (P/A), P, W2, X, X, Y, Y (SEQ ID NO: 34) wherein W1 is either A or P and where (i) if W1 is A then W2 is P, A, Q or L, or, if (ii) W1 is P then W2 is P, A, Q or T, and X is any amino acid.

In a preferred embodiment of the present inventive enzyme the enzyme further comprises at least one of the following sequences:

```
(i)
(L/V), A, S, X, D, V, L        (SEQ ID NO:36)

(ii)
(R/Q), A, R, (S/T), (P/A), M, G, G   (SEQ ID NO:37)

(iii)
(K/D/E/N), Y, Y, (D/E), G, V, R, R  (SEQ ID NO:38)

(iv)
Q, E, L, G, V, L               (SEQ ID NO:39)

(v)
(H/Y), (H/N), G, G, (P/S), G, V  (SEQ ID NO:40)

(vi)
E, K, D, E, (R/V/K/Q), G, (Q/R/E), E (SEQ ID NO:41)
``` where X is any amino acid.

The present inventive HPPD-inhibitor resistant HPPD enzyme may be able to form a complex with an HPPD inhibitor of Structure I wherein the dissociation constant (Kd) of said complex, in water at pH 7.0 and at 25 C, is within the range from 1.0 to 30 nM and/or the dissociation rate constant of the complex, in water at pH 7.0 and at 25 C, is within the range of from $4\times10^{-5}$ to $2\times10^{-3}$ $s^{-1}$.

STRUCTURE I. 2-(Nitro-4-methanesulphonylbenzoyl)-cyclohexane-1,3-dione

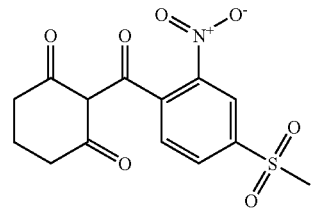 [SMILES: CS(=O)(=O)c1ccc(C(=O)C2C(=O)CCCC2=O)c([N+](=O)[O-])c1]

The kcat/Km hydroxyphenylpyruvate value of the HPPD-inhibitor resistant HPPD enzyme may be in the range of from 0.8 to 5.0 $s^{-1}\mu M^{-1}$ at pH 7.0, and 25° C.

The present invention also provides an HPPD inhibitor resistant HPPD enzyme excluding those derived from maize, wheat and barley, characterised in that in comparison with an *Arabidopsis* derived HPPD enzyme, the resistant enzyme exhibits at least a 2.5 and preferably a four fold increased resistance to herbicides selected from those of Formula 1 and/or Formula 2 as compared to herbicides selected from Formula 3 and/or Formula 4 as depicted below. Note that wherever structures are drawn in a keto form that these structures can also exist in an enolic form and that all of these and all other tautomeric forms are also included within the formula.

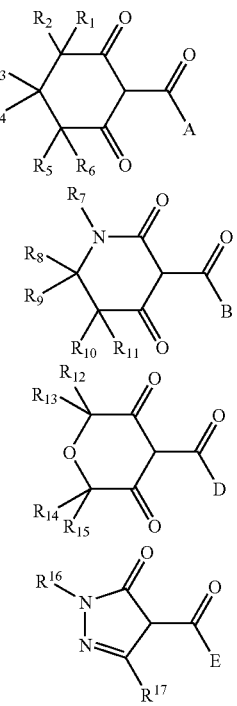

Formula 1 where Ar groups A, B, D and E are independently chosen from optionally substituted phenyl or optionally substituted heteroaryl. $R_1$ or $R_2$ or both are H and both $R_3$ and $R_4$ are H and $R_5$ or $R_6$ or both are H. $R_8$ and $R_9$ are both H and $R_{10}$ or $R_{11}$ or both are H. $R_{12}$ or $R_{13}$ or both are H and $R_{14}$ or $R_{15}$ or both are H. Aside from these constraints, $R_1$-$R_{17}$ are each individually selected from the group consisting of H, —$C_1$-$C_4$ alkyl, $C_3$-$C_6$ cycloalkyl, halogen, OH, SH, CN, —$NH_2$, —NHCOR, —CONHR, —COR, —SR, SOR, —SO$_2$R, NHR—SO$_2$R, —CO$_2$R, —NO$_2$, CF$_3$, —SF$_5$, OR, and CO$_2$H where R=C$_1$-C$_6$ alkyl or aryl optionally substituted with one or more substituents selected from the group consisting of halo or C$_1$-C$_4$ alkoxy.

Optional substituents for the groups A, B, D and E include —C$_1$-C$_4$ alkyl, C$_3$-C$_6$ cycloalkyl, halogen, OH, SH, CN, —NH$_2$, —NHCOR, —CONHR, —COR, —SR, SOR, —SO$_2$R, NHR—SO$_2$R, —CO$_2$R, —NO$_2$, CF$_3$, —SF$_5$, OR, and CO$_2$H where R=C$_1$-C$_6$ alkyl or aryl optionally substituted with one or more substituents selected from the group consisting of halo or C$_1$-C$_4$ alkoxy.

In a preferred embodiment of the method Ar is substituted phenyl and R$_{1-3}$, R$_5$ and R$_6$ are each H and R$_4$ is not H. Alternatively, in a more preferred embodiment, Ar may be substituted phenyl and R$_1$ R$_6$ are all H. The said phenyl may have H at all positions other than 2 and 4, which are then preferably substituted at position 2 with NO$_2$ or Cl and at position 4 with SO$_2$Me or Cl.

In a further preferred embodiment Ar is a substituted 3-pyridyl. Optionally the pyridyl N may be N-oxide. The said pyridyl may have H at all positions other than 2 and 6, which are then preferably substituted at position 2 with R' and at position 6 with CF$_2$H, CF$_2$C$_1$ or CF$_3$ and where R' is Me, isopropyl, n-propyl, CH$_2$OMe, CH$_2$OEt, CH$_2$CH$_2$OMe or CF$_3$.

Herbicidal HPPD inhibitors of Formula 1 include their agronomically acceptable salts. According to particular preferred embodiments (i) polynucleotides of the invention are selected to encode HPPD inhibitor resistant HPPD enzymes and (ii) plants are produced which are substantially tolerant to representative examples of herbicide Formula 1 such as 2-(2-Nitro-4-trifluoromethylbenzoyl)-cyclohexane-1,3-dione and/or 2-(2-Chloro-4-methanesulphonylbenzoyl)-cyclohexane-1,3-dione, and/or 2-(Nitro-4-methanesulphonylbenzoyl)-cyclohexane-1,3-dione, the second and third of which are known respectively as sulcotrione and mesotrione.

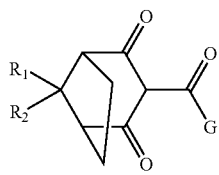

Formula 2 where group G is chosen from optionally substituted phenyl or optionally substituted heteroaryl. R$_1$-R$_2$ are each individually selected from the group consisting of H, —C$_1$-C$_4$ alkyl, C$_3$-C$_6$ cycloalkyl, halogen, OH, SH, CN, —NH$_2$, —NHCOR, —CONHR, —COR, —SR, SOR, —SO$_2$R, NHR—SO$_2$R, —CO$_2$R, —NO$_2$, CF$_3$, —SF$_5$, OR, and CO$_2$H where R=C$_1$-C$_6$ alkyl or aryl optionally substituted with one or more substituents selected from the group consisting of halo or C$_1$-C$_4$ alkoxy.

Preferably both R$_1$ and R$_2$ are H.

Optional substituents for the group G, include —C$_1$-C$_4$ alkyl, C$_3$-C$_6$ cycloalkyl, halogen, OH, SH, CN, —NH$_2$, —NHCOR, —CONHR, —COR, —SR, SOR, —SO$_2$R, NHR—SO$_2$R, —CO$_2$R, —NO$_2$, CF$_3$, —SF$_5$, OR, and CO$_2$H where R=C$_1$-C$_6$ alkyl or aryl optionally substituted with one or more substituents selected from the group consisting of halo or C$_1$-C$_4$ alkoxy or C$_1$-C$_4$ alkoxyalkoxy.

Herbicidal HPPD inhibitors of Formula 2 include their agronomically acceptable salts. In a preferred embodiment Ar is a substituted 3-pyridyl and R$_1$ and R$_2$ are both H. Optionally the pyridyl N may be N-oxide. The said pyridyl may have H at all positions other than 2 and 6, which are then preferably substituted at position 2 with R' and at position 6 with CF$_2$H, CF$_2$C$_1$ or CF$_3$ and where R' is Me, isopropyl, n-propyl, CH$_2$OMe, CH$_2$OEt, CH$_2$CH$_2$OMe or CF$_3$. According to particular preferred embodiments (i) polynucleotides of the invention are selected to encode HPPD-inhibitor resistant HPPD enzymes and (ii) plants are produced which are substantially tolerant to representative examples of herbicide Formula 2 such as:

3-[[2-methyl-6-(trifluoromethyl)-3-pyridinyl]carbonyl]-bicyclo[3.2.1]-octane-2,4-dione and/or 3-[[2-(ethoxymethyl)-6-(trifluoromethyl)-3-pyridinyl]carbonyl]-bicyclo[3.2.1]-octane-2,4-dione and/or 3-[[2-(methoxyethoxymethyl)-6-(trifluoromethyl)-3-pyridinyl]carbonyl]-bicyclo[3.2.1]-octane-2,4-dione

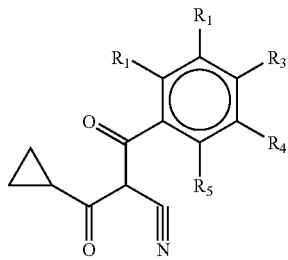

Formula 3

R$_1$-R$_6$ are each individually selected from the group consisting of H, —C$_1$-C$_4$ alkyl, C$_3$-C$_6$ cycloalkyl, halogen, OH, SH, CN, —NH$_2$, —NHCOR, —CONHR, —COR, —SR, SOR, —SO$_2$R, NHR—SO$_2$R, —CO$_2$R, —NO$_2$, CF$_3$, —SF$_5$, OR, and CO$_2$H where R=C$_1$-C$_6$ alkyl or aryl optionally substituted with one or more substituents selected from the group consisting of halo or C$_1$-C$_4$ alkoxy.

Herbicidal HPPD inhibitors of Formula 3 include their agronomically acceptable salts. In preferred embodiments R$_1$ is SO$_2$Me, R$_3$ is CF$_3$ or C$_1$ and R$_2$, R$_4$ and R$_5$ are each H; in the case that R$_3$ is CF$_3$, the compound is the active diketonitrile derivative of the herbicide isoxaflutole. According to particular preferred embodiments (i) polynucleotides of the invention are selected to encode HPPD-inhibitor resistant HPPD enzymes and (ii) plants are produced which are substantially tolerant to representative examples of herbicide Formula 3 (or compounds which give rise to them) such as 5-cyclopropyl-4-(2-methylsulphonyl-4-trifluoromethylbenzoyl)-isoxazole and/or 1-[2-(methanesulfonyl)-4-(trifluoromethyl)phenyl]-3-cyclopropyl-2-cyano-propane-1,3-dione the former of these compounds is the herbicide isoxaflutole, the second is its active derivative.

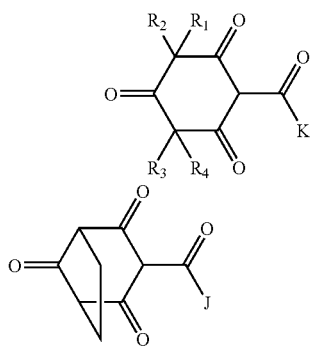

Formula 4 where Ar groups K and J are independently chosen from optionally substituted phenyl or optionally substituted heteroaryl. $R_1$-$R_4$ are each individually selected from the group consisting of —$C_1$-$C_4$ alkyl, $C_3$-$C_6$ cycloalkyl, halogen, OH, SH, CN, —$NH_2$, —NHCOR, —CONHR, —COR, —SR, SOR, —$SO_2R$, NHR—$SO_2R$, —$CO_2R$, —$NO_2$, $CF_3$, —$SF_5$, OR, and $CO_2H$ where R=$C_1$-$C_6$ alkyl or aryl optionally substituted with one or more substituents selected from the group consisting of halo or $C_1$-$C_4$ alkoxy. Optional substituents for groups K and J include —$C_1$-$C_4$ alkyl, $C_3$-$C_6$ cycloalkyl, halogen, OH, SH, CN, —$NH_2$, —NHCOR, —CONHR, —COR, —SR, SOR, —$SO_2R$, NHR—$SO_2R$, —$CO_2R$, —$NO_2$, $CF_3$, —$SF_5$, OR, and $CO_2H$ where R=$C_1$-$C_6$ alkyl or aryl optionally substituted with one or more substituents selected from the group consisting of halo or $C_1$-$C_4$ alkoxy.

Herbicidal HPPD inhibitors of Formula 4 include their agronomically acceptable salts. In some preferred embodiments Ar is substituted phenyl and $R_{1-4}$ are each methyl. The said phenyl may have H at all positions other than 2 and 4, which are then preferably substituted at position 2 with $NO_2$, Me, OMe or Cl and at position 4 with $SO_2Me$, CN, OR or Cl where R=$C_1$-$C_6$ alkyl or aryl optionally substituted with one or more substituents selected from the group consisting of halo or $C_1$-$C_4$ alkoxy. In a further preferred embodiment Ar is a substituted 2-pyridyl and $R_1$ and $R_2$ are both H. The said pyridyl may have H at all positions other than 3 and 5, which are then preferably substituted at position 3 with R' and at position 6 with $CF_2H$, $CF_2Cl$ or $CF_3$ and where R' is Me, isopropyl, n-propyl, $CH_2OMe$, $CH_2OEt$, $CH_2CH_2OMe$ or $CF_3$.

The present invention also provides an HPPD inhibitor resistant HPPD enzyme obtainable from *Avena, Lolium, Chenchrus, Festuca, Eleusine, Brachiara* or *Sorghum* plants.

The present invention further provides an HPPD inhibitor resistant HPPD enzyme having a sequence selected from the group consisting of SEQ ID Nos. 8, 10, 12, 14, 16, 18 or 20 or a sequence that has, based on the Clustal method of alignment and when compared along any given 150 amino acid stretch of the alignment, at least 93% identity with the sequence of SEQ ID Nos. 8, 10, 12, 14, 16, or 18 or the enzyme of SEQ ID No. 4 or a sequence that has, based on the Clustal method of alignment and when compared along any given 150 amino acid stretch of the alignment, at least 91% identity with the sequence of SEQ ID No. 4.

The skilled man is well aware of what is meant by the Clustal method of alignment and reference to it is made in WO 00/32757.

The present invention also provides herbicide resistant plants which contain a heterologous polynucleotide which comprises a region which encodes a triketone resistant HPPD, HPPD enzyme of the current invention.

The present invention further provides a method of selecting a polynucleotide which encodes a triketone inhibitor specific resistant HPPD inhibitor enzyme comprising screening a population of HPPD enzyme encoding sequences and selecting as those which encode an HPPD inhibitor resistant HPPD enzyme those sequences which encode an enzyme which in comparison with a control HPPD enzyme is either at least 2.5 or preferably four fold more resistant to herbicides selected from Formula 1 as compared to herbicides selected from Formula 3 or is at least 2.5 or preferably four fold more resistant to herbicides selected from Formula 2 as compared to Formula 4, wherein the said control enzyme is selected so as to exhibit substantially the same selection of polynucleotides as is obtained when the control enzyme is derived from *Arabidopsis*.

The present invention yet further provides a method of selecting a polynucleotide which encodes a syncarpic acid specific HPPD inhibitor resistant HPPD enzyme comprising screening a population of HPPD enzyme encoding sequences and selecting as those which encode resistant HPPD enzyme those sequences which encode an enzyme which in comparison with a control HPPD enzyme is at least 2.5 or preferably four fold more resistant to HPPD inhibitors selected from Formula 1 and 4, as compared to Formula 1 and wherein the said control enzyme is selected so as to exhibit substantially the same selection of polynucleotides as is obtained when the control enzyme is derived from *Arabidopsis*. The control HPPD may be derived from a dicot—particularly *Arabidopsis* or tobacco, and the resistance of HPPD enzymes to herbicides may be determined by measuring the rate of dissociation of the enzyme/herbicide complex.

The HPPD enzyme encoded by the selected polynucleotide may have a kcat/Km hydroxyphenylpyruvate value in the range from 0.10 to 5 $s^{-1}\mu M^{-1}$ at pH 7.0, 25° C.

The present invention further provides a method for selecting polynucleotides which comprise a region encoding an HPPD inhibitor-resistant HPPD enzyme which comprises screening polynucleotides comprising a region which encodes an HPPD enzyme and selecting as polynucleotides comprising a region encoding an HPPD inhibitor-resistant HPPD enzyme those which encode an enzyme capable of forming a complex with triketone herbicidal HPPD inhibitors selected from Formula 1 and/or from Formula 2 wherein the dissociation of the said complex is governed by a dissociation constant (Kd), in water at pH 7.0 and at 25 C, within the range from 1.0 to 30 nM, and wherein the dissociation of the said complex has a dissociation rate constant ($k_{off}$), in water at pH 7.0 and at 25 C, within the range from $4\times10^{-5}$ to $2\times10^{-3}$ $s^{-1}$ and wherein said selected herbicidal HPPD inhibitors have at least a quarter of the herbicidal activity of mesotrione against dicot plants.

The present invention further provides a method for providing a plant which is tolerant to HPPD-inhibiting herbicides which comprises transformation of plant material with a polynucleotide which comprises a region which encodes an inhibitor resistant HPPD enzyme of the current invention as described above, or selectable according to any the methods of the current invention described above, and regeneration of that material into a morphologically normal fertile plant, with the proviso that the HPPD sequence is not derived from *Shewanella colwelliana*, or *Pseudomonas fluorescens*.

The polynucleotide may further comprise a region which encodes a protein capable of targeting the HPPD encoded by the sequence to subcellular organelles such as the chloroplast or mitochondria and the said targeting protein may have the sequence of (i) a chloroplast transit peptide or (ii) a chloroplast transit peptide-N-terminal portion of a chloroplast protein—chloroplast transit peptide.

The said polynucleotide may further comprise a sequence which encodes an HPPD-inhibiting herbicide degrading or otherwise detoxifying enzyme, and/or a protein otherwise capable of specifically binding to the said HPPD-inhibiting herbicide.

The polynucleotide may further comprise a region which encodes (i) the target for a non-HPPD inhibitor herbicide and/or (ii) a non-HPPD inhibitor herbicide degrading or otherwise detoxifying enzyme and/or a region encoding a protein capable of conferring on plant material transformed with the region resistance to insects, fungi and/or nematodes.

The said target or enzyme may be selected from the group consisting of a cytochrome p450, a glutathione S transferase, glyphosate oxidase (GOX), phosphinothricin acetyl transferase (PAT), 5-enolpyruvylshikimate-3-phosphate synthase (EPSPS), acetolactate synthase (ALS), protoporphyrinogen oxidase (PPGO) and phytoene desaturase (PD) or mutagenised or otherwise modified forms thereof.

The present invention yet further provides a morphologically normal fertile whole plant obtained by any of the methods of the current invention which are described above.

The present invention further provides use of the polynucleotide selectable according to any of the methods of the current invention described above in the production of plant tissues and/or morphologically normal fertile whole plants which are transgenic for the inhibitor resistant HPPD enzyme.

The present invention further provides a method of selectively controlling weeds at a locus comprising crop plants and weeds, wherein the plants are obtained by any of the methods of the current invention described above, wherein the method comprises application to the locus of a weed controlling amount of an HPPD inhibitor. The HPPD inhibitor may be selected from the group consisting of herbicides having the Formulae 1 to 4 as indicated above. A pesticide selected from the group consisting of an insecticide, a fungicide and a non-HPPD inhibitor herbicide may also be applied to the locus.

The present invention further provides use of the polynucleotide selectable according to any embodiment of the current invention described above in the production of a herbicidal target for the high throughput in vitro screening of potential herbicides and in particular embodiments of this screening aspect of the invention the protein encoding regions of the polynucleotide may be heterologously expressed in *E. coli* or yeast.

In one aspect, the current invention relates to methods for the selection of polynucleotides comprising a region which encodes HPPD enzymes exhibiting a level of inherent tolerance to certain herbicides which is useful for application in herbicide tolerant plants. As well as exhibiting a high level of inherent tolerance to a selected HPPD inhibitor ($k_{off}$, Ki or Kd value) an HPPD enzyme encoded by a polynucleotide of the current invention may also, preferably, be possessed of high stability and high catalytic activity where catalytic activity is expressed by the parameter kcat/Km.

Methods for measuring the Km with respect to hydroxyphenylpyruvate of HPPD enzymes are well known. However, hitherto, the relative instability of HPPD has precluded measurement of true, relatively undiminished kcat values. Thus in a further aspect, the invention relates to methods for the selection of polynucleotides comprising a region which encode HPPD enzymes exhibiting kcat/Km values within a useful and determined range.

It will be appreciated that many methods well known to the skilled man are available for obtaining suitable candidate polynucleotides for screening and selection which comprise a region encoding an HPPD from a variety of different potential source organisms including microbes, plants, fungi, algae, mixed cultures etc. as well as environmental sources of DNA such as soil. These methods include inter alia the preparation of cDNA or genomic DNA libraries, the use of suitably degenerate oligonucleotide primers, the use of probes based upon known sequences or complementation assays (for example, for growth upon tyrosine) as well as the use of mutagenesis and shuffling in order to provide recombined or shuffled HPPD-encoding sequences.

In certain embodiments of selection, polynucleotides comprising candidate and control HPPD encoding sequences are expressed in yeast, in a bacterial host strain, in an alga or in a higher plant such as tobacco or *Arabidopsis* and the relative levels of inherent tolerance of the HPPD encoding sequences screened according to a visible indicator phenotype of the transformed strain or plant in the presence of different concentrations of the selected HPPD inhibitors. Dose responses and relative shifts in dose responses associated with these indicator phenotypes (formation of brown colour, growth inhibition, herbicidal effect etc) are conveniently expressed in terms, for example, of GR50 (concentration for 50% reduction of growth) or MIC (minimum inhibitory concentration) values where increases in values correspond to increases in inherent tolerance of the expressed HPPD.

It will be appreciated that many combinations of host organism, indicator phenotype and control HPPD would achieve a similar scope of selection and these are contemplated within the scope of the current invention. For example, in a relatively rapid assay system based upon transformation of a bacterium such as *E. coli*, each HPPD encoding sequence may be expressed, for example, as a DNA sequence under expression control of a controllable promoter such as the lacZ promoter and taking suitable account, for example by the use of synthetic DNA, of such issues as codon usage in order to obtain as comparable a level of expression as possible of different HPPD sequences. Such strains expressing polynucleotides comprising alternative candidate HPPD sequences may be plated out on different concentrations of the selected herbicides in, optionally, a tyrosine supplemented medium and the relative levels of inherent tolerance of the expressed HPPD enzymes estimated on the basis of the extent and MIC for inhibition of the formation of the brown, ochronotic pigment.

In variations of the method the cells may be permeabilized or, particularly in the case of yeast, be strains having disabled pumps in order to minimise the effects of differential uptake and export of HPPD inhibitors into and out of the cell. In a preferred variation of the method bacterial cells are grown almost to stationary phase in a liquid medium, exposed to selected herbicides for a short period of one hour or less, resuspended in a similar volume of fresh medium and the rate of development of pigment monitored. In a further preferred method candidate HPPD expressing sequences are transferred to a shuttle vector and, similar to above, are each expressed at a comparable level, but this time in a suitable *Pseudomonas* species such as *Pseudomonas fluorescens* 87-89 capable of being transformed and of growing on tyrosine as sole carbon source. Preferably the endogenous HPPD gene of the host *Pseudomonas* line is knocked out, for example, by recombinational insertion of an antibiotic marker gene. *Pseudomonas* lines each transformed to express an alternative resistant HPPD enzyme are grown on different concentrations of selected HPPD inhibitors and the inherent resistance of the expressed HPPD sequence in respect of each HPPD inhibitor estimated upon the basis of the concentration necessary to prevent growth on a medium containing tyrosine as sole carbon source.

One skilled in the art will recognise that there exist many potential variants of these methods for selecting polynucleotides which would achieve essentially the same selection result and which are contemplated within the scope of the current invention. In general, such microorganism-based methods of selection are suitable for achieving a relatively high throughput of candidate polynucleotides and are particularly suited to initial pre-screening. However, because of potential problems with the acuity of discrimination arising from the differential uptake and metabolism of selected herbicides and, furthermore, because the very high inherent potencies of many herbicidal HPPD inhibitors may limit the theoretical resolution of methods based upon MIC values, it is preferable to also use further embodiments of the selection method of the current invention.

In further particularly preferred aspects of the methods of the present invention for screening and selecting polynucleotides comprising a sequence encoding preferentially inhibitor resistant HPPD enzymes, candidate polynucleotides are transformed into plant material, regenerated into morphologically normal fertile plants which plants are then measured for differential tolerance to selected HPPD-inhibitor herbicides. Many suitable methods for transformation using suitable selection markers such as kanamycin, binary vectors such as from *Agrobacterium* and plant regeneration as, for example, from tobacco leaf discs are well known in the art. Optionally, a control population of plants is likewise transformed with a polynucleotide expressing the control HPPD. Alternatively, an untransformed dicot plant such as *Arabidopsis* or Tobacco can be used as a control since this, in any case, expresses its own endogenous HPPD. The average, and distribution, of herbicide tolerance levels of a range of primary plant transformation events or their progeny to herbicidal HPPD inhibitors selected from Formula 1, Formula 2, Formula 3 and/or Formula 4 are evaluated in the normal manner based upon plant damage, meristematic bleaching symptoms etc. at a range of different concentrations of herbicides. These data can be expressed in terms of, for example, GR50 values derived from dose/response curves having "dose" plotted on the x-axis and "percentage kill", "herbicidal effect", "numbers of emerging green plants" etc. plotted on the y-axis where increased GR50 values correspond to increased levels of inherent tolerance of the expressed HPPD. Herbicides can suitably be applied pre-emergence or post-emergence.

Polynucleotides of the invention are selected as those where, determined on the basis of the their effects on plants, the ratio of the inherent tolerance of the expressed HPPD to an inhibitor selected from Formula 1 or 2 to that for an HPPD inhibitor selected from Formula 3 or Formula 4 (R12/R34) is either, at least about 2.5 and preferably four fold greater than, or, at least about 2.5 and preferably four fold less than the same ratio determined in respect of the same pair of selected compounds for the control HPPD. It will be appreciated that many combinations of higher or lower plant, indicator phenotype, transformation method, assessment method and control HPPD would achieve a similar scope of selection and are contemplated within the scope of the current invention. Transient expression of the test HPPD genes in suitable green, transiently transformable green tissues such as mesophyll cell protoplasts or tobacco leaves is also optionally used in order to provide a more rapid means of selection. Suitable methods for such transient transformation of tissues are well known in the art and include, for example, leaf infiltration, vacuum infiltration and infection with *Agrobacterium* or bombardment of target tissues with DNA-coated particles.

In these transient assay methods, treated tissue is, for example, suitably transferred to media containing a range of concentrations of selected herbicides after about 0.1-7 days after transformation and assessed for visible signs of bleaching after a further 1-5 d. In order to provide an internal control to allow for differences in transient expression, constructs used for transformation may also comprise a gene such as GUS which expresses a readily quantifiable product. Whilst a preferred method, a limitation of methods based upon stable transformation of plants for polynucleotide selection include the relatively large number of events (preferably greater than 25) required, time-scale of several months required to turn around data and the further breeding, segregation analysis and testing of further generations which is ideally required to resolve biological variabilities and to make comparisons between the alternative HPPD genes expressed from different constructs.

In further particularly preferred embodiments of the selection methods of the present invention polynucleotides comprising a candidate region encoding an HPPD inhibitor resistant HPPD enzyme are selected on the basis of in vitro measurements of the comparative inherent resistance levels of the expressed candidate and control HPPD enzymes.

The particular combination of in vitro methods and criteria used herein are new. It is found here that active principles of HPPD herbicides which either are, or which have the potential to be, commercially useful tend also to be such potent inhibitors of HPPD enzymes that Ki values and other kinetic parameters useful for comparing the inherent resistance of HPPD enzymes cannot be derived from steady state enzyme kinetic or IC50 based enzyme assay methods as have generally been described in the HPPD literature.

Apparent IC50 values may generally be determined by arbitrary experimental parameters such as the concentration of enzyme used in the assay and the time allowed for reaction. Neither, even given the use of more appropriate methods, has it hitherto been known that processes hitherto described to partially or completely purify HPPD cause such damage to the enzyme as to alter the values of kinetic parameters and to such an extent as to confound useful comparison between the inherent tolerances of HPPD enzymes. In particular, the effect of a high proportion of the enzyme molecules being damaged and of diminished catalytic activity (expressed on a per active site basis) as a result of part purification is to reduce the measured apparent strength of HPPD binding interactions with inhibitors.

By way of a non-limiting illustration of the in vitro methods preferred herein, the HPPD sequences may conveniently be expressed in a yeast or in *E. coli* using, for example, expression from a T7 polymerase promoter or other such suitable methods which are well known in the art. Suitable extracts for in vitro experiments may, for example, be prepared by cell breakage, removal of cell debris and insoluble proteins by centrifugation and exchange of the fraction containing the expressed soluble HPPD enzyme into a suitable buffer. The, thus prepared extract may, optionally, be beaded frozen and stored at liquid Nitrogen temperature until required for use. Control HPPD enzymes are likewise prepared. Preferably, the handling and partial purification of the HPPD is minimised since, as mentioned above, it is found here, that most methods of attempting to purify or, optionally reconstitute with iron ions, result in losses of activity and inhibitor binding capacity which may obfuscate the desired comparisons between inherent resistance and activity level.

Optionally, the enzyme may be part-purified in the presence of inhibitors such as structure VIII (see later) which have a stabilising effect but which do not bind so tightly that they are difficult to subsequently remove. In vitro measurements are suitably carried out using, for example, *E. coli* extracts wherein the HPPD expressed from the transgene constitutes, for example, 0.25-10% of the total soluble protein. In a particular embodiment of the methods for selection of polynucleotides, the inherent resistance of expressed HPPD enzymes is evaluated in vitro on the basis of the rate of dissociation of the enzyme/herbicide complex ($k_{off}$ value) and/or, according to the dissociation constant (Kd) of the enzyme/herbicide complex.

Thus, in one aspect of the invention there is provided a method for selecting polynucleotides which comprise a region encoding an HPPD-inhibitor resistant HPPD enzyme which comprises screening a population of HPPD encoding sequences and selecting as those which encode an HPPD-inhibitor resistant HPPD enzyme those which encode an enzyme able to form a complex with herbicidal HPPD inhibitors selected from Formula 1 and/or Formula 2 wherein, in water at pH 7.0 and at 25 C, the dissociation of the said complex is governed by a dissociation constant (Kd) in the range 1-30 nM and/or a dissociation rate constant ($k_{off}$) in the range from $4 \times 10^{-5}$ to $2 \times 10^{-3}$ s$^{-1}$ and wherein the selected HPPD-inhibitor has at least a quarter of the herbicidal activity of mesotrione versus dicot plants. Activity versus dicot plants refers here to herbicidal activity averaged over a range of 6 or more of those dicot weed and crop species usually used in screens used for compound discovery in the agrochemical community. Herbicidal activity versus dicot plants also refers here to that activity which is due to the inhibitor per se rather than due to some, potentially more herbicidal, metabolite of it which may be formed in planta or otherwise.

In a further aspect of the invention there is provided a method for selecting polynucleotides which comprise a region encoding an HPPD-inhibitor resistant HPPD enzyme which comprises screening a population of HPPD encoding sequences and selecting as those which encode an HPPD-inhibitor resistant HPPD enzyme those which encode an enzyme able to form a complex with herbicidal HPPD inhibitors selected from Formula 3 and/or Formula 4 wherein, in water at pH 7.0 and at 25 C, the dissociation of the said complex is governed by a dissociation constant (Kd) in the range 1-30 nM and/or a dissociation rate constant ($k_{off}$) in the range from $4 \times 10^{-5}$ to $2 \times 10^{-3}$ and wherein the selected HPPD-inhibitor has at least a quarter of the herbicidal activity of mesotrione versus dicot plants.

In a yet further aspect there is provided a method of selecting a polynucleotide which encodes an HPPD-inhibitor resistant HPPD enzyme comprising screening a population of HPPD enzyme encoding sequences and selecting as those which encode an HPPD-inhibitor resistant HPPD enzyme those sequences which encode an enzyme which, in comparison with a control enzyme, exhibits at least a 2.5 fold and preferably greater than a 4 fold difference in inherent resistance to HPPD inhibitors selected from Formula 1 and/or 2 as compared to Formula 3 and/or 4 and wherein the said control enzyme is selected so as to exhibit substantially the same selection of polynucleotides as is obtained when the control enzyme is the wild type HPPD derived from *Arabidopsis*. To illustrate further what is meant by this and also what is meant by some of the terms used in the in vitro-based methods of selection of the current invention what follows relates to a non limiting example wherein the selected polynucleotide expresses HPPD from *Avena sativa* and wherein the control HPPD sequence is from *Arabidopsis*. The definitions and basis of selection used in this illustration apply analogously to the selection of other polynucleotides which encode other HPPD enzymes and which are selectable according to either the same or other in vitro methods of the invention. According to this example, a polynucleotide comprising a sequence encoding, in this case, the HPPD enzyme from *Avena sativa*, is selected as resistant when, in comparison with a control HPPD enzyme, in this case from *Arabidopsis*, the *Avena* HPPD enzyme is found to be more than 2.5 fold resistant to herbicidal inhibitors selected from Formula 1 and/or Formula 2 as compared to herbicides selected from Formula 3 and/or Formula 4. By this is meant, that, assayed under identical conditions (e.g at 25 C in 50 mM Bis-Tris-propane buffer at pH 6.5 or 7.0 containing either <4% or 25% v/v glycerol and either <2 or 20-25 mM sodium ascorbate) and preferably assayed using the same method, side by side on the same day:

(a) HPPD inhibitors selected from Formula 3 or 4 dissociate more slowly from the complex formed with HPPD derived from *Avena* than do HPPD-inhibitors selected from Formula 1 or 2, to the extent that the ratio of the value of $k_{off}$ (as illustrated in the scheme below) for the compound selected from Formula 1 or Formula 2 to the value of $k_{off}$ for the compound selected from Formula 3 or 4 ($k_{off}12/k_{off}34$) is at least 2.5 fold and, preferably more than 4 fold greater than the likewise derived ratio observed in respect of dissociation of the same pair of selected inhibitors from the, likewise obtained, *Arabidopsis* control enzyme.

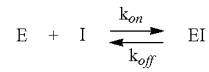

Herbicidal inhibitors of HPPD are found here to have generally low values of $k_{off}$ (in the range less than 0.0003 s$^{-1}$, often less than 0.000001 s$^{-1}$). It will be appreciated that many suitable methods known in the art for determining such low $k_{off}$ values are suitable for working the current invention. These include measuring rates of exchange of radio or otherwise labelled inhibitors either with or away from the enzyme inhibitor complex. For example enzyme inhibitor complexes can readily be prepared by incubating HPPD preparations with labelled or unlabelled inhibitor and then, after suitable periods, optionally rapidly separating the thus formed enzyme inhibitor complex from excess inhibitor by any suitable method such as ultrafiltration, binding to filters or exchange down a gel filtration column. Exchange reactions with the, thus prepared enzyme inhibitor complex is then initiated by addition of, as appropriate, excess labelled or unlabelled inhibitor. HPPD preparations suitable for use in the methods of the current invention are relatively unpurified, buffer-exchanged, supernatant fractions of spun crude lysates of *E. coli* strains engineered to express the HPPD enzyme of interest at a level of, typically, about 0.25-10% of the total soluble protein. Many methods such as radiometric, fluorimetric, NMR, fluorescence depolarisation, EPR, Mossbauer, UV/VIS spectrophotometry etc. or phonon resonance can, in principle, be used to monitor the enzyme/ligand exchange reactions and, particularly in this case where the enzyme contains an iron atom at the ligand binding site. Optionally, the monitoring method may be continuous (as, for example, with scintillation proximity/bead-based methods) or, discontinuous, based upon collection of data at various timepoints wherein samples are removed and the bound and unbound label components rapidly separated and quantitated.

Values of $k_{off}$ can suitably be calculated by computer fitting based upon numerical integration of the exchange data along with information on the active-site concentration of HPPD and upon $k_{on}$ values obtained as described below. In crude extracts of, for example, *Arabidopsis* HPPD it is routinely found that approximately 20-30% of bound mesotrione exchanges relatively rapidly (t ½<~30-40 min for dissociation of mesotrione at 25 C, pH 7.0 in 20-25% v/v glycerol) whereas 70-80%, presumed here to correspond to the bulk of genuine fully active enzyme exchanges slowly (t ½~4 d for dissociation of mesotrione at 25 C, pH 7.0 in 20-25% v/v glycerol). This presumption is supported by (1) the observation that further enzyme handling associated with activity loss leads to a relative increase in the proportion of the rapid exchanging fraction and (2) the observation that the fraction does not, on the other hand, vary according to the time of the complex formation (10 s to 24 h) and, is not, therefore, a kinetically trapped intermediate in the binding reaction. In any event, $k_{off}$ values are always here calculated from the rate of the major slow exchange reaction. It will be appreciated that within the scope of the current invention many methods of making the desired kinetic comparisons are possible without explicit or rigorous determination of off rates but, based upon the same underlying principle, will achieve the same selection result.

Or:

b) herbicidal inhibitors selected from Formula 3 or 4 bind, relative to the substrate HPP, more tightly to HPPD derived from *Avena* than do herbicides selected from Formula 1 or 2, to the extent that the ratio of the value of Kd (Kd=$k_{off}/k_{on}$ illustrated in the scheme below) for the compound selected from Formula 1 or Formula 2 to the value of Kd for the compound selected from Formula 3 or 4 (Kd12/Kd34) is at least 2.5 fold and, preferably more than 4 fold greater than the likewise derived ratio observed in respect of binding of the same pair of selected inhibitors from the, likewise obtained, *Arabidopsis* control enzyme.

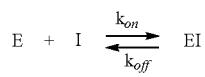

The method for determining $k_{off}$ values is outlined supra. In some embodiments of the method, Kd is determined by also determining the value of $k_{on}$, the rate constant governing the rate of formation of the complex of HPPD with inhibitor wherein Kd=$k_{off}/k_{on}$. Suitable enzyme kinetic methods for deriving values of $k_{on}$ are based upon the rate of onset of enzyme inhibition over a range of concentrations of inhibitor and of substrate. Suitable methods combine, for example, the HPLC assay for HPPD described by Viviani et al 1998 (Pestic. Biochem. Physiol., 62, 125-134) which assay can be started with addition of enzyme and data points collected over the first minute or so of reaction, standard methods for measurements of the value of the Km for hydroxyphenylpyruvate and methods of kinetic analysis/calculation as described for example by Schloss J. V. (1989) in "Target sites of Herbicide Action" (Boger P., and Sandmann G. eds) CRC Press Boca.

Alternatively estimates of $k_{on}$ values can be determined more directly by mixing HPPD with radio or otherwise labelled herbicide inhibitor and monitoring the progress of the binding reaction, optionally by rapidly isolating the enzyme inhibitor complex and/or by any one of a number of methods (for example fluorimetry, EPR, NMR, radiodetection etc). For example, the reaction with HPPD may be started by addition of radiolabelled herbicide, allowed to proceed for a series of different times and rapidly quenched by addition and mixing with a large excess of unlabelled inhibitor. In this case the extent of binding at different times may, for example, be monitored by using ultrafiltration, binding to filters or gel filtration to separate radiolabel-bound to HPPD from unbound label which fractions can then each be quantitated by scintillation counting.

When measuring $k_{on}$ via such measurements of physical binding it is important to note that the binding of most compounds versus some HPPD enzymes appears biphasic with half the sites binding quickly and then the remaining binding then occurring relatively very slowly. In such cases, it is the rapid initial binding phase, usually corresponding to rate constants in the range $0.1\text{-}4\times10^5$ $M^{-1}s^{-1}$, which provides the relevant rate constant. This corresponds to the value obtained from using enzyme assay-based methods since although only half the sites are initially bound, on the same time-scale essentially all of the HPPD catalytic activity is inhibited. It will be appreciated that within the scope of the current invention many more or less rigorous methods of making the desired kinetic comparisons, are possible which may not involve explicit determination of off rates and on rates but, based upon the same underlying principles, achieve the same selection result.

Thus, for example, in a preferred and relatively high throughput method, relative Kd values, which are all that is required for determining the required ratios of the Kd values of the selected HPPD inhibitors, are estimated indirectly via competition with the binding of a known standard or other 'surrogate' ligand. Such a surrogate ligand could be any molecule including a peptide, optionally, initially selected from a phage display library, an RNA aptamer or an antibody fragment. In a preferred embodiment it is a labelled HPPD inhibitor. Therefore, structure I or IV or V may be used as a labelled standard, and experiments set up where the relative Kd values of the selected HPPD inhibitors are evaluated on the basis of their ability to compete with and decrease the amount of labelled standard bound to the test or control HPPD.

STRUCTURE I

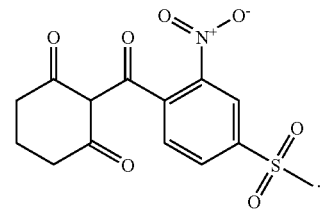

2-(Nitro-4-methanesulphonylbenzoyl)-cyclohexane-1,3-dione

STRUCTURE II

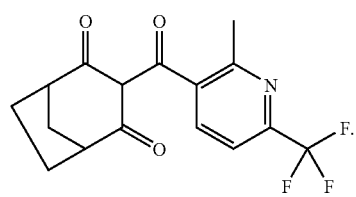

3-[[2-methyl-6-(trifluoromethyl)-3-pyridinyl]carbonyl]-bicyclo[3.2.1-octane-2,4-dione -continued

STRUCTURE III

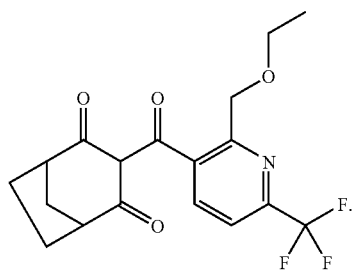

3-[[2-(ethoxymethyl)-6-(trifluoromethyl)-3-pyridinyl]carbonyl]-bicyclo[3.2.1]-octane-2,4-dione

STRUCTURE IV

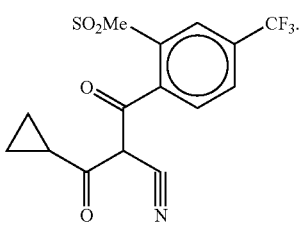

1-[2-(methanesulfonyl)-4-(trifluoromethyl)phenyl]-3-cyclopropyl-2-cyano-propane-1,3-dione

STRUCTURE V

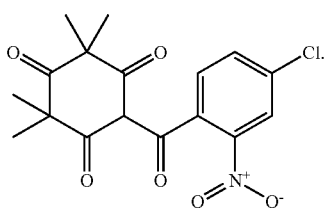

2-[2-nitro-4-chlorobenzoyl]-4,4,6,6-tetramethylcyclohexane-1,3,5-trione

STRUCTURE VI

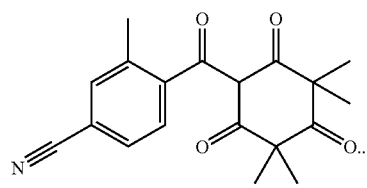

2-[2-methyl-4-cyanobenzoyl]-4,4,6,6-tetramethylcyclohexane-1,3,5-trione

STRUCTURE VII

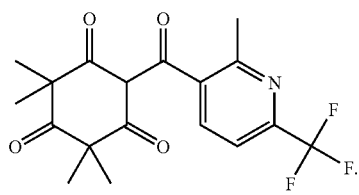

3-[[2-methyl-6-(trifluoromethyl)-3-pyridinyl]carbonyl]-4,4,6,6-tetramethylcyclohexane-1,3,5-trione -continued

STRUCTURE VIII

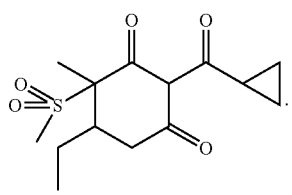

2-[cyclopropylcarbonyl]-5-ethyl-4-methanesulfonyl-4-methyl-cyclohexane-1,3-dione Ideally, in order to obtain the best approximations to equilibrium Kd values the competition binding reactions of HPPD plus standard and test inhibitors should be left to equilibrate at, for example, 25° C. for as long as possible to reach equilibrium and, preferably, days before sampling and evaluation via gel filtration or binding to a nitrocellulose filter etc of the amount of label which is unbound and which is bound to HPPD. It will be understood that such reactions may be left for shorter periods due to limitations in enzyme stability and that, as reaction times are made shorter, the values obtained become and more weighted to reflect differences in $k_{on}$ values rather than pure Kd values. It will be understood that, within the scope of the present invention, a great variety of alternative technologies such as that based upon Luminex fluorescence bead technology or Scintillation proximity counting could potentially be used, for example to avoid the need for a step to separate bound from unbound label, and provide essentially the same result. Using such methods the determination of relative Kd values can also be converted to a microtitre plate format and be useful not only for the selection of polynucleotides comprising regions which encode HPPD enzymes but also for the discovery of small molecule inhibitors as potential leads for new chemical herbicides.

In a yet further aspect, the invention comprises a method for, optionally, further selecting polynucleotides which encode inhibitor-resistant HPPD enzymes having a high catalytic activity by which is meant a kcat/Km hydroxyphenylpyruvate value in the range from 0.10 to 5 $s^{-1}\mu M^{-1}$ at pH 7.0, 25° C. Assays and measurements of Km are carried out using published methods such as the HPLC assay of Viviani et al 1998 (Pestic. Biochem. Physiol., 62, 125-134). Assay time courses curve off rapidly and, using such stopped methods, it is important to make sufficient initial rate measurements at suitably short times and to fit the data obtained appropriately to obtain rate estimates. Suitable HPPD preparations which retain most of the enzyme in a fully active form are, for example, rapidly prepared as relatively crude, buffer-exchanged, supernatant fractions of spun crude lysates of *E. coli* strains engineered to express the HPPD enzyme of interest at a level of, typically, about 0.2-10% of the total soluble protein.

In order to obtain kcat, the Vmax value (mol of HGA formed/s), obtained from experiments in which substrate concentration is varied, is divided by the concentration of enzyme active sites. There are many methods of determining active-site concentration. Herbicides such as that of structure I, IV or V bind very tightly to the active site of HPPD enzymes and, optionally labelled, make suitable active site probes useful for the determination of active-site concentration. Thus, for example, from titrations of extract containing an unknown concentration of active sites of HPPD versus a fixed concentration of labelled inhibitor, it is possible to describe a graph of extract dilution versus the amount of bound label and to thereby derive the concentration of inhibitor binding sites or 'active sites'. Many methods are suitable for monitoring the binding reaction including for example, use of radiolabels, NMR, EPR, Biacore (Pharmacia) etc.

Because the binding of some HPPD inhibitors is biphasic it is important to carry out the binding titration carefully and to vary the inhibitor and time since, in some cases the result obtained will be closer to a 'half sites' rather than a full quantitation of active site concentration. The binding reaction used for the titration needs, as far as possible, to be left to reach equilibrium as modified by practical considerations of enzyme stability. It will be appreciated that within the scope of the present invention many, more or less rigorous methods of making the desired kinetic comparisons are possible which may not involve explicit determination of kcat/Km but, based upon the same underlying principles, achieve the same result in terms of ranking the relative efficacies of polynucleotides comprising regions encoding an HPPD enzyme. For example, kcat and hence kcat/Km values may be derived by using antibodies raised to SDS PAGE purified HPPD polypeptides in order to quantitate the amount of HPPD polypeptide in active crude extracts using quantitative fluorescent Western or ELISA type assays. However, methods based upon quantitation of polypeptide are blind to whether or not the material represents active enzyme and, for this reason, the methods for the determination of kcat based upon inhibitor binding are preferred because, for inhibitors resembling catalytic reaction intermediates, the retention of this tight-binding capability is synonymous with the retention of catalytic function. As HPPD is further purified and loses more activity the damaged enzyme still binds labelled inhibitor but, as the activity diminishes, an increasing proportion of this binding becomes weaker and more rapidly exchanging. Therefore in a preferred embodiment of the method, the fraction of inhibitor binding sites which are in relatively rapid exchange are discounted in the calculation of kcat. Thus, for example, in crude extracts of *Arabidopsis* HPPD it is routinely found that, of the total measured binding capacity for mesotrione (Structure I), approximately 20-30% exchanges rapidly (t ½~30-40 min for dissociation of mesotrione at 25 C, pH 7.0 in 25% v/v glycerol) whereas 80%, presumed here to correspond to active enzyme exchanges slowly (t ½~4 d for dissociation of mesotrione at 25 C, pH 7.0 in 20% v/v glycerol). Thus, in this case, Kcat may be based upon an active site determination calculated as ~80% of the total measured binding capacity, although the values cited in this application do not take that potential adjustment into account.

In one aspect the present invention provides HPPD-inhibitor resistant HPPD enzymes which are not derived from maize, wheat or barley and which are characterised by the ability of the enzyme to form a complex with mesotrione wherein the dissociation of the said complex in water at pH 7.0 and at 25 C is governed by a dissociation constant (Kd) having a value in the range from 1.0 to 30 nM and/or wherein the dissociation of said complex is governed by a rate constant ($k_{off}$) having a value in the range from $4 \times 10^{-5}$ to $2 \times 10^{-3}$. In a further aspect, the said HPPD-inhibitor resistant enzyme is further characterised by having a kcat/Km value in the range from 0.1 to 5 $s^{-1} \mu M^{-1}$ and, more preferably, in the range from 0.8 to 5 $s^{-1} \mu M^{-1}$.

In a further aspect an HPPD-inhibitor resistant HPPD enzyme has an amino acid sequence selected from the group consisting of SEQ ID NOs. 8, 10, 12, 14, 16, 18 or 20 or a sequence that has, based on the Clustal method of alignment and when compared along any given 150 amino acid stretch of the alignment, at least 93% identity with the sequence of SEQ ID NOs. 8, 10, 12, 14, 16, or 18 or an HPPD inhibitor resistant HPPD enzyme of SEQ ID NO:4 or a sequence that has, based on the Clustal method of alignment and when compared along any given 150 amino acid stretch of the alignment, at least 91% identity with the sequence of SEQ ID NO:4.

The structures of HPPD inhibitors referred to in the specification and in some of the preferred embodiments of the invention are as follows. Note that wherever structures are drawn in a keto form that these structures can also exist in an enolic form and that all of these and all other tautomeric forms are also intended.

According to particular preferred embodiments (i) polynucleotides of the invention are selected to encode HPPD-inhibitor resistant HPPD enzymes and ii) plants are produced which are substantially tolerant to representative examples of herbicide Formula 4 such as 2-[2-nitro-4-chlorobenzoyl]-4,4,6,6-tetramethylcyclohexane-1,3,5-trione and/or 2-[2-methyl-4-cyanobenzoyl]-4,4,6,6-tetramethylcyclohexane-1,3,5-trione and/or 3-[[2-methyl-6-(trifluoromethyl)-3-pyridinyl]carbonyl]-4,4,6,6-tetramethylcyclohexane-1,3,5-trione The structures of the specific HPPD inhibitors referred to as numbered Structures I to VIII have already been described. According to particular preferred embodiments (i) polynucleotides of the invention are selected to encode HPPD-resistant HPPD enzymes and (ii) plants are produced which are substantially tolerant to one or more of these structures. Note that wherever structures are drawn in a keto form that these structures can also exist in an enolic form and that all of these and all other tautomeric forms are also intended.

It will be appreciated that the transformed plants, and the thus transformed plant material, of the present invention are tolerant or resistant to multiple herbicides within the groups of HPPD inhibitors represented by Formula 1, 2, 3 and 4 as well as to HPPD-inhibiting herbicides outside of these groupings such as 5-methyl-2-(2-Chloro-3-ethoxy-4-methanesulphonylbenzoyl)-cyclohexane-1,3-dione.

It will also be appreciated that those embodiments which are tolerant to HPPD inhibitors selected from Formula 1 and 2 will generally be less tolerant or resistant to herbicides, representative of Formula 3 and 4 such as structure V. Conversely, those embodiments which are tolerant to HPPD inhibitors selected from Formula 3 and 4 will be generally less tolerant or resistant to herbicides, representative of Formula 1 and 2 such as structure I (mesotrione). Where the embodiments are transgenic plants, herbicide may be applied either pre- or post emergence in accordance with the usual techniques for herbicide application.

The invention still further provides protein encoded by the presently disclosed polynucleotides and a vector comprising these polynucleotides comprising a HPPD sequence under expression control of a promoter derived from the gene encoding the small subunit of rubisco, a cestrum viral promoter, an actin promoter, a polyubiquitin promoter, the FMV35S promoter, a plastocyanin promoter, a histone promoter, the CaMV35S promoter and the GST1 promoter. In a further preferred embodiment, where the said plant is a monocot, the HPPD sequence is under expression control of a maize polyubiquitin promoter or a cestrum viral promoter. In a yet further preferred embodiment, where the said plant is a dicot crop plant, the HPPD sequence is under expression control of an *arabidopsis* small subunit of rubisco promoter, an *arabidopsis* actin promoter or a cestrum viral promoter.

The transformed plant material of the invention may be subjected to a first HPPD inhibitor—such as a triketone herbicide and visually selected on the basis of a colour difference between the transformed and non transformed material when subjected to the said herbicide. The non-transformed material may become and stay white when subjected to the selection procedure, whereas the transformed material may become white but later turn green, or may remain green, likewise, when subjected to the said selection procedure. Plant transformation, selection and regeneration techniques, which may require routine modification in respect of a particular plant species, are well known to the skilled man. In preferred embodiments of the selection method the said DNA (which distinguishes transformed from non-transformed plants) comprises a region selected from the group consisting of SEQ ID NOs 3, 7, 9, 11, 13, 15, 17 and 19 or it comprises a region which encodes an HPPD, which region is complementary to one which when incubated at a temperature of between 60 and 65° C. in 0.3 strength citrate buffered saline containing 0.1% SDS followed by rinsing at the same temperature with 0.3 strength citrate buffered saline containing 0.1% SDS still hybridises with a sequence selected from the group consisting of SEQ ID NOs. 3, 7, 9, 11, 13, 15, 17 and 19.

When the test and inventive sequences are double stranded the nucleic acid constituting the test sequence preferably has a $T_M$ within 10° C. of that of the sequence selected from the group consisting of SEQ ID NOs 3, 7, 9, 11, 13, 15, 17 and 19. In the case that the test and the sequence selected from the group consisting of SEQ ID NOs. 3, 7, 9, 11, 13, 15, 17 and 19 are mixed together and are denatured simultaneously, the $T_M$ values of the sequences are preferably within 5° C. of each other. More preferably the hybridisation is performed under relatively stringent conditions, with either the test or inventive sequences preferably being supported. Thus either a denatured test or inventive sequence is preferably first bound to a support and hybridisation is effected for a specified period of time at a temperature of between 60 and 65° C. in 0.3 strength citrate buffered saline containing 0.1% SDS followed by rinsing of the support at the same temperature but with 0.1 strength citrate buffered saline. Where the hybridisation involves a fragment of the sequence selected from the group consisting of SEQ ID NOs. 3, 7, 9, 11, 13, 15, 17 and 19 the hybridisation conditions may be less stringent, as will be obvious to the skilled man.

In the case that the polynucleotide encodes more than one protein, each protein encoding region may be under the transcriptional control of a plant operable promoter and terminator. It may be desired to target the translation products of the polynucleotide to specific sub-cellular compartments within the plant cell, in which case the polynucleotide comprises sequences encoding chloroplast transit peptides, cell wall targeting sequences etc. immediately 5' of the regions encoding the said mature translation products.

Translational expression of the protein encoding sequences contained within the said DNA sequence may be relatively enhanced by including known non translatable translational enhancing sequences 5' of the said protein encoding sequences. The skilled man is very familiar with such enhancing sequences, which include the TMV-derived sequences known as omega, and omega prime, as well as other sequences derivable, inter alia, from the regions 5' of other viral coat protein encoding sequences, such as that of the Tobacco Etch virus. Further preferred 5' untranslated regions include those derived from, for example, the genes encoding rubisco or glucanase.

The polynucleotides of the invention may be modified in that encoded mRNA instability motifs and/or fortuitous splice regions are removed, or, for example, dicot preferred codons are used so that expression of the thus modified sequence in a dicot plant yields substantially similar protein having a substantially similar activity/function to that obtained by expression of the unmodified sequence in the organism in which the protein encoding regions of the unmodified sequence are endogenous. In a further embodiment of the modified sequence the degree of identity between the modified sequence and a sequence endogenously contained within the said dicot plant and encoding substantially the same protein is less than about 70%.

The present invention also provides a morphologically normal fertile whole plant which is transgenic for a DNA sequence, which is not derived from maize, wheat or barley and which is selectable according to the methods of the current invention such that it comprises a region which encodes an HPPD-inhibitor resistant HPPD enzyme, preferably of high stability and having a kcat/Km value in the range from 0.10 to 5.0 s$^{-1}$ mM$^{-1}$, more preferably in the range from 0.8 to 5.0 s$^{-1}$ mM$^{-1}$ which, in comparison with a control HPPD enzyme derived from *Arabidopsis*, is at least 2.5 fold and, preferably, greater than 4 fold more resistant to herbicides selected from Formula 1 or Formula 2 than to herbicides selected from Formula 3 or Formula 4. Alternatively, the plant is transgenic for a similarly derived sequence which is selected on the basis that it comprises a region which encodes an HPPD-inhibitor resistant HPPD enzyme able to form a complex with herbicidal HPPD inhibitors selected from Formula 1 and/or Formula 2 wherein, in water at pH 7.0 and at 25 C, the dissociation of the said complex is governed by a dissociation constant (Kd) in the range 1-30 nM and/or a dissociation rate constant ($k_{off}$) in the range from $4 \times 10^{-5}$ to $2 \times 10^{-3}$ s$^{-1}$ and wherein the selected HPPD-inhibitor has at least a quarter of the herbicidal activity of mesotrione versus dicot plants. In further embodiments the said plant is transgenic in respect of a polynucleotide comprising a DNA sequence which encodes an HPPD-inhibitor resistant HPPD enzyme derived from a plant or, more particularly, derived from a monocot plant or, yet more particularly, from a rice, *Brachiaria, Chenchrus, Lolium, Festuca, Setaria, Eleusine, Sorghum* or *Avena* species. In yet further embodiments the said DNA comprises a sequence selected from the group consisting of SEQ ID NOs 3, 7, 9, 11, 13, 15, 17 and 19.

Plants transformed according to the present inventive method include but are not limited to, field crops, fruits and vegetables such as canola, sunflower, tobacco, sugar beet, cotton, maize, wheat, barley, rice, sorghum, tomato, mango, peach, apple, pear, strawberry, banana, melon, mangelworzel, potato, carrot, lettuce, cabbage, onion, etc. Particularly preferred genetically modified plants are soya spp, sugar cane, pea, field beans, poplar, grape, citrus, alfalfa, rye, oats, turf and forage grasses, flax and oilseed rape, and nut producing plants insofar as they are not already specifically mentioned. In a particularly preferred embodiment of the method the said plant is a dicot, preferably selected from the group consisting of canola, sunflower, tobacco, sugar beet, soybean, cotton, sorghum, tomato, mango, peach, apple, pear, strawberry, banana, melon, potato, carrot, lettuce, cabbage, onion, and is particularly preferably soybean. In further preferred embodiments the said plant is maize or rice. Preferably the plant of the invention is soybean, rice or maize. The invention also includes the progeny of the plant of the preceding sentence, and the seeds or other propagating material of such plants and progeny.

The present invention also includes the use of the DNA sequence referenced above in the production of plant tissues and/or morphologically normal fertile whole plants wherein i) the tolerance of plants to herbicidal HPPD inhibitors is increased, wherein the increase is greater to HPPD inhibitors selected from Formulae 1 or 2 is greater than that to HPPD inhibitors selected from Formulae 3 or 4, or wherein the increase is greater to HPPD inhibitors selected from Formulae 3 or 4 is greater than that to HPPD inhibitors selected from Formulae 1 or 2 and/or (ii) which contain relatively elevated levels of lipid soluble anti-oxidants when compared with non-transgenic such tissues or plants. "Lipid soluble antioxidants" include suitable plastoquinones, α-tocopherols and carotenoids such as the precursors of vitamin A, for example.

The present invention still further provides a polynucleotide comprising transcriptional enhancers and an HPPD inhibitor resistant HPPD enzyme under expression control of its autologous promoter which enzyme is identifiable according to presently disclosed method. Preferably the said HPPD enzyme has the sequence depicted in SEQ ID NO:4. Also included in the invention are plant cells which have been transformed with a polynucleotide sequence which encodes an HPPD inhibitor resistant HPPD enzyme, characterised in that the HPPD encoding sequence is selectable according to presently disclosed methods and/or is derived from an organism selected from the group consisting of Shewenella Colwellina, Vibrio vulnificus, Steptomyces avermitilis and Coccidiodes immitus. Preferably, when the cells are dicot cells the promoter region used to control expression of the HPPD encoding sequence is derived from the small sub-unit of rubisco, and when the cells are monocot cells the promoter region is derived from the maize poly-ubiquitin gene.

The invention will be further apparent from the following description taken in conjunction with the associated sequence listings.

EXAMPLE 1

Cloning of Full and Partial Length 4-HPPD Sequences from Avena and Other Monocot Species Total RNA is prepared from five-day-old Avena Sativa, Brachiaria platyphylla, Cenchrus echinatus, Lolium ridgidum, Festuca arundinacea, Setaria faberi, Eleusine indica and Sorghum sp. seedlings using the method of Tri-Zol extraction (Life Technologies). RT-PCR is performed on each of the RNA samples using the One-step RTPCR kit (Invitrogen) in conjunction with primers HPPD5 (SEQ ID NO:32) and HPPD4R (SEQ ID NO:31). The products obtained are cloned into vector pCR2.1TOPO (Invitrogen) and the cloned products sequenced using standard M13 forward and reverse primers. The sequences obtained are given (or comprised within), for example, SEQ ID NOs. 3, 7, 9, 11, 13, 15, 17 and 19. Messenger RNA is obtained, for example, from Avena sativa using the Oligotex mRNA purification system (Qiagen). The 5' end of, for example, the A. sativa HPPD gene is identified using 5' RACE, performed using the Gene Racer kit (Invitrogen) with gene specific primers (GSP) HPPD RT2 (SEQ ID NO:21) and HPPD RT4 (SEQ ID NO:22). The 3' end of the gene is identified by 3' RACE, performed using Themoscript RT (Life Technologies) with oligo dT primer DT30 (SEQ ID No 23), followed by PCR with GSP HPPD3 (SEQ ID NO:24) and primer DTR (SEQ ID NO:25). All methodologies are performed according to protocols provided by the various stated manufacturers. Products obtained from the 5' and 3' RACE reactions are cloned into pCR 2.1 TOPO (invitrogen) and the cloned products sequenced using universal M13 forward and reverse primers with an automated ABI377 DNA sequencer. Primers 5' Avesal (Seq ID NO:26) and 3' Avesa (Seq ID NO:27) are designed to the translation initiation and termination codons of the HPPD gene (SEQ ID NO:3) respectively. Both primers are used in conjunction with the One-step RTPCR kit (Qiagen) to obtain full length coding sequences. Products obtained are cloned into pCR 2.1 TOPO, sequenced, and identified as 4-HPPD by comparison with sequences known in the art.

EXAMPLE 2

Heterologous Expression of the Pseudomonas fluorescens, Arabidopsis and Wheat 4-HPPD Genes in E. coli The sequences of the Pseudomonas fluorescens strain 87-79 (see WO 98/20144), Arabidopsis (see WO 97/2728) and Wheat 4-HPPD (see WO 00/32757) genes are all known in the art. All three genes are obtained by RT-PCR using primers incorporating suitable restriction enzyme sites in order to allow their cloning into suitable E. coli over-expression vectors, such as the pET (Novagen) series and, for example, as described in Example 3. Heterologous expression of the Pseudomonas HPPD gene in E. coli is also described in WO 98/20144, the contents of which are incorporated herein by reference and heterologous expression of Arabidopsis HPPD in E. coli is also described in Garcia et al in Plant Physiol (1999) 119, 1507-1516) the contents of which are incorporated herein by reference.

EXAMPLE 3

Heterologous Expression of the Avena saliva 4-HPPD Gene in E. coli

The full length A. sativa HPPD gene is excised from the pCR 2.1 TOPO vector, described in example 1, using Nde 1 and Bam H1, and ligated into similarly restricted pET-24a (Novagen). This vector is then transformed into E. coli BL21 (DE3) codon+RP cells (Stratagene). Suitable host strains such as BL21 (DE3) or other DE3 lysogens harbouring the said vector express quantities of HPPD enzyme sufficient to provide for their use in high through put screening to identify alternative 4-HPPD inhibitors. Authenticity of the transformed line is confirmed by PCR, plasmid recovery and restriction analysis. HPPD purified from the said transformed host strain (for example by SDS gel electrophoresis and excision of the band) may be used in the provision of antisera for the analysis of plants transformed with a polynucleotide encoding 4-HPPD.

EXAMPLE 4

Heterologous Expression of Pseudomonas 4-HPPD in Tobacco

The Pseudomonas fluorescens gene from strain 87-79 (SEQ ID NO:1) is edited by PCR to include 5' Nco1 and 3' Kpn1 sites. This product is then ligated into pMJB1. pMJB1 is a pUC19 derived plasmid which contains the plant operable double enhanced CaMV35S promoter; a TMV omega enhancer and the NOS transcription terminator. A schematic representation of the resulting plasmid is shown in FIG. 2 of WO 98/20144. The expression cassette, comprising the double enhanced 35S promoter, TMV omega leader, 4-HPPD gene and nos terminator, is excised using Hind III/Eco R1 (partial Eco R1 digest) and cloned into similarly digested pBIN 19 and transformed into E. coli TOP 10 competent cells.

DNA is recovered from the E. coli and used to transform Agrobacterium tumefaciens LBA4404, and transformed bacteria selected on media contain rifampicin and kanamycin. Tobacco tissue is subjected to Agrobacterium-mediated transformation using methods well described in the art and, optionally, as is described elsewhere herein. Transformed shoots are regenerated from kanamycin resistant callus. Shoots are rooted on MS agar containing kanamycin. Surviving rooted explants are re-rooted to provide approximately 50 kanamycin resistant transformed plants.

EXAMPLE 5

Heterologous Expression of Wheat HPPD Sequence in Tobacco

The wheat HPPD gene is obtained by RT-PCR using primers TAHPPDNde (SEQ ID NO:28) contains an Nde1 site at translation initiation codon or TAHPPDSph (SEQ ID NO:29) contains Sph 1 site at the translation initiation codon and TAHPPDBam (SEQ ID No.30) contains a BamH1 site at translation stop codon. The PCR products are cloned into pCR 2.1, and sequenced to confirm authenticity. The Nde1:BamH1 product is ligated into the vector pMCJA, which is a derivative of pMJB1 (WO 98/20144) and contains an Nde1 site at the translation initiation codon rather than Nco1. The Sph1:BamH1 products are ligated into vector ATSSU1, a pUC derived vector comprising the *Arabidopsis* small sub-unit of rubisco promoter and nos terminator or ATSSU2, a pUC derived vector comprising the *Arabidopsis* small sub-unit of rubisco promoter, an optimised transit peptide and the nos terminator. These gene expression cassettes are all then transferred into suitable binary vectors such as BIN19 (and related vectors) and termed TAHPPD1 (FIG. 1), TAHPPD2 (FIG. 2) and TAHPPD3 (FIG. 3) respectively. These constructs were all transformed into *Agrobacterium tumefaciens* strain LBA4404, which in turn was used to transform tobacco, using methodology described previously.

Explants (i.e. a leaf plus short segment of stem containing the auxiliary bud) are placed into MS agar (+3% sucrose) containing various concentrations of mesotrione (see above) from 0.02 to 2 ppm. In tobacco, for example, untransformed explants are fully bleached at 0.02 ppm. They do not recover following prolonged exposure to the herbicide. In these particular experiments, only the shoot that develops from the bud is bleached, the leaf on the explanted tissue remains green.

A number of the PCR+ve transformed plants tolerate 0.1 ppm of mesotrione (about 5 times the level which causes symptoms on wild-type tobacco, for example) with no indication of bleaching. They root normally and are phenotypically indistinguishable from untransformed plants. A sub-set of the transformants is tolerant to concentrations of >0.2 ppm yielding plants looking normal and rooting well in the presence of herbicide. Some of the transformed plants can be initially bleached when subjected to the herbicide at the said higher concentrations, but on prolonged exposure they progressively "green up" and "recover".

A subset of the said herbicide resistant transgenic plants are treated with the known herbicide Isoxaflutole [5-cyclopropyl-4-(2-methylsulphonyl-4-trifluoromethylbenzoyl)-isoxazole] or, alternatively, the syncarpic acid of structure VI. The said plants are, relative to untransformed controls, resistant to all the herbicides but are, however, substantially less resistant to isoxaflutole, the active principle of which is the diketonitrile (structure IV) a herbicide of Formula 3 or to structure VI a herbicide of Formula 4 than they are to mesotrione, a herbicide of Formula 1 thus clearly indicating that the plants are not fully cross resistant to multiple classes of 4-HPPD inhibitor, which although having the same mode of action are of distinct structural types.

EXAMPLE 6

Heterologous Expression of the *Avena saliva* 4-HPPD Gene in Tobacco

The *Avena sativa* 4-HPPD gene contained within the pCR 2.1 TOPO vector (example 1) is excised from the vector using Nde1 and BamH1 and ligated into similarly digested pMCJA. The structure of the resulting vector is shown schematically in FIG. 4.

The 4-HPPD plant expression cassette is then ligated in to the binary vector pBin19 restricted with Hind III and EcoR1 and transformed into *E. coli* TOP10 cells (Invitrogen). This binary vector is then transformed into tobacco using methods well known in the art and, for example, as described elsewhere herein.

A subset of the said herbicide resistant transgenic plants are treated with the known herbicide Isoxaflutole [5-cyclopropyl-4-(2-methylsulphonyl-4-trifluoromethylbenzoyl)-isoxazole] or, alternatively, the syncarpic acid of structure VI. The said plants are, relative to untransformed controls, resistant to all the herbicides but are, however, substantially less resistant to isoxaflutole, the active principle of which is the diketonitrile (structure IV) a herbicide of Formula 3 or to structure VI a herbicide of Formula 4 than they are to mesotrione, a herbicide of Formula 1 thus clearly indicating that the plants are not fully cross resistant to multiple classes of 4-HPPD inhibitor, which although having the same mode of action are of distinct structural types.

EXAMPLE 7

Production of DNA for Plant Transformation

Linear DNA, suitable for use in bombardment plants transformation, is produced by digesting a vector containing the plant expression cassette with a suitable restriction enzyme(s) to excise the said cassette, which is then purified on an agarose gel and isolated using a Biotrap (Schleicher and Schuell). For *agrobacterium* transformation of soybean or corn the plant expression cassette is subcloned into binary vectors as described in examples 12 and 13.

EXAMPLE 8

In Planta Screening and Selection of Polynucleotides Comprising a Region Encoding an HPPD-inhibitor Resistant HPPD Plants are 1) untransformed tobacco plants variety Samsun expressing the endogenous tobacco (control) HPPD gene, 2) tobacco plants transformed to express *Pseudomonas* HPPD according to the examples herein and 3) tobacco plants transformed to express Wheat HPPD also according to the examples herein.

Large numbers of plants are grown from seed in small pots in the glasshouse to the 5-7 leaf seedling stage and sprayed with a range of doses, suitably from 0.0 to 2000 g/ha, of different HPPD-inhibitor herbicides selected from compounds of Formula 1, 2, 3 and 4. Treatments are suitably Formulated in, for example, deionised water+0.5% Turbo-charge™ surfactant or, alternatively, 50% acetone/water and applied at 200l/ha to a dozen or more replicates of each line and at each spray rate (where the plants were T1 plants (selfed progeny of primary transformants) and still segregating at normally 1:2:1) or, where, homozygous, 3-6 plants. The extent of visible damage in terms of bleaching of meristems and leaves, eventual necrosis and stunting of growth relative to unsprayed controls is assessed at ~1 and 3 weeks after treatment. Data from susceptible segregants are excluded from the analysis. In summary, results obtained are as follows.

Control (untransformed) plants are ~1-2 fold more susceptible of isoxaflutole and ~2-4 fold more susceptible of Structure VI, Structure VII or Structure V than of mesotrione, Structure I. Structure II is of similar potency to isoxaflutole. Plants expressing wheat HPPD are 10-40 fold less susceptible of mesotrione than they are Structure VI or Structure V and also 4-10 fold less susceptible of mesotrione than they are of isoxaflutole. Plants expressing wheat HPPD are 4-15 fold less susceptible of Structure II than they are of Structure V, Structure VI or Structure VII. Plants expressing *pseudomonas fluorescens* HPPD are 2-6 fold more tolerant of isoxaflutole, Structure V, Structure VI or Structure VII than they are of mesotrione or Structure II.

The results demonstrate, inter alia, plants, comprising a test polynucleotide comprising a region encoding a wheat HPPD, which are, for example, >16× more tolerant of structure I, mesotrione, a compound selected from Formula 1 than they are, for example, of structure VI, a compound selected from Formula 4 whereas, for untransformed control plants, the respective difference in tolerance in respect of the same compounds is <4. The ratio of the two, Formula 1/Formula 2 tolerance ratios in respect of test and control plants is, therefore, at least >16/4 which is >2.5 and also >4. Therefore, according to the method, the polynucleotide comprising a region encoding wheat HPPD is screened via transgenesis, regeneration, breeding and spray testing of tobacco and, according to these results, selected as one which encodes an HPPD inhibitor resistant HPPD enzyme. The results also demonstrate, plants, comprising a test polynucleotide comprising a region encoding a *Pseudomonas* HPPD, which are, for example, >2-4× more tolerant of Structure V, Structure VI or Structure VII, compounds selected from Formula 4 than they are, for example, of Structure I, mesotrione, a compound selected from Formula 1 whereas, for untransformed control plants, the respective difference in tolerance in respect of the same compounds is <~0.3-0.5. The ratio of the two, Formula 4/Formula 1 tolerance ratios in respect of test and control plants is, therefore, at least >2/0.5 which is >2.5 and also >4. Therefore, according to the method, the polynucleotide comprising a region encoding a *Pseudomonas* HPPD is screened via transgenesis, regeneration, breeding and spraying of tobacco and thereby selected as one which encodes an HPPD inhibitor resistant HPPD enzyme.

EXAMPLE 9

In vitro Screening and Selection of Polynucleotides Comprising Regions Which Encode HPPD Enzymes Having Kcat/Km Values in the Range from 0.10-5/uM/s Crude extracts of recombinant *E. coli* strains expressing, different test HPPD sequences from, for example, *Arabidopis* Wheat, *Avena Sativa, Pseudomonas* etc and as described elsewhere in the examples are prepared. The recombinant clones are introduced into BL21 (DE3) a codon-optimised RP strain of *E. coli* supplied by Stratagene. The HPPD protein is expressed in this strain following addition of 1 mM IPTG to the fermenter medium (e.g. LB medium supplemented with 100 ug/ml Kanamycin). The recombinant protein of the correct predicted mass is identified (i) on the basis of Coomassie staining of SDS gels of cell extracts and side by side comparison with Coomassie-stained gels of extracts of similar *E. coli* cells transformed with an empty pET24a vector and (ii) by western analysis using a polyclonal antibody previously raised to HPPD polypeptide cut out and eluted from an SDS PAGE gel. Typically, 25 g wet weight of cells are washed in 50 ml of 0.1M Hepes/KOH buffer at pH 7.5. Following low-speed centrifugation, the cell pellet is resuspended in 50 ml of the same buffer. Cells are evenly suspended using a glass homogenizer and then disrupted at 10000 psi using a Constant Systems (Budbrooke Rd, Warwick, U.K.) Basic Z cell disrupter. The crude extract is centrifuged at ~40,000 g for ~2 h and the pellet discarded. Clear supernatant fraction is then exchanged into the same buffer down Sephadex G25 and the, thus prepared extract either used fresh, or beaded into liquid Nitrogen and stored at –80 C until use. Typically, judged from Coomassie dye stained SDS PAGE gels, extracts contained 1-4% of the soluble protein as HPPD. Typically protein concentrations are in the range 15-30 mg/ml and specific activities, based upon using the HPLC assay at 25 C and a substrate concentration of 100 µM HPP are in the range 50-300 nmol of HGA produced/min/mg of protein.

The titre of enzyme inhibitor binding sites in each enzyme preparation is quantitated as follows. A set of reactions are set up in eppendorf centrifuge tubes at ice temperature. A range of volumes of extract, typically from 0 to 50 µl are diluted to a final volume of 250 µl in reaction buffer and the reaction in each tube initiated by addition of a fixed amount of radiolabelled inhibitor. Reaction buffer is suitably, 50 mM Bis-Tris-propane buffer at pH 7.0 containing, (freshly made) 25 mM sodium ascorbate and 2-3.8 mg/l of high-purity catalase (Sigma C3155~50,000 units/mg of protein). Optionally, reaction buffer also contains 25% v/v glycerol. Radiolabelled HPPD inhibitor is suitably labelled with $^{14}C$ at between 0.5 and 3 GBq/mmol and the inhibitor is suitable selected from, mesotrione, the diketonitrile derived from isoxaflutole or 5-methyl-2-(2-Chloro-3-ethoxy-4-methanesulphonylbenzoyl) cyclohexane-1,3-dione. The fixed concentration of radiolabel in each tube is suitably set at 0.1-0.4 µM HPPD inhibitor. In the case of some inhibitor/HPPD enzyme pairs, reactions can be run for i) a relatively short period at 25 C, suitably for 5-15 minutes or ii) for a long period, overnight at 4 C followed by 3-5 h at 25 C in order to achieve, respectively, i) half of the sites or ii) substantially complete occupancy of sites. Those skilled in the art will appreciate that this is a matter of experiment. At the end of the period samples, typically 0.2 ml, of the reaction are taken and rapidly chromatographed down a ~2 ml Pharmacia 'NAP5' gel filtration column and separated into protein-containing (0.8 ml) and protein-free (3 ml) fractions. The two fractions are divided into scintillation vials, scintillation fluid added and the number of counts in each fraction totaled up. Those counts in the protein-containing fraction represent radiolabelled inhibitor bound to protein and those counts in the protein-free fraction represents unbound inhibitor. The purity and radiochemical specific activity of radiolabelled inhibitor is known. Therefore, on the assumption that the inhibitors bind to HPPD in proportions of approximately either 1 or 0.5 per catalytic sites/protein monomer the concentration of inhibitor binding sites and therefore of catalytic sites in the extract can be calculated. Such stoichiometry would be expected for inhibitors which are active-site directed and which mimic catalytic intermediates. By way of further example, the results of some typical experiments are given below.

0, 2, 5, 10, 20, 40 and 60 ul aliquots of a 20 mg protein/ml *Arabidopis* HPPD extract were each incubated with 10 μl (196 Bq) of $^{14}C$ mesotrione (final concentration ~17 μM at ~1.12 GBq/mmol) in a final volume of 240 μl of 50 mM Bis-Tris propane buffer at pH 7.0 and at 25 C containing 25 mM sodium ascorbate and 2-3.8 mg/l of high-purity catalase (Sigma C3155~50,000 units/mg of protein) for 24 h at ice temperature and then at 25 C for ~3.5 h. Pilot experiments indicated that, under such conditions, mesotrione binding would be near complete, the initial ~50% of binding occurring rapidly, the remaining 50% more slowly. 200 μl samples of each reaction were taken and chromatographed down a NAP5 column in order to separate protein-bound from unbound radiolabel and the two fractions counted. The results obtained are depicted in TABLE 1 and expressed in FIG. 5 but, after suitable corrections, with bound dps converted to the μM concentration of bound label in the original reaction. In agreement with TLC and NMR studies, Table 1 indicates that 95% of the radiolabel is mesotrione (as defined by its binding to HPPD) with ~4-5% corresponding to radiolabel contaminants which are not mesotrione and which do not exhibit tight binding to HPPD. The concentration of mesotrione binding sites in the undiluted *Arabidopsis* extract is ~12.2 μM. The polypeptide Mr of *Arabidopsis* HPPD is ~50 kD; thus it can be calculated that HPPD constitutes 3% of the protein of the original crude *Arabidopsis* HPPD extract.

TABLE 1

Titration of *arabidopis* HPPD versus $^{14}C$ mesotrione

| Volume of extract (μl) | bound 14C (dps) | total 14C (dps) | % bound |
|---|---|---|---|
| 0 | 0.3 | 169.9 | 0.0 |
| 2 | 22.95 | 168.9 | 13.6 |
| 5 | 56.48 | 178.23 | 31.7 |
| 10 | 113.3 | 173.1 | 65.5 |
| 20 | 152.3 | 166.25 | 91.6 |
| 40 | 157.6 | 168 | 93.8 |
| 60 | 158.7 | 168.1 | 94.4 |

It will be apparent to those skilled in the art that essentially the same methods can be used to measure the titre of inhibitor-binding sites in extracts of other HPPD enzymes. Thus, for example, an extract of HPPD at from wheat at 24 mg protein/ml is determined to contain ~20+/-~4 μM binding sites for $^{14}C$-labelled diketonitrile or $^{14}C_5$-methyl-2-(2-Chloro-3-ethoxy-4-methanesulphonylbenzoyl)-cyclohexane-1,3-dione. For wheat, the first inhibitor molecule binds more quickly, the second more slowly and the error range is higher than for *Arabidopsis* HPPD because the wheat enzyme is somewhat less stable and loses its binding capacity more quickly. Wheat HPPD (and indeed all HPPD enzymes) is stabilised by inhibitors and most stabilised by those inhibitors which bind the tightest to it. Such inhibitors are the best choice for measuring the titre of inhibitor binding sites.

The HPLC assay for HPPD activity and the determination of kcat and Km is conducted as follows. Assay buffer is 105 μM (or as appropriate) hydroxyphenylpyruvate (HPP) is freshly made up in 50 mM Bis-Tris-propane buffer at pH 7.0. Dilution buffer is 50 mM Bis-Tris-propane buffer at pH 7.0 containing 25 mM sodium ascorbate and 3.8 mg/l of bovine catalase (Sigma C3155~50,000 units/mg). HPPD enzyme, freshly unfrozen from storage is kept at ice temperature and diluted, also at ice temperature, to an appropriate concentration in dilution buffer (typically, 2-8 μM) before use. Assays are started by addition of 5 μl of diluted enzyme to 100 μl of assay buffer at 25 C in an eppendorf centrifuge and stopped, at a series of times between 0 and 90 s by addition of 20 μl of 25% perchloric acid and whirlimixing. 80-100 μl of the contents of each eppendorf tube is transferred to an HPLC vial prior to separation by Reverse Phase HPLC. For HPLC, 40 μl is loaded at 1.5 ml/min onto an Aqua C18 5μ 75×4.6 mm column (silica is endcapped) equilibrated with 5.5% acetonitrile, 0.1% trifluoroacetic acid (buffer A) using an HP 1100 HPLC system. The column is eluted, also at 1.5 ml/min, using a 2 minute wash with buffer A, followed by a 2 min wash with a 30/70 mixture of buffer A/100% acetonitrile followed by a further 3.5 minute wash with buffer A (in between uses the column is stored in 65% acetonitrile/water). The elution of HGA (homogentisic acid) and HPP (hydroxyphenylpyruvate) is monitored using a UV flow cell and quantitated via integration of peak absorbance at 292 nm. HGA elutes at around 2 minutes and HPP elutes later. A standard set of concentrations of HGA are used to provide a standard curve in order to calibrate the UV absorbance of the HGA peak versus HGA concentration.

The assay is used to provide estimates of the Km and Vmax values of typical HPPD preparations. For Km determinations it is important to obtain near initial rate data which, for stopped assays, becomes more critical at lower substrate concentrations. Thus it is important to take a number of time-points for each substrate concentration and to use early time point data at low substrate concentrations. An example of an experiment to determine the Km and Vmax value for the wheat HPPD is provided in TABLE 2.

TABLE 2

Wheat HPPD assayed at different times (s) and HPP concentrations Data are amounts of HGA formed (pmol). The stock wheat HPPD extract (18 μM) was diluted 30 fold. The assay, final volume 105 μl contained 5 μl of diluted HPPD.

| TIME (s) | 5 | 15 | 25 | 35 |
|---|---|---|---|---|
| | | HPP concn. μM | | |
| 3 | 44 | 129 | 182 | 207 |
| 6 | — | 186 | 282 | 389 |
| 8 | 55 | 220 | 347 | 462 |
| 12 | 68 | 245 | 417 | 556 |
| 20 | 113 | 352 | 479 | 777 |
| 60 | 133 | 427 | 700 | 963 |

The Km value for the wheat HPPD with respect to the substrate HPP is about 10.1+/−1.5 μM. Vmax is 33.5+/−4 pmol/s. From the active-site titration the concentration of wheat HPPD in the assay is calculated to be 31.5 nM corresponding to 3.1 pmol. of enzyme sites in 105 μl. The kcat and kcat/Km values for wheat HPPD can therefore be calculated as ~11/s and ~1.1/s/μM, respectively. Similarly, it is determined that the kcat, Km and kcat/Km values of *Arabidopsis* HPPD are ~4.65/s, 3.5 μM and 1.3/s/μM, respectively and also that the kcat, Km and kcat/Km values of w/t *Pseudomonas fluorescens* HPPD are ~5.04/s, 32 μM and 0.16/s/μM, respectively. The mutant form of *Pseudomonas fluorescens* HPPD having a tryptophan at position 336 is found to have a kcat/Km value at least 3 fold reduced relative to that of the wild-type (kcat/Km<~0.05/s/μM). It can be further calculated that the specific activities of the pure wild-type *Pseudomonas* (subunit Mr~40223), *Arabidopsis* (subunit Mr~46486) and wheat enzymes (subunit Mr48923) at 25 C and with saturating substrate are, at least, 7.13, 5.7 and ~13.5 mmol/min/mg protein which are values much higher than previously known for HPPD enzymes; these values increase yet further by 20-30% when it is further taken into account that 20-30% of the binding to the 'fast exchanging' fraction of sites (vide infra) which quite possibly represents binding to damaged enzyme, or, sites otherwise unrelated to catalytic activity.

Therefore, according to this example a polynucleotide comprising a region encoding, for example, a wheat HPPD is screened via a method comprising heterologous expression in a bacterium, preparation of an extract containing the expressed HPPD in an active form, determination of the active site concentration through titration versus a tight-binding active-site directed inhibitor and performing enzyme assays at a range of substrate concentrations. It is selected as a polynucleotide, useful in the context of the current invention, which encodes a suitably resistant HPPD enzyme because the value of kcat/Km calculable from the data so obtained is ~1.0/s/µM at pH 7.0, 25° C. which is within both the claimed range of 0.1 to 5 $s^{-1}µM^{-1}$ and the preferred range of 0.8 to 5 $s^{-1}µM^{-1}$.

EXAMPLE 10

In vitro Screening and Selection of Polynucleotides Comprising Regions which Encode HPPD-Inhibitor Resistant HPPD Enzymes Based Upon Measurement of the Relative and Absolute Values of Rate Constants Governing the Dissociation of Enzyme/Inhibitor Complexes Crude extracts of recombinant *E. coli* strains expressing, in the one case, a control HPPD (from *Arabidopsis*) and, in the other, one or more a test HPPD sequences are prepared as described in the preceding example. The titre of active sites and enzyme activity are also defined and measured as described in the preceding examples.

The dissociation rates (off rates) of inhibitors selected from Formula 1 and/or 2 and/or 3 and/or 4 from the complexes that they form with test and control HPPD enzymes are suitably measured in a number of ways. Thus, for example, the rates of dissociation of mesotrione, a compound selected from Formula 1 and of the diketonitrile of isoxaflutole, a compound selected from Formula 3 from their respective complexes with, test, wheat HPPD and with, control, *Arabidopsis* HPPD are compared. The method and results from a typical test are as follows.

$^{14}$C mesotrione is of specific activity 1.12 GBq/mmol. This is ~95% pure radiochemically by TLC and based upon the proportion of material tight-binding to HPPD. *Arabidopsis* and, (test), wheat HPPD are each diluted to a concentration of ~0.45 and 0.54 µM, respectively into 1.6 ml of 50 mM Bis-Tris propane buffer at pH 7.0 containing 25% glycerol, 25 mM sodium ascorbate and 3 mg/l of bovine catalase (Sigma C3155~50,000 units/mg) containing 0.46 mM $^{14}$C mesotrione and left to react at 25 C for 2.5-3 h. Following this initial binding reaction, exchange reactions are initiated by addition of cold mesotrione to a final concentration of 60 µM and 200 µl aliquots removed at various times to rapid chromatography down a NAP5 gel filtration column equilibrated in 50 mM BTP at pH 7 containing 0.1 M KCl, separation into fractions containing protein-bound or free radiolabel and liquid scintillation counting. Results are summarised in FIG. 1 in which in control experiments, where no cold mesotrione is added, the inhibitor remains substantially bound.

The concentration of bound mesotrione (vertical axis) at zero time (~0.35 µM) in FIG. 1 is somewhat less than either the concentration of *Arabidopsis* enzyme (~>0.43 µM) or, in the case of wheat which was in excess, of the inhibitor (~0.46 µM). This is because, after 2.5 to 3 h at 25 C binding is not fully complete (~0.5 equivalents of mesotrione bind quickly, the remainder binds slowly) and the rate is somewhat slowed by the presence of 25% v/v glycerol. It is also apparent that ~25% of the mesotrione bound to *Arabidopsis* HPPD exchanges relatively rapidly whereas the rest exchanges slowly. In crude extracts of *Arabidopsis* as well as other HPPD enzymes it is routinely found that approximately 20-30% of bound mesotrione exchanges relatively rapidly (t½±30-40 min for dissociation of mesotrione from *Arabidopsis* HPPD at 25 C, pH 7.0 in 20-25% v/v glycerol) whereas 70-80%, presumed here to correspond to the bulk of genuine fully active enzyme exchanges slowly (t ½~4 d for dissociation of mesotrione at 25 C, pH 7.0 in 20-25% v/v glycerol). This is supported by 1) the observation that further enzyme handling associated with activity loss leads to a relative increase in the proportion of the rapid exchanging fraction and 2) the preliminary observation that the relative proportion of the fast exchanging fraction does not, on the other hand, vary according to the time of the binding reaction (10 s to 24 h) and, is not, therefore, a kinetically trapped intermediate in the binding reaction. The notion that the fast exchanging fraction merely represents damaged enzyme is further supported by the observation that the proportion of the rapidly exchanging fraction is diminished or not observed when experiments are carried out with an excess of HPPD. The origin of the fast exchanging fraction is not entirely clear and remains open to speculation. Nevertheless, here, for practical purposes, $k_{off}$ values are always here calculated from the rate of the major slow exchange reaction. Such $k_{off}$ values are calculated by computer modelling to obtain a best fit of the data to the computed progress of an EI+I*↔EI*+I exchange reaction governed by four rate constants (but where the two $k_{on}$ values are assumed to be the same as each other as are the two $k_{off}$ values) and using $k_{on}$ values as independently determined in the further examples (the accuracy of $k_{on}$ values, not, in any case, generally being critical for such fits). It is clear that mesotrione dissociates rapidly from the test, wheat, HPPD but much more slowly from the, control, *Arabidopsis* HPPD. The data are best fit to $k_{off}$ values for mesotrione of ~3.8×10$^{-4}$/s from wheat HPPD and 2.0×10$^{-6}$/s from *Arabidopis* HPPD ($k_{on}$ values in the two cases, in the presence of glycerol, being 7×10$^4$/s/M and 1.1×10$^5$/s/M, respectively).

Not all test inhibitors are readily available in a radiolabelled form. A more general method of measuring off rates is to first form the complex with unlabelled test inhibitor, to rapidly exchange the complex free of excess unlabelled inhibitor and to then start the exchange reaction by addition of an excess of a standard labelled inhibitor, the kinetic properties of which are already known. The reaction is then monitored and the relative proportions of bound and unbound label determined at various times. It is found that $k_{off}$ values so obtained from monitoring the forward rate of exchange of labelled inhibitor binding onto HPPD are, as expected, generally very close to the values obtained from monitoring the reverse, which is the exchange of labelled inhibitors from the complex with HPPD. The latter is the method of choice when the rate of exchange is fast (t ½<3 h).

Apart from $^{14}$C mesotrione (structure I) (specific activity 1.12 GBq/mmol as used here), $^{14}$C structure III (specific activity 1.036 GBq/mmol as used here) and $^{14}$C 5-methyl-2-(2-Chloro-3-ethoxy-4-methanesulphonylbenzoyl)-cyclohexane-1,3-dione (1.81 GBq/mmol as used here) are suitably used as standard inhibitors. Preferably whichever standard inhibitor is found to bind the tightest (has the lowest Kd value) to a given HPPD is used as the standard inhibitor in respect of that HPPD for the evaluation of the Kd and $k_{off}$ values of unlabelled inhibitors.

The method and results which follow illustrate the method for measuring the $k_{off}$ values of unlabelled inhibitors. *Arabi-*

*dopsis* HPPD is diluted to 2.76 µM in 50 mM Bis-Tris propane buffer at pH 7.0 containing 25 mM sodium ascorbate, 2 mg/l of bovine catalase (Sigma C3155~50,000 units/mg) and 20 µM of test inhibitor, in this case, mesotrione or structure II. This initial binding reaction with unlabelled inhibitor is left overnight at ice temperature and then for 2-3 h at 25 C. 200 µl is then quickly exchanged free of unbound inhibitor by gel filtration down a Pharmacia NAP5 column and dilution into 1.5 ml of 50 mM Bis-Tris propane buffer at pH 7.0 containing 25 mM sodium ascorbate and 2 mg/l of bovine catalase (Sigma C3155~50,000 units/mg). The exchange reaction is started by addition of 80 µl of $^{14}C$ mesotrione to a final concentration of 1.75 µM and aliquots removed at various times for rapid gel filtration down a NAP5 column equilibrated in 50 mM BTP at pH 7 containing 0.1 M KCl, separation into protein-bound and protein-free fractions and liquid scintillation counting. Results are summarised in FIG. 2. in which triangles represent data from unlabelled mesotrione, circles represent data from structure II. In control experiments, where the enzyme is pre-incubated with either no unlabelled inhibitor or, preferably, with a weak inhibitor such as in structure VIII, the radiolabelled inhibitor is fully bound within a period of 5-6 h (to a concentration of 0.385 µM in the particular example of the experiment depicted in FIG. 2) and remains substantially fully bound for a period of days (the amount bound declining by ~5-7%/d corresponding to gradual deterioration of the *Arabidopsis* HPPD enzyme). Concentrations of bound on the vertical axis are normalised with respect to the control values in order to take into account this gradual loss of binding capacity. The graphs obtained are the inverse of the type depicted in FIG. 1. Again, the data are consistent with ~20% of the HPPD binding sites being in relatively rapid exchange with an initial phase of more rapid binding occurring first. In addition, in the controls, binding equilibrium is not full established until after 4-6 h. $k_{off}$ values are always here calculated from the rate of the major slow exchange reaction, which occurs after this period. Such $k_{off}$ values are calculated by computer modelling to obtain a best fit of the data to the computed progress of an EI+J ⇄ EJ+I exchange reaction governed by four independent rate constants and using $k_{on}$ values as independently determined in the further examples. Thus, for example, from the data in FIG. 2 it is clear that structure II dissociates more rapidly from *Arabidopsis* HPPD than does mesotrione. The data are best fit to $k_{off}$ values, obtained in this case without 25% v/v glycerol present, of $1.16 \times 10^{-5}/s$ ($k_{on}=0.8/s/\mu M$) and $3.3 \times 10^{-6}/s$ ($k_{on}=1.9/s/\mu M$) from arabidopis HPPD.

In, variants of the above methods, off rates are measured either in the presence or absence of ~25% v/v glycerol. In the presence of glycerol values obtained are generally ~1.5-3× slower than in its absence although sometimes the change is outside this range or, even, in the other direction. Further examples of data obtained are depicted in the following Table 3.

TABLE 3

Dissociation rate constants, ($k_{off}$ values) governing dissociation of various inhibitors from complexes with various HPPD enzymes. Each line represents data from a separate single experimental set.

| Inhibitor Structure | *Arabidopsis* HPPD. $k_{off}(s^{-1})$ – glycerol ($k_{off}(s^{-1})$ + glycerol) | Wheat HPPD $k_{off}(s^{-1})$ – glycerol ($k_{off}(s^{-1})$ + glycerol) | *P. fluorescens* HPPD $k_{off}(s^{-1})$ – glycerol ($k_{off}(s^{-1})$ + glycerol) |
|---|---|---|---|
| I | $3.3 \times 10^{-6}$ ($2.0 \times 10^{-6}$) | $1.0 \times 10^{-3}$ ($3.8 \times 10^{-4}$) | $2 \times 10^{-6}$ ($8 \times 10^{-6}$) |
| II | $1.16 \times 10^{-5}$ $8.6 \times 10^{-6}$ | $2.5 \times 10^{-4}$ $3.5 \times 10^{-4}$ | — $5 \times 10^{-5}$ |
| III | $1.1 \times 10^{-5}$ | $>2.0 \times 10^{-4}$ | |
| IV | ($1.6 \times 10^{-6}$) $8.3 \times 10^{-6}$ | ($1.66 \times 10^{-5}$) $6.2 \times 10^{-5}$ | ($4.2 \times 10^{-5}$) $1.8 \times 10^{-4}$ |
| V | $1.25 \times 10^{-6}$ ($2.7 \times 10^{-7}$) | $4.2 \times 10^{-6}$ | $>2 \times 10^{-4}$ |
| VI | $2.0 \times 10^{-6}$ | $2.5 \times 10^{-5}$ | $>4 \times 10^{-4}$ |
| VII | $1 \times 10^{-6}$ | $8.3 \times 10^{-6}$ | $>3 \times 10^{-4}$ |

Thus it can be seen, inter alia, that, according to the method, polynucleotides comprising a region which encodes an HPPD enzyme are screened via a process of expression and testing in vitro in respect of HPPD enzyme/HPPD inhibitor dissociation rates ($k_{off}$ values). It can be further seen from the above example that a polynucleotide comprising a region which encodes wheat HPPD is selected as one which encodes an inhibitor-resistant HPPD because it is found that the ratio ($k_{off}1/k_{off}3$) of the value of $k_{off}$ for the complex of the expressed wheat HPPD with structure I (a compound selected from Formula 1) to that for the complex formed with structure IV (a compound selected from Formula 3) is 22.9 or 16.13 which is >>2.5 fold more than the likewise derived ratio of 1.25 or 0.38 observed in respect of dissociation of the same pair of inhibitors from *Arabidopsis* control enzyme. As can be seen, the screening and comparison could equally as well have been made, for example, in respect of structure II (a compound selected from Formula 2) and structure VII (a compound selected from formula 4) with the same result that a polynucleotide comprising a region which encodes wheat HPPD is selected. In this case, the ratio, $k_{off}2/k_{off}4$ in respect of wheat HPPD is 30 or 42 which, again is >2.5 fold more than the equivalent ratio of 11 or 8.6 in respect of the *Arabidopsis* control enzyme. Alternatively, a polynucleotide comprising a region which encodes wheat HPPD is screened and selected on the basis that it encodes an HPPD-inhibitor resistant HPPD enzyme able to form a complex in water at pH 7.0 and at 25 C with a herbicidal HPPD inhibitor, in this case structure I or structure II, wherein the dissociation of the said complex is governed by a rate constant ($k_{off}$) in the range from $4 \times 10^{-5}$ to $2 \times 10^{-3}$ $s^{-1}$ (in this case, $3.8 \times 10^{-4}$ or $1.0 \times 10^{-3}$ and $2.5 \times 10^{-4}/s$ or $3.5 \times 10^{-4}$, respectively) and wherein the selected HPPD-inhibitor has at least a quarter of the herbicidal activity of mesotrione versus dicot plants (this being true of structure II as, obviously, of mesotrione itself).

Alternatively, the example illustrates that, according to the method, a polynucleotide comprising a region which encodes *Pseudomonas* HPPD is selected as one which encodes an inhibitor-resistant HPPD because it is found that the ratio ($k_{off}4/k_{off}1$) of the value of $k_{off}$ for the complex of the expressed *Pseudomonas* HPPD with structure VI (a compound selected from formula 4) to that for the complex formed with structure I (a compound selected from formula 1) is >21.7 or >100 which is >>2.5 fold more than the likewise derived ratio of 0.6 observed in respect of dissociation of the same pair of inhibitors from *Arabidopsis* control enzyme. As can be seen, the screening and comparison could equally as well have been made, for example, in respect of structure IV (a compound selected from formula 3) and structure I (a compound selected from formula 1) with the same result that a polynucleotide comprising a region which encodes *Pseudomonas* HPPD is selected. In this case, the ratio, $k_{off}3/k_{off}1$ in respect of *Pseudomonas* HPPD is 5.25 or 90 which, again is >2.5 fold more than the equivalent ratio of 0.8 or 2.5 in respect of the *Arabidopsis* control enzyme. Alternatively, a polynucleotide comprising a region which encodes *Pseudomonas* HPPD is screened and selected on the basis that it encodes an HPPD-inhibitor resistant HPPD enzyme able to form a complex in water at pH 7.0 and at 25 C with a herbicidal HPPD inhibitor, in this case structure IV or structure VI, wherein the dissociation of the said complex is governed by a rate constant ($k_{off}$) in the range from $4 \times 10^{-5}$ to $2 \times 10^{-3}$ s$^{-1}$ (in this case, $4.2 \times 10^{-5}$ or $1.8 \times 10^{-4}$ and >$2.0 \times 10^{-4}$/s, respectively) and wherein the selected HPPD-inhibitor has at least a quarter of the herbicidal activity of mesotrione versus dicot plants (this being true of both structure IV and VI).

EXAMPLE 11

In vitro Screening and Selection of Polynucleotides Comprising Regions which Encode HPPD Enzymes Based Upon Measurement of the Relative and Absolute Values of the Dissociation Constants (Kd Values) of Enzyme/Inhibitor Complexes.

Qualitative measurements of the differences in Kd values in respect of different HPPD inhibitors are obtained by pre-incubating enzyme with inhibitor and, then, subsequently, measuring the % inhibition. For example HPPD is isolated from maize seedlings, part purified and assayed by similar methods to those described by Schulz et al 1993 (FEBS LETS. 318, 162-166) and by Secor (1994) in Plant Physiol. 106, 1429-1433. Assays are run for 30 minutes and started with addition of radiolabelled hydroxyphenylpyruvate (final concentration ~0.1-0.2 mM) following a 20-30 min period over which inhibitor is pre-incubated with the part-purified enzyme. The following levels of inhibition (relative to controls) are observed with the following doses of herbicide versus maize HPPD

|  | mesotrione | sulcotrione | structure IV |
|---|---|---|---|
| 1 nM | <17% | — | 44% |
| 10 nM | 44% | 8% | 78% |
| 100 nM | 51% | 51% | 92% |
| 1000 nM | >75% | 83% | 93% |

Using the same assay method but using HPPD from *Arabidopis* (obtained from *E. coli* cells transformed to express the *Arabidopsis* HPPD and prepared as an *E. coli* extract similar to the methods described by Garcia et al in Plant Physiol (1999) 119, 1507-1516) the following levels of inhibition (relative to controls) are observed with the following doses of herbicide versus *Arabidopsis* HPPD.

|  | mesotrione | sulcotrione | structure IV |
|---|---|---|---|
| 1 nM | 42% | 57% | 20% |
| 10 nM | 95% | 96% | 90% |
| 100 nM | 100% | 100% | 95% |
| 1000 nM | 100% | 100% | 95% |

The experiment indicates that structure IV is a similar or somewhat less potent inhibitor of *Arabidopis* HPPD than mesotrione and sulcotrione (which appear ~10 and 100 fold less active against the maize enzyme than structure IV). These data demonstrate that some substituted 1,3 cyclohexane dione herbicides such as sulcotrione and mesotrione have, as at least a part of the basis of their observed selectivity, a tendency to inhibit HPPD from monocotyledonous plants less strongly than that from dicotyledenous plants. In order to obtain quantitative measurements of absolute and relative Kd values methods are used as described below.

Crude Extracts of recombinant *E. coli* strains expressing, in the one case, a control HPPD (from *Arabidopsis*) and, in the other, one or more test HPPD sequences are prepared as described in the preceding example. The titre of active sites and enzyme activity are also defined and measured as described in the preceding examples. The dissociation rates (off rates) of inhibitors selected from formula 1 and/or 2 and/or 3 and/or 4 from the complexes that they form with test and control HPPD enzymes are suitably measured as described in the preceding examples. Kd values are suitably calculated from the ratio $k_{off}/k_{on}$. In variants of the method, on rates and off rates are both measured in the presence of ~25% v/v glycerol or, both are measured in its absence. Generally glycerol appears to slow on and off rates to about the same extent and therefore Kd values often do not appear to vary with glycerol. On some occasions though Kd is glycerol dependent. Rate constants ($k_{on}$ values) governing the rate of binding of inhibitors to HPPD enzymes are suitably measure in a number of ways.

Firstly HPLC assays monitoring the formation of HGA at various times are run as described the preceding example 9. Even in the absence of added inhibitors, progress curves are not linear reflecting progressive inactivation of the enzyme under assay conditions. At increasing concentrations of inhibitor the curvature becomes much more marked. It is possible to fit both control and inhibited curves to a simple exponential decay in the amount of active enzyme from the starting concentration toward a final level of zero (i.e. a decline in the concentration of active enzyme governed by a process where $E(t)=E(o).e^{-kt}$. Thus, apparent rate constants (k') at a range of different concentrations of inhibitor are derived by subtracting the control rate constant fitted to the progress curve in the absence of inhibitor from the observed rate. Estimates of true rate constants ($k_{on}$) are then derived by multiplying apparent rate constants, k', by 1/(1+S/Km) where S is the concentration of HPP in the assay. Given the need for curve subtraction and to know the value of Km this is probably the least accurate of the various methods of determining $k_{on}$. Nevertheless it is valuable since it provides a direct test of the presumption, implicit in the calculation, that inhibitor binding can be adequately described by a simple E+I⇌EI binding process rather than a more complex scheme involving the initial rapid formation of a rapidly dissociable enzyme inhibitor complexes which then slowly isomerizes to a more tightly inhibited form. In the latter case, rather than zero inhibition at near zero time, a significant level of initial inhibition is seen (Schloss, J. V. (1989) in "Target sites of Herbicide Action" (Boger, P. and Sandmann G. eds) CRC Press Boca). An example experiment is illustrated in FIG. 3.

In FIG. 3 assays containing 100 µM HPP substrate were started with addition of wheat HPPD to a final concentration of ~19 nM and stopped at the times indicated. The upper progress curve is with no inhibitor present, the middle with 2.5 µM and the lower with 10 µM of structure II present; these curves are fit to an initial rate of 0.35 µM/s (i.e. there is no significant initial inhibition) with observed first order decay rate constants of 0.016, 0.029 and 0.06/s, respectively. Assuming a Km value of 10 µM, the value of $k_{on}$ is therefore estimated as between 48000 and 57200 $s^{-1}M^{-1}$.

In a more direct assay-based method for measuring $k_{on}$ values, test HPPD enzyme is reacted with inhibitor for a range of times and then the inhibition reaction is effectively stopped by addition of a high concentration of the (competitive) substrate HPP. At the same time as effectively freezing further inhibition this also starts the assay which indicates how far inhibition had proceeded during the period before the HPP was added. The following example illustrates the method. Wheat HPPD is diluted to a concentration of 0.465 µM in 50 mM Bis-Tris propane buffer at pH 7.0 containing 25 mM sodium ascorbate and 3.9 mg/l of bovine catalase (Sigma C3155~50,000 units/mg). 5 µl of diluted HPPD is added to, alternatively, 10 µl of 50 mM BTP buffer at pH 7.0 (control), 10 LI of 50 mM BTP buffer at pH 7.0 containing 0.5 µM structure VI or 10 µl of 50 mM BTP buffer at pH 7.0 containing 2.0 µM structure VI. The reactions are left to run for alternative times of 0 ('pre-stopped' assay), 10, 30, 50 or 70 s at 25 C before addition of 100 µl of 150 µM HPP. After addition of HPP, assays are run for 40 s before stopping with addition of 20 µl of 25% perchloric acid and analysis by HPLC. In the timed 'pre-reactions' between enzyme and inhibitor the concentration of enzyme is 0.155 µM that of inhibitor, alternatively, 0, 0.33 µM and 1.33 µM. Note that, because the initial, fast, reaction of inhibitors with HPPD which results in complete loss of activity is with only half the sites ultimately measurable by binding stoichiometry, the relevant enzyme concentration here for simulation and for calculation of rate constants is half the enzyme concentration as measured in long-term titration binding studies as described above. In the assays run for 40 s, the maximum final concentration of inhibitor is 0.174 µM. It is confirmed through experiments such as that described for FIG. 3 that, especially in the presence of 130 µM HPP, this is far too little to cause any detectable progressive inhibition during the course of the 40 s assay itself and, thus, that all the inhibition observed is due to inhibitor binding to enzyme occurring during the timed pre-reaction in the absence of substrate. The data obtained are fit to a model E+I → EI reaction wherein 'activity' is equivalent to 'active enzyme' and the decline in activity mirrors the decline in the species 'E' after addition of inhibitor. Given the relatively very low values of off rates it can be assumed that the inhibition reaction is effectively irreversible under the reactions conditions (it makes no significant difference if the reaction is modelled as a reversible one and the known low off rates are included in the fit). The results from the experiment and fit to the data are illustrated in FIG. 4. The upper graph represents the rate of enzyme in activation at 0.33 µM structure VI, the lower graph, the rate at 1.33 µM. Both curves are fit to a rate constant ($k_{on}$) value of 70,000 $M^{-1}s^{-1}$.

The measurements of $k_{off}$ are based on physical rather than assay-based measurements. Similarly, $k_{on}$ rates can also be measured by a direct physical method, in this case the use of radiolabelled inhibitor and physical separation of protein bound from free inhibitor. It is useful to obtain the correlation between physical binding and assay-based methods because, for example, it can show, especially where physical binding indicates, initially, only 'half of the sites' binding that this, nevertheless, occurs contemporaneously with the loss of all of the enzyme activity. The rates of binding determined on the basis of measurement of the amount of radiolabelled inhibitor bound after various times of reaction are found to correlate very well with measurements based upon assay-based measurements of the rate of decline of enzyme activity. Furthermore it is also found that measurements of $k_{off}$ based upon exchange studies as described elsewhere herein yield similar results independently of whether or not the initial binding reaction to form enzyme inhibitor complex is stopped after 10 s (such that the reaction is only partly complete) or after 10 h, confirming that the on rates and off rates which are measured relate to the same species of enzyme/inhibitor complex (rather, for example, than there being an initial weak inhibited complex for which we measure on rates which isomerises slowly to a tighter-bound complex for which we measure off rates) and thus, the two values can be validly combined to yield values of Kd.

An illustrative example of an experiment to measure the on rate of mesotrione binding to *Arabidopsis* HPPD follows. A series of eppendorf centrifuge tubes are set up at 25 C containing $^{14}$C mesotrione in 50 mM Bis-Tris propane buffer at pH 7.0 containing 25 mM sodium ascorbate, 25% v/v glycerol and 3.0 mg/l of bovine catalase (Sigma C3155~50,000 units/mg). Reactions are started by addition of *Arabidopsis* HPPD such that the final concentrations of *Arabidopsis* HPPD and $^{14}$C mesotrione are, ~0.30 µM and 0.347 µM, respectively, mixed and rapidly stopped after various time intervals by addition of a large excess of unlabelled mesotrione to a final concentration of 170 µM. After stopping samples are quickly separated into protein-bound and protein-free fractions by rapid Gel filtration down a NAP5 Pharmacia column equilibrated in 50 mM BTP at pH 7 containing 0.1 M KCl and the radioactivity in the two fractions measured by liquid scintillation counting. Results obtained and the fitting of data are illustrated in FIG. 5.

The data of FIG. 5 are fit to a rate constant, $k_{on}$ value of 125000 $M^{-1}s^{-1}$ with only half of the *Arabidopsis* sites binding mesotrione. There is a subsequent much slower reaction not shown (fit to a rate constant of ~1000 $M^{-1}s^{-1}$) in which mesotrione binds to the remaining inhibitor site. Inhibitor/HPPD combinations are found to vary in whether or not only half the sites are bound initially. In either case it is only the initial rate, as depicted in FIG. 5, which is taken to be the value of $k_{on}$. In a similar experiment to FIG. 5 but in the absence of glycerol the value of $k_{on}$ is found to be 190000 $M^{-1}s^{-1}$. This value is indistinguishable from the value of ~250000 $M^{-1}s^{-1}$ found using assay based measurements of the rate of activity loss. Similar binding experiments indicate, for example, a value of 100000 $M^{-1}s^{-1}$ for the rate constant, $k_{on}$, governing the association of structure IV with *Arabidopsis* HPPD in the presence of glycerol. The, above-described, methods for the measurement of $k_{on}$ and $k_{off}$ values allow calculation of Kd values, some of which are illustrated in Table 4.

TABLE 4

Dissociation constants, (Kd values) governing dissociation of various inhibitors from complexes with various HPPD enzymes

| Inhibitor Structure | Arabidopsis HPPD. Kd (pM) (value obtained + glycerol) | Wheat HPPD Kd (pM) (value obtained + glycerol) | P. fluorescens HPPD Kd(pM) (value obtained + glycerol) |
|---|---|---|---|
| I | 14 (27) | 7407 (6333) | 114 (200) |
| II | 110 | 6727 | 2174 |
| III | | | |
| IV | 46 (17) | 885 (596) | 12200 (1100) |
| V | 4 | 11 | >1500 |
| VI | 25 | 450 | >20000 |
| VII | 32 | 175 | |

Thus it can be seen, inter alia, that, according to the method, polynucleotides comprising a region which encodes an HPPD enzyme are screened via a process of expression and testing in vitro in respect of HPPD enzyme/HPPD inhibitor dissociation constants (Kd values). It can be further seen from the above example that a polynucleotide comprising a region which encodes wheat HPPD is selected as one which encodes an inhibitor-resistant HPPD because it is found that the ratio (Kd1/Kd3) of the value of Kd for the complex of the expressed wheat HPPD with structure I (a compound selected from formula 1) to that for the complex formed with structure IV (a compound selected from formula 3) is 83.7 or 14.3 which is >>2.5 fold more than the likewise derived ratio of 0.3 or 1.1 observed in respect of dissociation of the same pair of inhibitors from Arabidopsis control enzyme under the same conditions. As can be seen, the screening and comparison could equally as well have been made, for example, in respect of structure II (a compound selected from formula 2) and structure VII (a compound selected from formula 4) with the same result that a polynucleotide comprising a region which encodes wheat HPPD is selected. In this case, the ratio, Kd2/Kd4 in respect of wheat HPPD is 38 which, again is >2.5 fold more than the equivalent ratio of 3.4 in respect of the Arabidopsis control enzyme. Alternatively, a polynucleotide comprising a region which encodes wheat HPPD is screened and selected on the basis that it encodes an HPPD-inhibitor resistant HPPD enzyme able to form a complex in water at pH 7.0 and at 25 C with a herbicidal HPPD inhibitor, in this case structure I or structure II, wherein the dissociation of the said complex is governed by a dissociation constant (Kd) in the range from 1.0 to 30 nM (in this case, ~6.5-7.5 nM) and wherein the selected HPPD-inhibitor has at least a quarter of the herbicidal activity of mesotrione versus dicot plants (this being true of structure II as, obviously, of mesotrione itself).

Alternatively, the example illustrates that, according to the method, a polynucleotide comprising a region which encodes Pseudomonas HPPD is selected as one which encodes an inhibitor-resistant HPPD because it is found that the ratio (Kd3/Kd1) of the value of Kd for the complex of the expressed Pseudomonas HPPD with structure IV (a compound selected from formula 3) to that for the complex formed with structure I (a compound selected from formula 1) is 107 which is >2.5 fold more than the likewise derived ratio of 3.3 observed in respect of dissociation of the same pair of inhibitors from Arabidopsis control enzyme. As can be seen, the screening and comparison could equally as well have been made, for example, in respect of structure V (a compound selected from formula 4) and structure I (a compound selected from formula 1) with the same result that a polynucleotide comprising a region which encodes Pseudomonas HPPD is selected. In this case, the ratio, Kd4/Kd1 in respect of Pseudomonas HPPD is >4.3 which, again is >2.5 fold more than the equivalent ratio of 0.28 in respect of the Arabidopsis control enzyme. Alternatively, a polynucleotide comprising a region which encodes Pseudomonas HPPD is screened and selected on the basis that it encodes an HPPD-inhibitor resistant HPPD enzyme able to form a complex in water at pH 7.0 and at 25 C with a herbicidal HPPD inhibitor, in this case structure IV or structure VI, wherein the dissociation of the said complex is governed by a dissociation constant (Kd) in the range from 1 to 30 nM (in this case, for example, 12.2 nM) and wherein the selected HPPD-inhibitor has at least a quarter of the herbicidal activity of mesotrione versus dicot plants (this being true of both structure IV and VI).

EXAMPLE 12

Production of Stably-Transformed Morphologically Normal Fertile Soyabean Plants which Comprise a DNA Region Encoding an Avena sativa HPPD Enzyme and which are Resistant to HPPD-inhibitor Herbicides Suitable polynucleotides for plant transformation comprising a gene for expression of Avena sativa HPPD are described, for example, in the previous examples. Optionally, the HPPD gene itself can provide the means of selection and identification of transgenic tissue. Optionally the gene for expression of Avena sativa HPPD can be present in the polynucleotide alongside other sequences which provide additional means of selection/identification of transformed tissue including, for example, genes which provide resistance to kanamycin, hygromycin, phosphinothricin or glyphosate. Alternatively these selectable marker sequences may be present on separate polynucleotides and a process of, for example, transformation by co-bombardment and co-selection is used. Alternatively, rather than a selectable marker gene a scorable marker gene such as GUS may be used to identify transformed tissue. Soybean plant material can be suitably transformed and fertile plants regenerated by many methods which are well known to the skilled man. For example, fertile morphologically normal transgenic soybean plants may be obtained by 1) production of somatic embryogenic tissue from e.g. immature cotyledon, hypocotyl or other suitable tissue 2) transformation by particle bombardment or infection with Agrobacterium and 3) regeneration of plants.

Alternatively such soybean plants may be obtained by infection of buds and/or flower tissues with Agrobacterium by vacuum infiltration and selection of transgenic seed and/or plants grown from rescued embryos. In one example, as described in U.S. Pat. No. 5,024,944, cotyledon tissue is excised from immature embryos of soybean, preferably with the embryonic axis removed, and cultured on hormone-containing medium so as to form somatic embryogenic plant material. This material is transformed using, for example, direct DNA methods, DNA coated microprojectile bombardment or infection with Agrobacterium, cultured on a suitable selection medium and regenerated, optionally also in the continued presence of selecting agent, into fertile transgenic soybean plants. Selection agents may be antibiotics such as kanamycin, hygromycin or herbicides such as phosphonothricin or glyphosate or, alternatively, selection may be based upon expression of a visualisable marker gene such as GUS. Alternatively target tissues for transformation comprise meristematic rather than somaclonal embryogenic tissue or, optionally, is flower or flower-forming tissue.

In one example, constructs are transformed into regenerable embryogenic soybean tissues using either biolistic type approaches (e.g Santarem E R, Finer, J. J (1999) 'Transformation of soyabean (*Glycine max* (L.) Merrill) using proliferative embryogenic tissue maintained on a semi-solid medium. In vitro Cellular and Developmental Biology-Plant 35, 451-455; U.S. Pat. Nos. 5,503,998, 5,830,728) or via infection with *Agrobacterium* (e.g., U.S. Pat. Nos. 5,024,944, 5,959,179). Regenerable embryogenic soybean tissues are derived, for example, from the cotyledons of immature embryos.

Proliferative embryogenic tissue can, for example, be maintained on a semi-solid medium. Such tissue, is, for example obtained in the following way. Immature zygotic embryos which are 3-4 mm long are isolated from pods of, for example, *Glycine max* (L.) Merrill, 2-3 weeks after flower formation. Pods can be checked for the presence of embryos of the correct length and maturity by 'backlighting'. Pods are then sterilized. Immature embryos are removed and the axis removed from each. Immature embryos are then plated on 'D40-Lite' semi-solid (0.2% gelrite) MS salts medium at pH 7.0 containing B5 vitamins, 3% sucrose and 40 mg/l 2,4-D for 3-4 weeks. For proliferation of embryos the material is then transferred to 'D20' MS salts medium at pH 5.7 containing B5 vitamins, 3% sucrose, 20 mg/l 2,4-D and 0.2% Gelrite. Material with bright green globular proliferative embryos is selected and subcultured every 2-3 weeks.

For bombardment, 20-25 clumps/plate of tissue are selected (subcultured 4-5 days prior to bombardment) and arranged in the centre of the dish containing D20 medium. The tissue is dried for 15 min by uncovering for 15 minutes under a sterile hood. Gold particles coated in DNA construct (coated, for example, using methods described in the references above) are twice bombarded into the tissue on D20 medium using any one of a large number of commercially available guns. By way of further example a PDS1000 particle gun is used. Particles may be prepared and coated with DNA in a similar manner to that described by Klein et al 1987, Nature, 327, 70-73.

Alternatively, for example, 60 mg of gold or tungsten particles (~1.0 µm) in a microcentrifuge tube are washed repeatedly in HPLC-grade ethanol and then, repeatedly, in sterile water. The particles are resuspended in 1 ml of sterile water and dispensed into 50 µl aliquots in microcentrifuge tubes. Gold particles are stored at 4 C, tungsten particles at –20 C. 3 mg of DNA are added to each aliquot of (defrosted) particles and the tubes are vortexed at top speed. Whilst maintaining near continuous vortexing, 50 µl of 2.5M $CaCl_2$ and 20 µl of 0.1M spermidine is added. After 10 minutes of further vortexing, samples are centrifuged for 5 seconds in an eppendorf microcentrifuge, the supernatant is drawn off and the particles washed in successive additions of HPLC-grade ethanol. The particles are thoroughly resuspended in 60 µl of ethanol and then dispensed in 10 µl aliquots onto the surface of each macrocarrier to be used in the PDS1000 particle gun. Components of the PDS1000 particle gun are surface sterilised by immersion in 70% ethanol and air-drying. Target plates prepared, as described above, with tissue arranged into an ~2.5 cm disc are placed 6 cm from the stopping screen. Suitably chosen rupture discs are then used for bombardment.

One week after bombardment, all tissue clumps are transferred onto D20 medium, buffered to pH 5.7, containing a suitable selective concentration of selecting agent (for example glyphosate between 0.05 and 10 mM in the case that glyphosate be used for selection and that a resistant EPSPS or GOX encoding gene is either present on the same transforming DNA as the gene expressing *Avena sativa* HPPD or, otherwise, is present in co-bombarded DNA). After an additional 3-4 weeks all tissue is transferred to fresh D20 medium containing a suitable increased concentration of selecting agent. After a further 3-4 weeks, living tissue is selected and subcultured on every 3-4 weeks in similar D20 medium containing selection agent. In the case that some other selectable marker than glyphosate is present then selections may be made as appropriate (e.g., using increasing concentrations of hygromycin). Alternatively, all selections are made using HPPD inhibitor herbicides. Growing sections are thus maintained and, given enough tissue, may be analysed by PCR to confirm that they are transgenic for the desired DNA.

In order to develop and mature embryos, tissue clumps are placed onto M6 medium which comprises MS salts at pH 5.7 containing B5 vitamins, 6% maltose and 0.2% gelrite. 6-9 clumps are placed in a tall dish at 23° C. After 3-4 weeks, embryos elongate and can be separated and transferred to another round of incubation on M6 medium. After 4-6 weeks, embryos are cream-coloured and ready for desiccation. 9 such cream-coloured embryos are placed in a dry Petri dish, sealed with parafilm and placed onto a shelf for 2-3 days. Embryos should be somewhat flaccid and not "crispy-crunchy".

Dessicated embryos can be germinated by plating onto OMS (growth regulator-free MS medium). Following germination which normally occurs within a week plants are transferred to larger boxes and, once there is sufficient root and shoot formation, thence to soil. To prevent fungal contamination it is advisable to wash OMS from the roots with distilled water. Plants may be kept and grown under high humidity and, initially, under 24 hour lighting. Plants may be grown until about 2 feet tall under 24 hour lighting and then encouraged to flower and form pods through a shift to a 16 hour lighting regime. Seeds are collected and progeny grown on, crossed and backcrossed into order to move the transgenes into the desired plant background using the normal methods of plant breeding. Plants are routinely analysed for the presence and expression of transgenes using the normal methods of molecular biology including analysis by PCR, Southern, Western, ELISA and enzyme assay techniques.

EXAMPLE 13

Production of Stably-Transformed Morphologically Normal Fertile Corn Plants which Comprise a DNA Region Encoding an *Avena sativa* HPPD Enzyme and which are Resistant to HPPD-inhibitor Herbicides Constructs for corn transformation preferably have the DNA sequence encoding *Avena sativa* HPPD under operable expression control of the maize polyubiquitin promoter and also include a suitable terminator sequence such as that from the 3' end of the Nos gene. Optionally this DNA sequence also comprises a sequence which provide an additional means of selection/identification of transformed tissue including, for example, genes which provide resistance to kanamycin, butafenacil, hygromycin, phosphinothricin, glyphosate, or postive mannose selection. Alternatively these selectable marker sequences may be present on separate polynucleotides and a process of, for example, transformation by co-bombardment and co-selection is used. Alternatively, rather than a selectable marker gene a scorable marker gene such as GUS may be used to identify transformed tissue. The DNA sequence may be delivered to corn target tissue using many methods which are well known in the art including (i) via placement within the left and right borders of a T-DNA sequence and infection with *Agrobacterium* (ii) as a DNA coating on microprojectiles and bombardment (iii) as a coating on silicon carbide whiskers or iv) by direct DNA delivery methods.

EXAMPLE 14

Transformation of Corn Using *Agrobacterium*

For example, DNA comprising the HPPD sequence is ligated into a position within the cloning site located between the right and left T-DNA borders of similarly restricted pSB11. The construction of plasmid pSB11 and the construction of its parent, pSB21, is described by Komari et al (1996, Plant J. 10: 165-174). The T-DNA region comprising the HPPD sequence is then integrated into the superbinary pSB1 vector. (Saito et al EP 672 752 A1) by a process of homologous recombination. To achieve this the psB11 comprising the HPPD sequence is transformed into *E. coli* strain HB101 which is then, according to the triple cross method of Ditta et al (1980, Proc. Natl. Acad. Sci. USA 77: 7347-7351), mated with an *Agrobacterium* LBA4404 harbouring pSB1 to create the transformed strain of *Agrobacterium*, LBA4404 (pSB1-HPPD) in which the presence of the cointegrate plasmid pSB1-HPPD is selected for on the basis of resistance to spectinomycin. The identity of pSB1-HPPD is also confirmed on the basis of Sal 1 restriction analysis.

Alternatively, using similar methods to those described above, a similar fragment of HPPD sequence is homologously recombined into a position between the right and left borders of the superbinary vector pTOK162 (FIG. 1 in U.S. Pat. No. 5,591,616) to generate a similar set of cointegrate plasmids selected for in *Agrobacterium* on the basis of combined resistance to kanamycin and spectinomycin.

*Agrobacterium* strain LBA4404 which has a helper plasmid PAL4404 (having a complete vir region) is available from the American Type Culture Collection (ATCC 37349). An alternative useful strain is *Agrobacterium* EHA101 (1986, Hood et al, J. Bacteriol., 168(3): 1283-1290) which has a helper plasmid having the vir region from the strongly virulent strain *Agrobacterium tumefaciens* A281.

*Agrobacterium* strains LBA4404(pSB1-HPPD) etc are each streaked onto plates containing, for example, 'PHI-L' solid medium and cultured at 28 C in the dark for 3 to 10 d. PHI-L medium is as described on page 26 (Example 4) of WO 98/32326. Alternatively the *Agrobacterium* are cultured for 3-10 d on a plate containing YP medium (5 g/l yeast extract, 10 g/l peptone, 5 g/l NaCl, 15 g/l agar at pH 6.8) as described by Ishida et al (1996, Nature Biotechnology, 14, 745-750) or, alternatively, as described by Hei et al in U.S. Pat. No. 5,591, 616 (AB medium (Drlica and Kado, 1974; Proc. Natl. Acad. Sci. USA 71:3677-3681)) but, in each case, modified to provide the appropriate antibiotic selection (e.g. containing 50 μg/ml spectinomycin in the case of *Agrobacterium* strain LBA4404(pSB1-HPPD) etc. or containing both 50 μg/ml spectinomycin and 50 μg/ml kanamycin in the case that *Agrobacterium* containing a pTOK 162-derived superbinary vector is used).

Plates of *Agrobacterium* made as described above are stored at 4 C and used within a month of preparation. Suspensions of *Agrobacterium* for transformation of plant material are prepared in a similar manner to described in U.S. Pat. No. 5,591,616. (Using good microbiological practice to avoid contamination of aseptic cultures) 3×5 mm loopfuls of *Agrobacterium* are removed from plates, transferred and suspended in 5 ml of sterile AA liquid medium in a 14 ml Falcon tube. Alternatively, suspensions of *Agrobacterium* for transformation of plant material are prepared in a similar manner to described in WO 98/32326. 3×5 mm loopfuls of *Agrobacterium* are removed from plates, transferred and suspended in 5 ml of the sterile PHI-A basic medium as described in Example 4 on page 26 of WO 98/32326 or, alternatively, suspended in 5 ml of the sterile PHI-I combined medium also described in Example 4 on page 26 of WO 98/32326. Alternatively, suspensions of *Agrobacterium* for transformation of plant material are prepared in a similar manner to described by Ishida et al (1996) Nature Biotechnology, 14, 745-750. However produced, the suspension of *Agrobacterium* is vortexed to make an even suspension and the cell population adjusted to between $0.5 \times 10^9$ and $2 \times 10^9$ cfu/ml (preferably the lower). $1 \times 10^9$ cfu/ml corresponds to an OD (1 cm) of ~0.72 at 550 nm. *Agrobacterium* suspensions are aliquoted into 1 ml lots in sterile 2 ml microcentrifuge tubes and used as soon as possible Suitable maize lines for transformation include but are not restricted to, A 188, F1 P3732, F1 (A188×B73Ht), F1 (B73Ht×A188), F1 (A188×BMS). Suitable maize lines also include a variety of A188×inbred crosses (e.g PHJ90×A 188, PHN46×A188, PHPP8×A188 in table 8 of WO98/32326) as well as elite inbreds from different heterotic groups (e.g. PHN46, PHP28 and PHJ90 in table 9 of WO98/32326).

In a particular example immature embryos are produced from "Hi-II" corn. "Hi-II" is a hybrid between inbreds (A188×B73) generated by reciprocal crosses between Hi-II parent A and Hi-II parent B available from the Maize Genetic Cooperation Stock Center, University of Illinois at Champaign, Urbana, Ill.). Seeds, termed 'Hi-II' seeds obtained from these crosses are planted out in a greenhouse or field. The resulting Hi-II plants are self or cross-pollinated with sister plants Transformation of immature embryos of corn is carried out by contacting the immature embryos with the suitable recombinant strains of *Agrobacterium* described above. An immature embryo means the embryo of an immature seed which is in the stage of maturing following pollination. Immature embryos are an intact tissue that is capable of cell division to give rise to callus cells that can then differentiate to produce the tissues and organs of a whole plant. Preferred material for transformation also includes the scutella of embryos which is also capable of inducing dedifferentiated calli with the ability to regenerate normal fertile plants having been initially transformed. Preferred material for transformation thus also includes callus derived from such dedifferentiated immature zygotic embryos or scutella.

Immature corn embryos are isolated aseptically from developing ears as described by Green and Phillips (1976, Crop. Sci. 15: 417-421) or, alternatively, by the methods of Neuffer et al (1982, "Growing Maize for genetic purposes" in *Maize for biological research*, W. F. Sheridan ed., University Press, University of North Dakota, Grand Forks, N. Dak., USA). For example, immature corn embryos between 1-2 mm (preferably 1-1.2 mm) long are aseptically isolated from female spikes at 9-12 (preferably 11) d after pollination using a sterile spatula. Typically ears are surface sterilised with 2.63% sodium hypochlorite for 20 min before washing with sterile deionized water and aseptic removal of immature embryos. Immature embryos (preferably ~100 in number) are dropped directly into a 2 ml microcentrifuge tube containing about 2 ml of the same medium as used for preparing the suspension of *Agrobacterium* (the alternatives for which are described above). The cap of the tube is closed and the contents mixed by vortexing for a few seconds. The medium is decanted off, 2 ml of fresh medium are added and vortexing is repeated. All of the medium is then drawn off to leave the washed immature embryos at the bottom of the tube.

Having prepared the immature maize embryos the next phase of the process, the infection step, is to contact them with the transformed strain of *Agrobacterium*. In one example of this process, the infection step takes place in a liquid medium which includes the major inorganic salts and vitamins of N6 medium (1987, Chu C. C. Proc. Symp. Plant Tissue Culture, Science Press Peking. Pp 43-50) as described in example 4 of WO 98/32326. For example, as described in WO 98/32326, 1.0 ml of suspension of *Agrobacterium*, prepared as described above in PHI-A medium is added to the embryos in the microcentrifuge tube and vortexed for about 30 s. Alternatively, 1.0 ml of suspension of *Agrobacterium* prepared, also as described above, in either PHI-I medium or in LS-inf medium is added. After standing for 5 minutes the suspension of *Agrobacterium* and embryos is poured out into a Petri plate containing either 1) PHI-B medium or 2) PHI-J medium or 3) LS-AS medium according to whether the original suspension of *Agrobacterium* had been prepared in PHI-A medium, PHI-I medium or LS-inf medium, respectively. The *Agrobacterium* suspension is drawn off using a Pasteur pipette, the embryos manipulated so that they sit axis-side downwards onto the medium, the plate sealed with parafilm and incubated in the dark at 23-25 C for 3 days of cocultivation.

Following the preparation of immature embryos, an alternative method of achieving transformation is to infect them during and after a period of dedifferentiation as described in U.S. Pat. No. 5,591,616. Immature embryos are placed on LSD 1.5 solid medium containing LS inorganic salts and vitamins along with 100 mg/ml casamino acids, 700 mg/l L-proline, 100 mg/l myo-inositol, 1.5 mg/ml of 2,4-D, 20 g/l sucrose and 2.3 g/l of gelrite. After 3 weeks at 25 C, calli originating from the scutella are collected in a 2 ml microcentrifuge tube and immersed in 1 ml of *Agrobacterium* suspension prepared, as described above, in AA medium. After standing for 5 minutes, the resultant calli are transferred to 2N6 solid medium containing 100 μM acetosyringone and incubated in the dark at 25 C for a 3 day period of cocultivation.

For the selection step, about 20 embryos are transferred onto each of a number of fresh plates containing PHI-D (WO 98/32326) selection medium or LSD 1.5 (U.S. Pat. No. 5,591, 616) selection medium, sealed with parafilm and incubated in the dark at 28 C. Selection media, adjusted to pH 5.8 with KOH, contain, depending upon the presence of selectable marker genes, suitable concentrations of selecting agents. For example, an HPPD-inhibitor herbicide and/or, in the case that a gene encoding a resistant EPSPS enzyme be used, concentrations of between 0.1 mM and 20 mM of tissue culture grade N-concentrations of (Phosphonomethyl)-glycine (Sigma P-9556) may be used. In the case that a resistant protoporphyrinogen oxidaser gene be used, then butafenacil can be used as selection agent. Alternatively selection media are designed to give positive selection on mannose (Positech™ technology). Alternatively, in the case that the starting material for selection are calli-derived from immature embryos as disclosed in WO 5591616 then such calli are washed with sterilised water containing 250 mg/l cefotaxime before culturing on LSD 1.5 selection medium adjusted to provide suitable selection.

The embryos or clusters of cells that proliferate from the immature embryos are transferred (if necessary using a sterile scalpel) to plates containing fresh selection medium at 2 weekly intervals over a total period of about 2 months. Selected calli are then bulked by continued growth on the same medium until the diameter of the selected callus exceeds about 1.5 cm.

The selected calli are regenerated into normal fertile plants according to, for example, the methods described by Duncan et al (1985, Planta, 165, 322-332) by Kamo et al (1985, Bot. Gaz. 146(3), 327-334) and/or by West et al (1993, The Plant Cell, 5, 1361-1369) and/or by Shillito et al (1989) Bio/Technol. 7, 581-587. Optionally the regeneration medium may also be adjusted to provide for continued positive mannose selection or other selection.

For example, selected calli of diameter 1.5-2 cm are transferred to regeneration/maturation medium and incubated in the dark for about 1-3 weeks to allow the somatic embryos to mature. A suitable regeneration medium, is, for example, PHI-E medium (WO 98/32326) adjusted to pH 5.6 with KOH, which may also, optionally, contain selection agent or be adjusted to provide for continued positive mannose selection.

The calli are then transferred to rooting/regeneration medium and grown at 25 C under either a schedule of 16 h daylight (270 mE m$^{-2}$ s$^{-1}$) and 8 h of darkness or under continuous illumination (~250 mE m$^{-2}$ s$^{-1}$) until such a time as shoots and roots develop. Suitable rooting/regeneration media are either LSZ medium (optionally, including or not including, continued selection). Alternatively, selected calli are transferred directly to LSZ regeneration medium adjusted to pH 5.8 with KOH and comprising LS major and minor inorganic salts (Linsmaier and Skoog, 1965, Physiol. Plant 18, 100-127), 0.5 mg/ml nicotinic acid, 0.5 mg/ml pyridoxine. HCl, 1.0 mg/ml thiamine. HCL, 700 mg/l L-proline, 100 mg/l myo-inositol, 5 mg/ml of zeatin, 20 g/l sucrose, 0.5 g/l MES, 250 mg/l cefotaxime, 8 g/l purified agar (Sigma A-7049) or, optionally, suitably adapted to provide continued selection (for example, on mannose, or containing an HPPD-inhibitor herbicide or glyphosate etc). After a period of incubation in the dark plates are subject to illumination (continuous or light/day as above) and plantlets regenerated.

Small plantlets are transferred to individual glass tubes containing, for example, either PHI-F medium or half strength LSF medium at pH 5.8 comprising LS major salts (Linsmaier and Skoog, 1965, Physiol. Plant 18, 100-127) at half strength, LS minor salts, 0.5 mg/ml nicotinic acid, 0.5 mg/ml pyridoxine. HCl, 1.0 mg/ml thiamine. HCL, 100 mg/l myo-inositol, 20 g/l sucrose, 0.5 g/l MES, 8 g/l purified agar (Sigma A-7049). and grown on for about another week. Plantlets are then transferred to pots of soil, hardened off in a growth chamber (85% relative humidity, 600 ppm $CO_2$ and 250 mE m$^{-2}$ s$^{-1}$) and grown to maturity in a soil mixture in a greenhouse.

The first (To) generation of plants obtained as above are self fertilised to obtain second generation (T1) seeds. Alternatively (and preferably) the first generation of plants are reciprocally crossed with another non-transgenic corn inbred line in order to obtain second generation seeds. The progeny of these crosses (T1) are then expected to segregate 1:1 for the herbicide resistance trait. T1 seeds are sown, grown up in the glass house or field and the level of resistance, inheritance of resistance and segregation of resistance to selected HPPD-inhibitor herbicides through this and subsequent generations assessed by the observation of differential plant survival and the easy to score symptoms of bleaching and chlorosis following spray treatment with suitably formulated HPPD-inhibitor herbicides such as structure VI, isoxaflutole and structure II at a range of rates between 5 and 2000 g/ha and at a range of growth stages between and including V2 and V8 (or, alternatively, at 7-21 days post germination). These assessments are made relative to susceptible segregants and relative to similar, untransformed lines of corn which do not comprise genes of the present or similar inventions capable of conferring resistance to glyphosate. Transgenic lines which exhibit high-level resistance to HPPD-inhibitor herbicides are selected and again selfed or backcrossed to a non-transgenic inbred.

At all stages in the above process tissue samples of transformed callus, plantlets, T0 and T1 plant material are optionally taken and analysed by 1) Southerns and PCR in order to indicate the presence, copy number and integrity of transgenes, 2) Northern (or similar) analysis in order to measure expression of mRNA from transgenes, 3) quantitative Western analysis of SDS gels in order to measure expression levels of EPSPS and 4) measurement of HPPD enzyme activity Such methods of analysis are well known in the art. Suitable methods to test for the presence, integrity and expression of the transgene include PCR, Southern analysis, and Western analysis.

Other Methods of Corn Transformation

In a further example, friable embryogenic callus derived from immature embryos of A188×B73 corn is initiated on a solid medium and transformed biolistically. Suitable methods are described, for example, in WO 98/44140 and U.S. Pat. No. 5,550,318. DNA is provided as a circular plasmid DNA or, alternatively is restricted to provide a linear EPSPS-expression cassette-containing fragment and used following purification by agarose gel electrophoresis and electroelution. In a further example, maize lines including, for example, hybrid lines having the genotype A188×B73 are prepared as cell suspensions and transformed by contacting the cell with silicon carbide whiskers coated with DNA using methods essentially as described by Frame et al (1994, Plant J. 6, 941-948).

EXAMPLE 15

In vitro Measurements of *Avena* HPPD

In accord with the methods described in the previous examples, *Avena* HPPD is found to have a Km value for HPP of ~2.5 µM and a $k_{cat}$/Km value of ~2+/−0.6/s/µmol.

At 25° C. and in the absence of glycerol, the rate constants governing dissociation of the complexes with I, II, IV and V are similar to those observed with wheat enzyme and are estimated as $>{\sim}8{\times}10^{-4}$/s, $\sim{4}{\times}10^{-4}$/s, $\sim{2.5}{\times}10^{-5}$/s and $<4{\times}10^{-6}$/s. Corresponding Ki values were estimated as >11500 pM, 11400 pM, 710 pM and <30 pM.

Whilst the invention has been particularly described by reference to the introduction of the *Avena* gene into soybean, maize and tobacco, the skilled man will recognise that many variations to that specifically described are possible without departing from the scope of the invention which is defined by the appended claims. For example, any suitable plant transformation technique, such as micro-injection, particle mediated bombardment, polyethylene glycol mediated protoplast transformation, electroporation, protoplast or plant cell sonication etc. may be used to introduce the polynucleotide or vector of the invention into any monocot. or dicot. plant material, which may then be regenerated by known techniques. In particular, for generating plants which are resistant to syncarpic acids (Formula 4) the HPPD encoding sequence from *Shewenella Colwelliana* is particularly preferred

The invention claimed is:

1. A method of selectively controlling weeds at a locus comprising crop plants and weeds, the method comprising: applying to the locus a sufficient amount of an HPPD inhibitor to control the weeds, wherein the crop plants comprise a heterologous polynucleotide encoding a HPPD-inhibitor resistant HPPD enzyme comprising an amino acid sequence selected from the group consisting of (a) SEQ ID NO: 4 and (b) a sequence comprising SEQ ID NOs: 33 and 34 and that has at least 91% identity with SEQ ID NO: 4.

2. The method according to claim 1 wherein the polynucleotide further comprises a region which encodes a protein capable of targeting the HPPD encoded by the sequence to subcellular organelles such as the chloroplast or mitochondria.

3. The method according to claim 2, wherein the targeting protein has the sequence of (i) a chloroplast transit peptide or (ii) a chloroplast transit peptide-N-terminal portion of a chloroplast protein-chloroplast transit peptide.

4. The method according to claim 3 wherein the polynucleotide further comprises a sequence encoding an HPPD-inhibiting herbicide degrading or otherwise detoxifying enzyme, and/or a protein otherwise capable of specifically binding to the said HPPD-inhibiting herbicide.

5. The method according to claim 4, wherein the crop plant further comprises a polynucleotide comprising a region encoding (i) the target for a non-HPPD inhibitor herbicide and/or (ii) a non-HPPD inhibitor herbicide degrading or otherwise detoxifying enzyme and/or a region encoding a protein capable of conferring on plant material transformed with the region resistance to insects, fungi and/or nematodes.

6. The method according to claim 5 wherein said target or enzyme is selected from the group consisting of a cytochrome p450, a glutathione S transferase, glyphosate oxidase (GOX), phosphinothricin acetyl transferase (PAT), 5-enolpyruvylshikimate-3-phosphate synthase (EPSPS), acetolactate synthase (ALS), protoporphyrinogen oxidase (PPGO) and phytoene desaturase (PD) or mutagenised or otherwise modified forms thereof.

7. The method according to claim 1 wherein the HPPD inhibitor is selected from the group consisting of a Formula 1 herbicide, a Formula 2 herbicide, a Formula 3 herbicide, and a Formula 4 herbicide.

8. The method according to claim 5, further comprising application to the locus of a pesticide selected from the group consisting of an insecticide, a fungicide and a non-HPPD inhibitor herbicide.

9. The method according to claim 8 wherein the herbicide resistant crop plants are selected from the group consisting of soybean, wheat, rice, maize, barley, tobacco, cotton, canola, sunflower, sugar beet, sorghum, tomato, mango, peach, apple, pear, strawberry, banana, melon, mangel-wurzel, potato, carrot, lettuce, cabbage, and onion.

10. The method according to claim 7, wherein the HPPD inhibitor is mesotrione.

11. The method according to claim 7, wherein the HPPD inhibitor is isoxaflutole.

12. The method according to claim 1, wherein the HPPD inhibitor is applied pre-emergence.

13. The method according to claim 1, wherein the HPPD inhibitor is applied post-emergence.

* * * * *